(12) United States Patent
Makarov et al.

(10) Patent No.: US 9,598,727 B2
(45) Date of Patent: Mar. 21, 2017

(54) METHODS FOR PROCESSING AND AMPLIFYING NUCLEIC ACIDS

(71) Applicant: Rubicon Genomics, Inc., Ann Arbor, MI (US)

(72) Inventors: Vladimir L. Makarov, Ann Arbor, MI (US); Emmanuel Kamberov, Ann Arbor, MI (US); Brendan J. Tarrier, Belleville, MI (US)

(73) Assignee: Rubicon Genomics, Inc., Ann Arbor, MI (US)

( * ) Notice: Subject to any disclaimer, the term of this patent is extended or adjusted under 35 U.S.C. 154(b) by 190 days.

(21) Appl. No.: 14/250,538

(22) Filed: Apr. 11, 2014

(65) Prior Publication Data
US 2015/0079637 A1   Mar. 19, 2015

Related U.S. Application Data

(63) Continuation of application No. 13/766,607, filed on Feb. 13, 2013, now Pat. No. 8,728,737, which is a
(Continued)

(51) Int. Cl.
  *C12P 19/34*  (2006.01)
  *C12Q 1/68*   (2006.01)
  *C12N 15/10*  (2006.01)

(52) U.S. Cl.
  CPC ....... *C12Q 1/6853* (2013.01); *C12N 15/1068* (2013.01); *C12P 19/34* (2013.01);
  (Continued)

(58) Field of Classification Search
  USPC ............................................... 435/6.12, 91.2
  See application file for complete search history.

(56) References Cited

U.S. PATENT DOCUMENTS

| 5,043,272 A | 8/1991 | Hartley |
| 5,104,792 A | 4/1992 | Silver et al. |

(Continued)

FOREIGN PATENT DOCUMENTS

| EP | 0 466 520    | 1/1992 |
| EP | 0 684 315 A1 | 11/1995 |

(Continued)

OTHER PUBLICATIONS

Adam et al., "Cross-linking of the p55 Tumor Necrosis Factor Receptor cytoplasmic Domain by a dimeric Ligand Induces Nuclear Factor-kB and Mediates Cell Death," J. Biol. Chem., 270(29): 17482-17487, 1995.

(Continued)

*Primary Examiner* — Kenneth Horlick
(74) *Attorney, Agent, or Firm* — Parker Highlander PLLC

(57) ABSTRACT

The present invention is directed generally to the use of stem-loop oligonucleotides comprising an inverted repeat, a loop, and at least one degradable site or site capable of becoming a degradable site in the preparation of DNA molecules, such as a library. In particular embodiments, the invention employs a single reaction mixture and conditions. In particular, at least part of the inverted palindrome is removed during the preparation of the molecules to facilitate amplification of the molecules. Thus, in specific embodiments, the DNA molecules are suitable for amplification and are not hindered by the presence of the palindrome.

33 Claims, 60 Drawing Sheets

Related U.S. Application Data continuation of application No. 13/286,937, filed on Nov. 1, 2011, now Pat. No. 8,399,199, which is a continuation of application No. 12/892,359, filed on Sep. 28, 2010, now Pat. No. 8,071,312, which is a continuation of application No. 12/270,850, filed on Nov. 13, 2008, now Pat. No. 7,803,550, which is a continuation of application No. 11/366,222, filed on Mar. 2, 2006, now abandoned.

(60) Provisional application No. 60/704,932, filed on Aug. 2, 2005.

(52) U.S. Cl.
CPC ........... *C12Q 1/686* (2013.01); *C12Q 1/6855* (2013.01); *C12Q 1/6865* (2013.01)

(56) References Cited

U.S. PATENT DOCUMENTS

| | | | |
|---|---|---|---|
| 5,106,727 | A | 4/1992 | Hartley et al. |
| 5,405,760 | A | 4/1995 | Raleigh et al. |
| 5,470,724 | A | 11/1995 | Ahern |
| 5,514,545 | A | 5/1996 | Eberwine |
| 5,714,318 | A | 2/1998 | Sagner et al. |
| 5,731,171 | A | 3/1998 | Bohlander |
| 5,759,821 | A | 6/1998 | Teasdale |
| 5,759,822 | A | 6/1998 | Chenchik et al. |
| 5,932,451 | A | 8/1999 | Wang et al. |
| 5,948,649 | A | 9/1999 | Stewart et al. |
| 5,968,743 | A | 10/1999 | Matsunaga et al. |
| 5,994,058 | A | 11/1999 | Senapathy |
| 6,045,994 | A | 4/2000 | Zabeau et al. |
| 6,060,245 | A | 5/2000 | Sorge et al. |
| 6,107,023 | A | 8/2000 | Reyes et al. |
| 6,114,149 | A | 9/2000 | Fry et al. |
| 6,124,120 | A | 9/2000 | Lizardi |
| 6,214,556 | B1 | 4/2001 | Olek et al. |
| 6,261,774 | B1 | 7/2001 | Pagratis et al. |
| 6,280,949 | B1 | 8/2001 | Lizardi |
| 6,300,071 | B1 | 10/2001 | Vuylsteke et al. |
| 6,365,375 | B1 | 4/2002 | Dietmaier et al. |
| 6,379,932 | B1 | 4/2002 | Arnold et al. |
| 6,383,754 | B1 | 5/2002 | Kaufman et al. |
| 6,403,319 | B1 * | 6/2002 | Lizardi ............ C07K 14/70578 435/6.1 |
| 6,451,563 | B1 | 9/2002 | Wittig et al. |
| 6,498,023 | B1 | 12/2002 | Abarzua |
| 6,509,160 | B1 | 1/2003 | Sapolsky et al. |
| 6,521,428 | B1 | 2/2003 | Senapathy |
| 6,537,757 | B1 | 3/2003 | Langmore et al. |
| 6,576,448 | B2 | 6/2003 | Weissman et al. |
| 6,605,432 | B1 | 8/2003 | Huang |
| 6,621,782 | B1 | 9/2003 | Nakane et al. |
| 6,632,611 | B2 | 10/2003 | Su et al. |
| 6,638,722 | B2 | 10/2003 | Ji et al. |
| 6,677,121 | B2 | 1/2004 | Lizardi et al. |
| 6,692,915 | B1 | 2/2004 | Nallur |
| 6,692,918 | B2 | 2/2004 | Kurn |
| 6,762,022 | B2 | 7/2004 | Makarov et al. |
| 6,773,886 | B2 | 8/2004 | Kaufman et al. |
| 6,787,308 | B2 | 9/2004 | Balasubramanian et al. |
| 6,808,888 | B2 | 10/2004 | Zhang et al. |
| 6,825,010 | B2 | 11/2004 | Spier et al. |
| 6,974,141 | B2 | 12/2005 | Kim |
| 2001/0021518 | A1 | 9/2001 | Goudsmit et al. |
| 2001/0046669 | A1 | 11/2001 | McCobmie et al. |
| 2002/0058250 | A1 | 5/2002 | Firth |
| 2002/0192769 | A1 | 12/2002 | Park et al. |
| 2003/0013671 | A1 | 1/2003 | Mineno et al. |
| 2003/0064393 | A1 | 4/2003 | Bass et al. |
| 2003/0099997 | A1 | 5/2003 | Bestor |
| 2003/0129602 | A1 | 7/2003 | Huang |
| 2003/0143599 | A1 | 7/2003 | Makarov et al. |
| 2003/0165885 | A1 | 9/2003 | Arnold et al. |
| 2003/0186237 | A1 | 10/2003 | Ginsberg et al. |
| 2003/0232371 | A1 | 12/2003 | Bestor |
| 2004/0043416 | A1 | 3/2004 | Ji et al. |
| 2004/0063144 | A1 | 4/2004 | Lizardi |
| 2004/0115616 | A1 | 6/2004 | Holton |
| 2004/0209298 | A1 | 10/2004 | Kamberov et al. |
| 2004/0209299 | A1 | 10/2004 | Pinter et al. |
| 2005/0202490 | A1 | 9/2005 | Makarov et al. |
| 2006/0110745 | A1 | 5/2006 | Hayashizaki et al. |
| 2006/0166250 | A1 | 7/2006 | Brenner et al. |
| 2006/0216724 | A1 | 9/2006 | Christians et al. |
| 2007/0128620 | A1 * | 6/2007 | Lao ..................... C12Q 1/6844 435/6.11 |

FOREIGN PATENT DOCUMENTS

| | | |
|---|---|---|
| EP | 0 976 835 | 2/2000 |
| EP | 1 275 738 | 1/2003 |
| JP | 8173164 | 7/1996 |
| WO | WO-93/24654 A1 | 12/1993 |
| WO | WO-96/15264 | 5/1996 |
| WO | WO-97/30062 | 8/1997 |
| WO | WO-98/02575 | 1/1998 |
| WO | WO-98/15652 A1 | 4/1998 |
| WO | WO-98/39485 | 9/1998 |
| WO | WO-99/28498 | 6/1999 |
| WO | WO-00/17390 | 3/2000 |
| WO | WO-01/09384 | 2/2001 |
| WO | WO-01/51661 | 7/2001 |
| WO | WO-01/57248 | 9/2001 |
| WO | WO-02/06533 | 1/2002 |
| WO | WO-02/20571 | 3/2002 |
| WO | WO-02/060318 | 8/2002 |
| WO | WO-02/072772 | 9/2002 |
| WO | WO-02/101022 | 12/2002 |
| WO | WO-02/103054 | 12/2002 |
| WO | WO-03/012118 | 2/2003 |
| WO | WO-03/016546 | 2/2003 |
| WO | WO-03/025215 | 3/2003 |
| WO | WO-03/027259 | 4/2003 |
| WO | WO-03/035860 | 5/2003 |
| WO | WO-03/050242 | 6/2003 |
| WO | WO-03/087774 | 10/2003 |

OTHER PUBLICATIONS

Ailenberg et al., "Controlled Hot Start and Improved Specificity in Carrying Out PCR Utilizing Touch-Up and Loop Incorporated Primers (TULIPS)," BioTechniques, 29: 1018-1024, 2000.

Badal et al., "CpG Methylation of Human Papillomavirus Type 16 DNA in Cervical Cancer Cell Lines and in Clinical Specimens: Genomic Hypomethylation Correlates with Carcinogenic Progression," Journal of Virology, 77(11): 6227-6234, 2003.

Baldini et al., "Chromosomal assignment of human YAC clones by fluorescence in situ hybridization: use of single-yeast-colony PCR and multiple labeling," Genomics, 14: 181-184, 1992.

Barbaux et al., "Use of degenerate oligonucleotide primed PCR (DOP-PCR) for the genotyping of low-concentration DNA samples," J Mol Med, 79: 329-332, 2001.

Beekman et al., "A powerful and rapid approach to human genome scanning using small quantities of genomic DNA," Genet. Res. Camb., 77: 129-134, 2001.

Bellizzi et al., "A procedure for cloning genomic DNA fragments with increasing thermoresistance," Gene, 219: 63-71, 1998.

Bohlander et al., "A Method for the Rapid Sequence-Independent Amplification of Microdissected Chromosomal Material," Genomics, 13:1322-1324, 1992.

Breen et al., "YAC mapping by FISH using Alu-PCR-generated probes," Genomics, 13: 726-730, 1992.

Broude, "Stem-loop oligonucleotides: a robust tool for molecular biology and biotechnology," Trends in Biotechnology, 20: 249-256, 2002.

Buchanan et al., "Long DOP-PCR of rare archival anthropological samples," Hum. Biol., 72(6): 911-25, 2000.

(56) References Cited

OTHER PUBLICATIONS

Campbell et al., "The effect of divalent cations on the mode of action DNase 1. The initial reaction products produced from covalently closed circular DNA," J. Biol. Chem., 255: 3726-3735, 1980.
Champoux, "DNA Topoisomerases: Structure, Function, and Mechanism," Annu. Rev. Biochem., 369-413, 2001.
Chang et al., "PCR amplification of chromosome-specific DNA isolated from flow cytometry-sorted chromosomes," Genomics, 12:307-312, 1992.
Chen et al., "Methylation Target Array for Rapid Analysis of CpG Island Hypermethylation in Multiple Tissue Genomes," Am. J. Pathol., 163(1): 37-45, 2003.
Cheng et al., "Degenerate oligonucleotide primed-polymerase chain reaction and capillary electrophoretic analysis of human DNA on microchip-based devices," Anal. Biochem., 257(2): 101-6, 1998.
Cheung et al., "Whole genome amplification using a degenerate oligonucleotide primer allows hundreds of genotypes to be performed on less than one nanogram of genomic DNA," Proc. Natl. Acad. Sci. USA, 93: 14676-14679, 1996.
Chotai et al., "A rapid, PCR based test for differential molecular diagnosis of Prader-Willi and Angelman syndromes," J. Med. Genet., 35: 472-475, 1998.
Clay et al., "Using analytical ultracentrifugation to study compositional variation in vertebrate genomes," Eur. Biophys. J., 32: 418-426, 2003.
Cross et al., "CpG island libraries from human chromosomes 18 and 22: landmarks for novel genes," Mammalian Genome, 11: 373-383, 2000.
Cross et al., "Isolation of CpG islands from large genomic clones," Nucleic Acid Res., 27: 2099-2107, 1999.
Dean et al., "Comprehensive human genome amplification using multiple displacement amplification," PNAS, 99(8): 5261-5266, 2002.
DeRisi Laboratory, Dept. of Biochemistry and Biophysics, Univ. of California at San Francisco, "Random DNA Amplification. Directions for amplifying products for printing on arrays," 2001.
Devon et al., "Splinkerettes—improved vectorettes for greater efficiency in PCR walking," *Nucleic Acids Research*, 23:1644-5, 1995.
European Office Action, issued in European Application No. 06 736 752.4-1222, mailed Jan. 18, 2010.
Frigola et al., "Methylome profiling of cancer cells by amplification of inter-methylated sites (AIMS)," Nucleic Acids Res., 30(7): e28, 2002.
Fu et al., "Sequencing Double-Stranded DNA by Strand Displacement," Nucleic Acids Research, 25(3): 677-679, 1997.
Grace et al., "Degradable dUMP Outer Primers in Merged Tandem (M/T)-Nested PCR: Low- and Single-Copy DNA Target Amplification," Analytical Biochemistry, 263: 85-92, 1998.
Grothues et al., "PCR amplification of megabase DNA with tagged random primers (T-PCR)," Nucleic Acids Res., 21(5):1321-1322, 1993.
Guan et al., "Generation of band-specific painting probes from a single microdissected chromosome," Human Mol. Genet., 2(8): 1117-1121, 1993.
Guilfoyle et al., "Ligation-mediated PCR amplification of specific fragments from a Class-II restriction endonuclease total digest," Nucleic Acids Res., 25(9):1854-1858, 1997.
Hadano et al., "Laser microdissection and single unique primer PCR allow generation of regional chromosome DNA clones from a single human chromosome," Genomics, 11:364:373, 1991.
Hawkins et al., "Whole genome amplification—applications and advances," Current Opinion in Biotechnology, 13: 65-67, 2002.
Hengen, "Methods and reagents: Vectorette, splinkerette and boomerang DNA amplification," *Trends in Biochemical Sciences*, 20:372-3, 1995.
Huang et al., "Methylation profiling of CpG islands in human breast cancer cells," Human Molecular Genetics, 8(3): 459-470, 1999.
Igloi, "Substrate properties of fluorescent ribonucleotides in the terminal transferase-catalyzed labeling of DNA sequencing primers," Biotechniques, 21: 1084-1092, 1996.

Invitrogen Corporation, Carlsbad, California 92008, TOPO TA Cloning. Version P 051302 / 25-0184, pp. 1-32, 1999-2002.
Jones et al., "Amplification of 4-9-kb Human Genomic DNA Flanking a Known Site Using a Panhandle PCR Variant," BioTechniques, 23: 132-138, 1997.
Kaboev et al., "PCR hot start using primers with the structure of molecular beacons (hairpin-like structure)," Nucleic Acids Research, 28(21): e94, 2000.
Kaiser et al., "Specific-primer-directed DNA sequencing using automated fluorescent detection," Nucleic Acids Res., 17: 6087-6102, 1989.
Kalisch et al., "Covalently linked sequencing primer linkers (splinkers) for sequence analysis of restriction fragments," *Gene*, 44:263-70, 1986.
Kao et al., "Chromosome microdissection and cloning in human genome and genetic disease analysis," Proc. Natl. Acad. Sci. USA, 88:1844-1848, 1991.
Kaur Manjit et al, "Novel amplification of DNA in a hairpin structure: towards a radical elimination of PCR errors from amplified DNA", Nucleic Acids Research, vol. 31, No. 6, 2003.
Kempf et al., "Improved stimulation of human dendritic cells by receptor engagement with surface-modified microparticles," J Drug Target, 2003.
Kikuchi et al., "Expression profiles of non-small cell lung cancers on cDNA microarrays: Identification of genes for prediction of lymph-node metastasis and sensitivity to anti-cancer drugs," Oncogene, 2192-2205, 2003.
Kilger et al., "Direct DNA sequence determination from total genomic DNA," Nucleic Acids Research, 25(10): 2032-2034, 1997.
Kinzler et al., "Whole genome PCR: application to the identification of sequences bound by gene regulatory proteins," Nucleic Acids Research, 17(10): 3645-3653, 1989.
Kittler et al., "A Whole Genome Amplification Method to Generate Long Fragments from Low Quantities of Genomics DNA", Anal. Biochem. 300: 237-244, 2001.
Klein et al., "Comparative genomic hybridization, loss of heterozygosity, and DNA sequence analysis of single cells," Proc. Natl. Acad. Sci. USA, 96: 4494-4499, 1999.
Ko et al. "Unbiased amplification of highly complex mixture of DNA fragments by 'lone linker'-tagged PCR," Nucleic Acids Res., 18: 4293-4294, 1990.
Kong et al., "PCR hot-start using duplex primers," Biotechnology Letters, 26: 277-280, 2004.
Kusov et al., "A new G-tailing method for the determination of the poly(A) tail length applied to hepatitis A virus RNA," Nucleic Acids Research, 29(12): e57, 2001.
Kuukasjarvi et al., "Optimizing DOP-PCR for Universal Amplificatino of Small DNA Samples in Comparative Genomic Hybridization," Genes, Chromosomes & Cancer, 18: 94-101, 1997.
Lengauer et al., "Fluorescence in situ hybridization of YAC clones after Alu-PCR amplification," Genomics, 13: 826-828, 1992.
Lerman et al., "Sequence-determined DNA separations," Annu. Rev. Biophys. Bioeng., 13: 399-423, 1984.
Lisitsyn et al., "Cloning the differences between two complex genomes," Science, 259: 946-951, 1993.
Liu Chih Long et al, "Development and validation of a T7 based linear amplification for genomic DNA", BMC Genomics, vol. 4, No. 19, 2003.
Lucito et al., "Genetic analysis using genomic representations," Proc. Natl. Acad. Sci. USA, 95: 4487-4492, 1998.
Ludecke et al., "Cloning defined regions of the human genome by microdissection of banded chromosomes and enzymatic amplification," Nature, 338(6213): 348-50, 1989.
Makrigiorgos et al., "A PCR-based amplification method retaining the quantitative difference between two complex genomes," Nature Biotechnology, 20: 937-939, 2002.
McGrath et al., "Sequence analysis of DNA randomly amplified from the *Saccharomyces cerevisiae* genome," Molecular and Cellular Probes,, 12: 397-405, 1998.
Melief et al., "Effective theraputic anticancer vaccines based on precision guiding of cytolytic T lymphocytes," Immunol Rev., 2002.

(56) References Cited

OTHER PUBLICATIONS

Miyashita et al., "A mouse chromosome 11 library generated from sorted chromosomes using linker-adapter polymerase chain reaction," Cytogenet. Cell Genet. 66: 454-57, 1994.
Mullis et al., "Specific enzymatic amplification of DNA in vitro: the polymerase chain reaction," Cold Spring Harbor Symp., 263-273, 1986.
Nelson et al., "Alu-primed polymerase chain reaction for regional assignment of 110 yeast artificial chromosome clones from the human X chromosome: identification of clones associated with a disease locus," PNAS, 88: 6157-6161, 1991.
Nishigaki et al., "Whole genome sequence-enabled prediction of sequences performed for random PCR products of *Escherichia coli*," Nucleic Acids Research, 28(9): 1879-1884, 2000.
Office Action issued in U.S. Appl. No. 11/366,222, dated Jan. 23, 2008.
Office Action issued in U.S. Appl. No. 11/366,222, dated May 14, 2008.
Office Action issued in U.S. Appl. No. 12/270,850, dated Dec. 2, 2009.
Office Action issued in U.S. Appl. No. 12/892,359, dated Jan. 10, 2011.
Office Action issued in U.S. Appl. No. 13/286,937, dated Apr. 10, 2012.
Office Action issued in U.S. Appl. No. 13/286,937, dated May 23, 2012.
Office Action issued in U.S. Appl. No. 13/766,607, dated Oct. 31, 2013.
PCT International Preliminary Examination Report, PCT NL01 00020, dated Mar. 25, 2003.
PCT International Search, PCT-NL01 00020, dated Jul. 18, 2002.
Perou et al., "Molecular Portraits of Human Breast Tumors," Nature, 406, 2000.
Pfeifer, "Chromatin structure analysis by ligation-mediated and terminal transferase-mediated polymerase chain reaction," Methods Enzymol., 304: 548-571, 1999.
Phillips et al., "Antisense RNA Amplification: A Linear Amplification Method for Analyzing the mRNA Population from Single Living Cells," Methods: Acompanion to Methods in Enzymology 10, Article No. 0104, 283-288, 1996.
Pirker C. et al., "Whole Genome Amplification for CGH Analysis: Linker-Adapter PCR as the Method of Choice for Difficult and Limited Samples", Cytometry, vol. 61A, No. 1, 2004.
Reyes, Gregory R., et al.; Sequence-independent, single-primer amplification (SISPA) of complex DNA populations; Molecular and Cellular Probes 5: 473-481, 1991.
Riccelli et al., "Hybridization of single-stranded DNA targets to immobilized complementary DNA probes: comparison of hairpin versus linear capture probes," Nucleic Acids Research, 29: 996-1004, 2001.
Rose et al., "Consensus-degenerate hybrid oligonucleotide primers for amplification of distantly related sequences," Nucleic Acids Research, 26(7): 1628-1635, 1998.
Sanchez-Cespedes et al., "Degenerate oligonucleotide-primed PCR (DOP-PCR): evaluation of its reliability for screening of genetic alterations in neoplasia," Biotechniques, 25(6): 1036-8, 1998.
Sato et al., "Combination of monocyte-derived dendritic cells and activated T cells which express CD40 ligand: a new approach to cancer immunotherapy," Cancer Immunol. Immunother. 53(1): 53-61, 2004.
Saunders et al., "PCR amplification of DNA microdissected from a single polytene chromosome band: A comparison with conventional microcloning," Nucleic Acids Res., 17: 9027-9037, 1989.
Schiefermayr et al., "Degradation of DNA sequencing primers by a terminal transferase-associated exonuclease," Anal. Biochem., 230: 180-182, 1995.
Schmidt et al., "CapSelect: A highly sensitive method for 5' CAP-dependant enrichment of full-length cDNA in PCR-mediated analysis of mRNAs," Nucleic Acids Research, 27(21), 1999.

Sharrrocks, Andrew D., et al., "The Design of Primers for PCR", PCR Technology Current Innovations, Chapter 2, 5-11, 1994.
Shiraishi et al., "Isolation of DNA fragments associated with methylated CpG islands in human adenocarcinomas of the lung using a methylated DNA binding column and denaturing gradient gel electrophoresis," Proc. Natl. Acad. Sci. USA, 96: 2913-2918, 1999.
Shiraishi et al., "Preferential isolation of DNA fragments associated with CpG islands," Proc. Natl. Acad. Sci. USA, 92: 4229-4233, 1995.
Shiraishi et al., "The isolation of CpG islands from human chromosomal regions 11q13 and Xp22 by segregation of partly melted molecules," Nucleic Acid Res., 26: 5544-5550, 1998.
Shyamala et al., "Genome walking by single-specific-primer polymerase chain reaction: SSP-PCR," Gene, 84: 1-8, 1989.
Siebert et al., "An improved PCR method for walking in uncloned genomic DNA," Nucleic Acids Res., 23: 1087-1088, 1995.
Smith et al., "Automated differential display using a flourescently labeled universal primer," Biotechniques, 23(2): 274-279, 1997.
Smith et al., "Single primer amplification (SPA) of cDNA for microarray expression analysis," Nucleic Acids Research, 31(3): e9, 2003.
Smith, "Ligation-mediated PCR of restriction fragments from large DNA molecules," PCR Methods Appl., 2(1):21-7, 1992.
Snabes et al., "Preimplantation single-cell analysis of multiple genetic loci by whole-genome amplification," Proc. Natl. Acad. Sci. USA (Genetics), 91: 6181-6185, 1994.
Strichman-Almashanu et al., "A Genome-Wide Screen for Normally Methylated Human CpG Islands That Can Identify Novel Imprinted Genes," Genome Research, 12(4): 543-54, 2002.
Studier et al., "Relationships among Different Strains of T7 and among T7-Related Bacteriophages," 70-84, 1979.
Sutcliffe et al., "PCR amplification and analysis of yeast artificial chromosomes," Genomics, 13: 1303-1306, 1992.
Tanabe et al., "Evaluation of a Whole-Genome Amplification Method Based on Adaptor-Ligation PCR of Randomly Sheared Genomic DNA," Genes, Chromosomes & Cancer, 38:168-176, 2003.
Telenius et al., "Degenerate Oligonucleotide-Primed PCR: General Amplification of Target DNA by a Single Degenerate Primer," Genomics, 13:718-725, 1992.
Toyota et al., "Methylated CpG Island Amplification for Methylation Analysis and Cloning Differentially Methylated Sequences," Methods in Molecular Biology, 200: 101-10, 2002.
VanDevanter et al., "Pure chromosome-specific PCR libraries from single sorted chromosome," Proc. Natl. Acad. Sci. USA, 91: 5858-5862, 1994.
Vooijs et al., "Libraries for each human chromosome, constructed from sorter-enriched chromosomes by using linker-adaptor PCR," Am. J. Hum. Genet. 52: 586-597, 1993.
Wells et al., "Comprehensive chromosomal analysis of human preimplantation embryos using whole genome amplification and single cell comparative genomic hybridization," Molecular Human Reproduction, 6(11): 1055-1062, 2000.
Wells et al., "Detailed chromosomal and molecular genetic analysis of single cells by whole genome amplification and comparative genomic hybridisation," Nucleic Acids Res., 27(4): 1214-1218, 1999.
Wesley et al., "Cloning regions of the *Drosophila* genome by microdissection of polytene chromosome DNA and PCR with nonspecific primer," Nucleic Acids Res., 18(3): 599-603, 1990.
Whitcombe et al., "Detection of PCR products using self-probing amplicons and fluorescence," Nat. Biotechnol., 17: 804-807, 1999.
Wold, "Replication Protien A: A Heterotrimeric, Single-Stranded DNA-Binding Protein Required for Eukaryotic DNA Metabolism," Annu. Rev. Biochem., 61-92, 1997.
Wong et al., "Use of tagged random hexamer amplification (TRHA) to clone and sequence minute quantities of DNA-application to a 180 kb plasmid isolated from sphingmonas F199," Nucleic Acids Research,, 24: 3778-3783, (1996).
Yan et al., "Dissecting Complex Epigenetic Alterations in Breast Cancer Using CpG Island Microarrays," Cancer Res., 61: 8375-8380, 2001.

(56) References Cited

OTHER PUBLICATIONS

Zhang et al., "Whole genome amplification from a single cell: Implications for genetic analysis," Proc. Natl. Acad., 89: 5847-5851, 1992.

Zheleznaya et al., "PCR Fragmentation of DNA," Biochemistry (Moscow), 64(4): 447-453, 1999.

\* cited by examiner

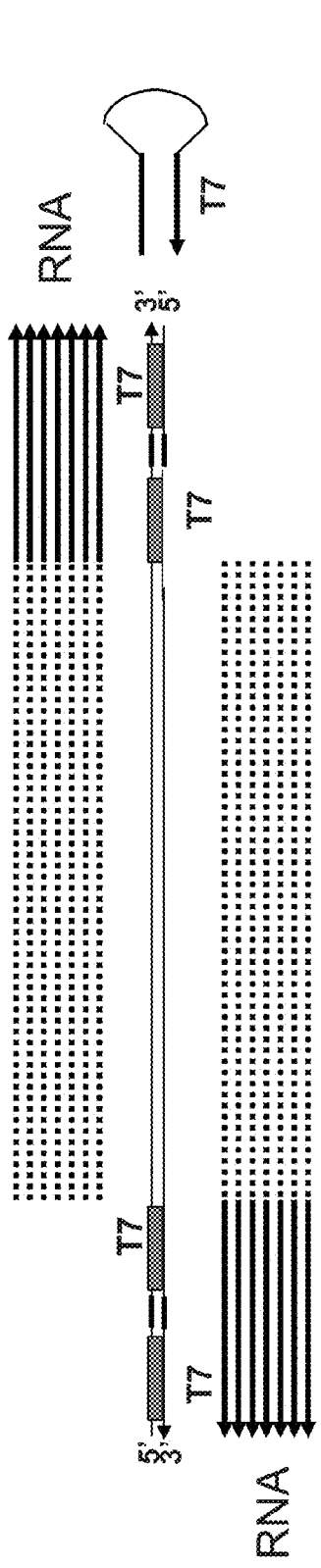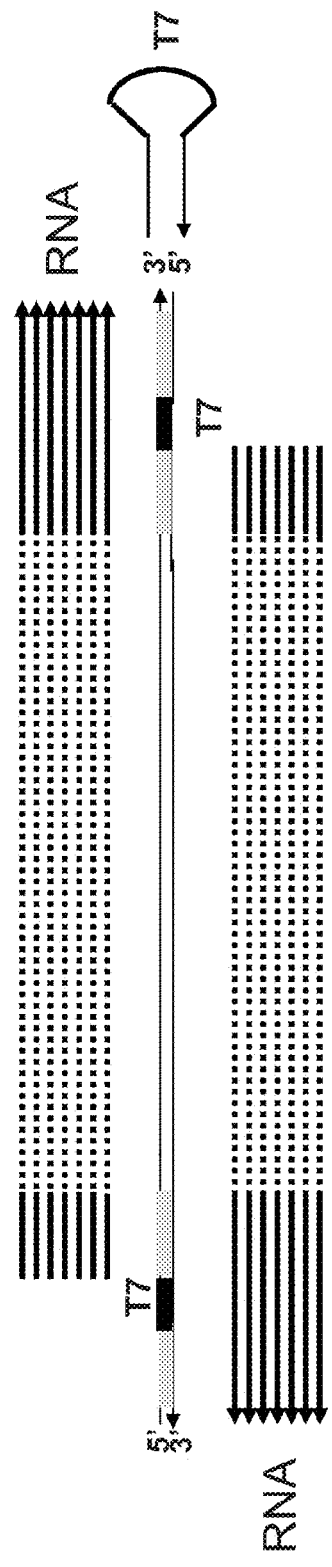
FIG. 5

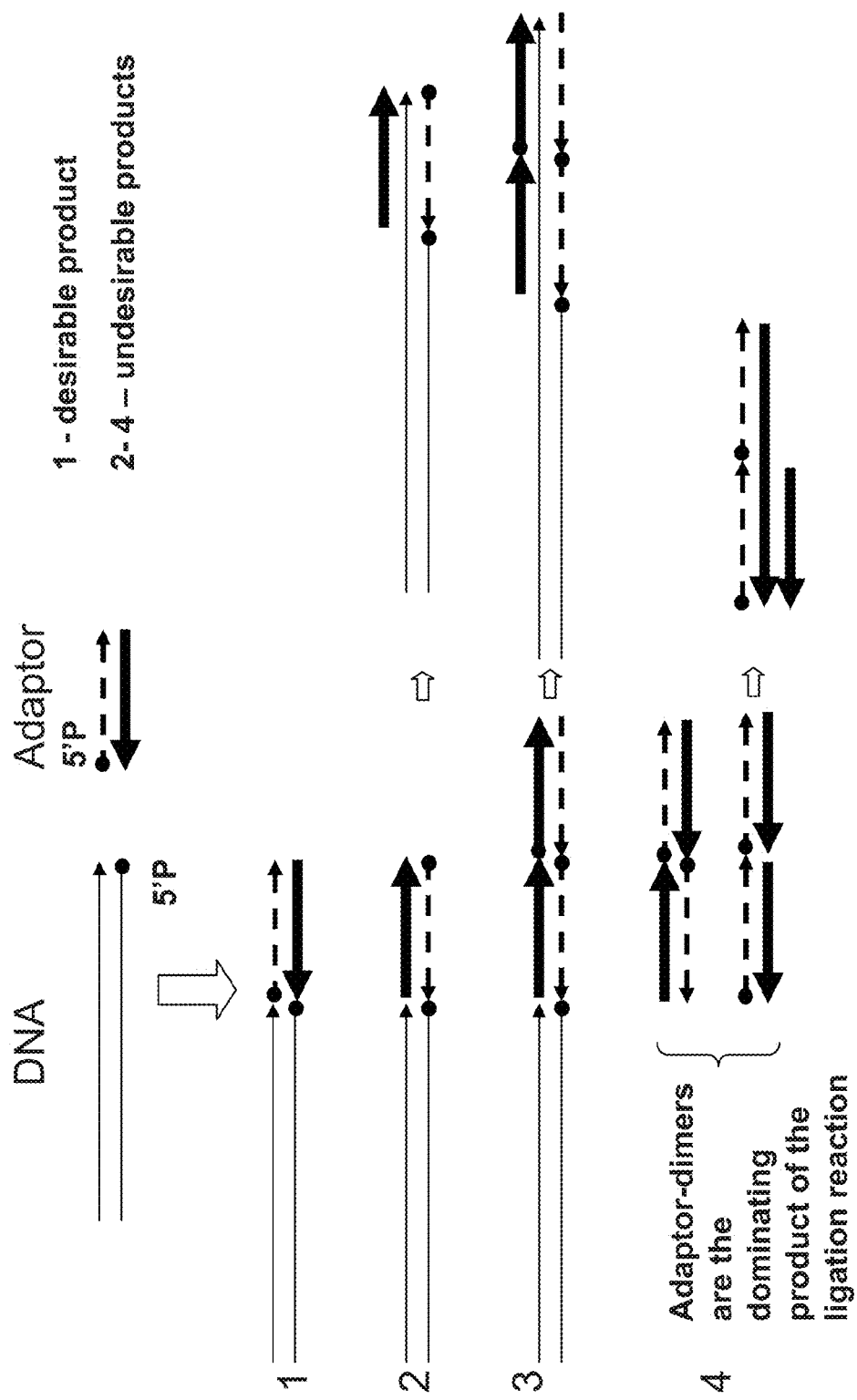

| Stem-Loop Oligo Attachment Master Mix I | Stem-Loop Oligo Attachment Master Mix II | Stem-Loop Oligo Attachment Master Mix III | Stem-Loop Oligo Attachment Master Mix IV |
|---|---|---|---|
| Stem-loop oligonucleotide<br><br>3' proofreading DNA polymerase<br><br>T4 DNA ligase<br><br>Universal Buffer<br><br>ATP<br><br>dNTPs | Stem-loop oligonucleotide with non-replicable linker (chemical)<br><br>3' proofreading DNA polymerase<br><br>T4 DNA ligase<br><br>Universal Buffer<br><br>ATP<br><br>dNTPs | Stem-loop oligonucleotide with non-replicable linker (abasic)<br><br>dU-glycosylase<br><br>3' proofreading DNA polymerase<br><br>T4 DNA ligase<br><br>Universal Buffer<br><br>ATP<br><br>dNTPs | Stem-loop oligonucleotide with cleavable site created by replication<br><br>Site-specific endonuclease<br><br>3' proofreading DNA polymerase<br><br>T4 DNA ligase<br><br>Universal Buffer<br><br>ATP<br><br>dNTPs |

FIG. 18

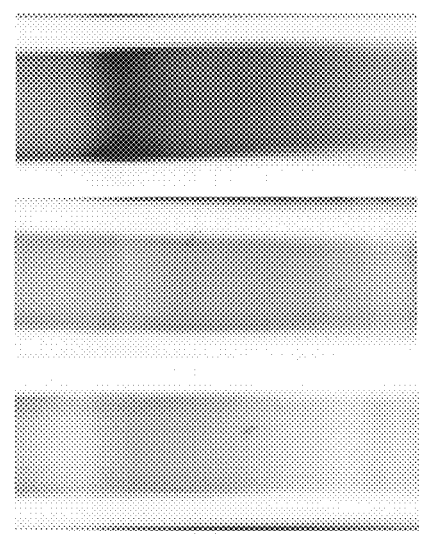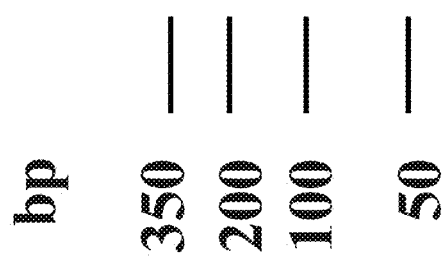
FIG. 29

METHODS FOR PROCESSING AND AMPLIFYING NUCLEIC ACIDS

The present application is a continuation of U.S. application Ser. No. 13/766,607, filed Feb. 13, 2013, now U.S. Pat. No. 8,728,737, which is a continuation of U.S. application Ser. No. 13/286,937, filed Nov. 1, 2011, now U.S. Pat. No. 8,399,199, which is a continuation of U.S. application Ser. No. 12/892,359, filed Sep. 28, 2010, now U.S. Pat. No. 8,071,312, which is a continuation of U.S. application Ser. No. 12/270,850, filed Nov. 13, 2008, now U.S. Pat. No. 7,803,550, which is a continuation of U.S. patent application Ser. No. 11/366,222, filed Mar. 2, 2006, now abandoned, which claims priority to U.S. Provisional Patent Application Ser. No. 60/704,932, filed Aug. 2, 2005. The entire contents of each of the above-referenced disclosures are specifically incorporated herein by reference.

The sequence listing that is contained in the file named "RUBCP0026USC5_ST25.txt", which is 7 KB (as measured in Microsoft Windows®) and was created on Apr. 10, 2014, is filed herewith by electronic submission and is incorporated by reference herein.

The present invention generally concerns the fields of molecular biology and cellular biology. In particular, the present invention regards preparation and amplification of molecules, optionally utilizing a novel single-step reaction.

BACKGROUND OF THE INVENTION

Enzymatic reactions that involve DNA and RNA are numerous, and they play a central role in maintenance and propagation of living cells. Since the discovery of the DNA double helix structure in 1953, researchers have found, isolated and introduced into practice a multitude of different enzymes that can, for example, cut, nick, trim, join, unwind, phosphorylate, de-phosphorylate, methylate, de-methylate, recombine, replicate, transcribe, repair, and perform many other reactions with nucleic acid molecules. These enzymes are now actively used in many areas of biology, biotechnology and medicine to clone, amplify, sequence, identify mutations, quantify gene copy number, establish expression patterns, determine DNA methylation status, etc.

Frequently the process of DNA analysis involves multiple enzymatic reactions that are performed in a sequential manner, with intermediate purification steps between the reactions. Sometimes, the reactions are multiplexed to combine in one reaction the analysis of several DNA or RNA targets, and the nucleic acid processing or analysis may involve mutiplexing of two or three enzymatic processes in one reaction. Furthermore, DNA and RNA enzymatic reactions frequently utilize synthetic nucleic acid components, such as single stranded or double stranded oligonucleotides that function as PCR or sequencing primers, ligation adaptors, or fluorescent probes, for example.

Adaptors and their Use for DNA Processing

Supplementing DNA ends with additional short polynucleotide sequences, referred to as an adaptor or linker, is used in many areas of molecular biology. The usefulness of adapted DNA molecules is illustrated by but not limited to several examples, such as ligation-mediated locus-specific PCR, ligation-mediated whole genome amplification, adaptor-mediated DNA cloning, DNA affinity tagging, DNA labeling, etc.

Ligation-Mediated Amplification of Unknown Regions Flanking Known DNA Sequence

Libraries generated by DNA fragmentation and addition of a universal adaptor to one or both DNA ends were used to amplify (by PCR) and sequence DNA regions adjacent to a previously established DNA sequence (see U.S. Pat. No. 6,777,187 and references therein, for example, all of which are incorporated by reference herein in their entirety). The adaptor can be ligated to the 5' end, the 3' end, or both strands of DNA. The adaptor can have a 3' or 5' overhang, depending on the structure of the overhang generated by restriction enzyme digestion of DNA. It can also a have blunt end, especially in the cases when DNA ends are "polished" after enzymatic, mechanical, or chemical DNA fragmentation. Ligation-mediated PCR amplification is achieved by using a locus-specific primer (or several nested primers) and a universal primer complementary to the adaptor sequence.

Ligation-Mediated Whole Genome Amplification

Libraries generated by DNA fragmentation and subsequent attachment of a universal adaptor to both DNA ends were used to amplify whole genomic DNA (whole genome amplification, or WGA) (see U.S. patent application Ser. Nos. 10/797,333 and 10/795,667 and references therein, for example, all of which are incorporated by reference herein in their entirety). The adaptor can be ligated to both strands of DNA or only to the 3' end followed by extension. The adaptor can have a 3' or 5' overhang, depending on the structure of the DNA end generated by restriction enzyme or other enzyme used to digest DNA. It can also have a blunt end, such as in the cases where DNA ends after enzymatic DNA cleavage are blunt or when the ends are repaired and "polished" after enzymatic, mechanical, or chemical DNA fragmentation. Whole genome PCR amplification is achieved by using one or two universal primers complementary to the adaptor sequence(s), in specific embodiments.

Adaptor-Mediated DNA Cloning

Adaptors (or linkers) are frequently used for DNA cloning (see Sambrook et al., 1989, for example). Ligation of double stranded adaptors to DNA fragments produced by sonication, nebulization, or hydro-shearing process followed by restriction digestion within the adaptors allows production of DNA fragments with 3' or 5' protruding ends that can be efficiently introduced into a vector sequence and cloned.

Use of Stem-Loop (Hairpin) DNA Oligonucleotides for Nucleic Acid Analysis

Stem-loop (also referred to as hairpin) oligonucleotides have been used in several applications for analysis and detection of nucleic acids. These applications include molecular beacons, stem-loop PCR primers, and stem-loop DNA probes, immobilized on microarrays (Broude, 2002).

Molecular Beacons

A molecular beacon is a single-stranded oligonucleotide probe containing a sequence complementary to the target that is flanked by self-complementary termini, and carries a fluorophore and a quencher at the 3' and 5' ends, respectively (Tyagi and Kramer, 1996). In the absence of target the fluorophore and the quencher are in a close proximity, which quenches fluorescence. Upon hybridization with the target, the beacon changes its conformation so that the fluorophore and the quencher become separated, and fluorescence increases up to 100-200 times. Molecular beacons have found many applications for real-time monitoring of PCR (Tyagi et al., 1998) and isothermal amplification (de Baar et al., 2001), as microarray-immobilized probes (Liu et al., 2000), as antisense probes for RNA detection in vivo (Sokol et al., 1998), and as a probe to measure DNA polymerase activity (Summerer and Marx, 2002) and monitor conformational changes of DNA targets (Goddard et al., 2000).

Stem-Loop (Hairpin) PCR Primers

PCR primers containing hairpin structures on their 5' ends with donor and acceptor moieties located in close proximity on the stem-loop stem have been proposed for homogeneous (a closed tube) format for amplification, real-time quantification and mismatch detection by PCR (Broude, 2002). A stem-loop primer with a fluorophore at the 5' end and a "scorpion" probe is simultaneously a molecular beacon and a PCR primer (Whitcombe et al., 1999). It has a tail attached to its 5' end by a linker that prevents copying of the 5' extension. The probe element is designed so that it hybridizes to its target only when the target site has been incorporated into the same molecule by extension of the tailed primer. It was also shown that stem-loop probes can be used as primers for PCR to reduce primer-dimer formation and mispriming, thereby increasing its specificity (Kaboev et al., 2000).

Stem-Loop Microarray Probes

Stem-loop probes can also be used as capture devices if the loop is immobilized on a surface and dangling ends are used for stacking-hybridization, thus providing both faster kinetics and higher hybrid stability (Riccelli et al., 2001). Immobilized molecular beacon probes can be used for direct detection of non-amplified target DNA and RNA molecules (Hamad-Schifferli et al., 2002).

Multiplexed Reactions that Involve DNA and RNA Molecules

Several types of multiplexed reactions that involve DNA or RNA are described to date. The multiplexed reactions can be divided into two major categories: reactions where two or more DNA/RNA sequences are amplified or detected simultaneously in one enzymatic process, and reactions where several enzymatic processes occur simultaneously with one DNA or RNA template.

Several Targets-One Enzyme

Multiplex PCR and RT-PCR are examples of the first category of multiplexed reactions (Mackay et al., 2000). In this case, several genomic or cDNA regions are amplified in one polymerase chain reaction carried out by one thermo-stable DNA polymerase. Whole genome or whole transcriptome amplification is another example of highly multiplexed DNA/RNA amplification reactions carried out by methophilic (Phi 29) or thermophylic (Taq) DNA polymerase (Sambrook et al., 1989).

One Target-Several Enzymes

"Long distance" PCR, nucleic acid sequence-based amplification (NASBA), its analog, transcription-mediated amplification (TMA), and DNA strand-displacement amplification (SDA) are examples of the second category of multiplexed DNA/RNA amplification reactions. In the "long distance" PCR method there is a mixture of Taq DNA polymerase and another thermo-stable DNA polymerase with 3' proofreading activity (Barns, 1994). TMA and NASBA methods utilize transcription-mediated amplification that involves three enzymes: T7 RNA polymerase, reverse transcriptase, and RNase H (Deiman et al., 2001). In the SDA method, two enzymes (a DNA polymerase and a restriction endonuclease) are combined in one enzymatic step to amplify DNA (Hellyer and Naolean, 2004).

DNA nick-translation method is an example of a DNA labeling reaction that involves two enzymes. The method is based on simultaneous incubation of DNA with DNase I and DNA polymerase I. DNase I generates nicks in the DNA molecule, while DNA polymerase I incorporates labeled nucleotides by initiating DNA synthesis from the nicked sites (Sambrook et al., 1989).

dU-glycosylase (which is also referred to as Uracyl-DNA Glycosylase or UDG) and endonuclease VIII can be combined to produce the enzymatic mix, or the USER enzyme for fragmentation of DNA containing dU bases (New England Biolabs; Beverly, Mass.) may be employed. The fragmentation process occurs through enzymatic generation and cleavage of abasic sites at positions of dU bases.

Several Targets-Several Enzymes

There is description of multiplexed amplification and detection of several nucleic acid sequences using three-enzyme TMA and NASBA methods (van Deursen et al., 1999).

SUMMARY OF THE INVENTION

The present invention overcomes deficiencies in the art by providing novel methods and compositions for amplification of a plurality of double stranded DNA molecules by incorporating at least one sequence onto the ends of the DNA molecules. However, the invention avoids the disadvantages of other methods, such as the generation of primer dimers in polymerase chain reaction, for example.

In particular, the present invention allows for the amplification of molecules having at least one double stranded region by using adaptors that avoid the limitations of some adaptor molecules, such as those having the propensity to form adaptor dimers. In certain aspects, the present invention provides an inert oligonucleotide for attachment to a double stranded molecule such that it renders the oligonucleotide-ligated molecule capable of being modified, such as amplified, for example by polymerase chain reaction. Upon attachment of the inert adaptor to the molecule, the attached oligonucleotide becomes active and suitable for providing at least in part one or more sequences employable for amplification, while the non-attached, free adaptor remains inactive. For example, during polymerase chain reaction the free, non-attached inert adaptor can neither be primed nor used as a PCR primer (until it is intentionally and specifically fragmented and converted into a PCR primer); during amplification by transcription the promoter sequence of the non-attached, free adaptor does not initiate RNA synthesis; during amplification by strand displacement, the nicking enzyme recognition sequence of the non-attached adaptor remains uncut.

In particular aspects, the inert adaptor comprises a stem-loop oligonucleotide, wherein the inertness of the stem-loop oligonucleotide is at least in part a result of the dormant nature of its unique structure, biochemical properties (one enzymatically active end), and/or physico-chemical characteristics (extremely high thermostability, for example). The oligonucleotide may comprise RNA, DNA, or both. The oligonucleotide may have one or more hairpins, and it may be further described as comprising any structure with multiple secondary structure and only one end. In specific embodiments, the oligonucleotide can change its functionality upon attachment to a double stranded nucleic acid molecule (DNA, RNA, or both). In other words, because of a conformational change of the oligonucleotide upon (such as following, for example) attachment to a double stranded nucleic acid molecule, one or more functional properties of the oligonucleotide become altered, such as one or more functional properties hidden in the oligonucleotide prior to attachment manifesting upon attachment.

In addition to the advantages provided by the adaptors of the invention, the invention further provides novel conditions for modification of DNA molecules with the adaptors, and subsequent amplification. In most cases in the art, the process of DNA analysis involves multiple enzymatic reactions that are performed in a sequential manner, frequently with intermediate purification steps between at least some of the reactions. For example, preparation of DNA libraries for subsequent amplification and analysis involves ligation of adaptor sequences to DNA ends to introduce a priming site for the PCR-mediated whole genome amplification and ligation-mediated PCR, a promoter element for the transcription-mediated DNA amplification, and/or cohesive ends to facilitate DNA integration into a vector molecule for cloning. Preparation of library from genomic or viral DNA by current adaptor attachment procedures typically occur in 6 steps (FIG. 1A):

Step 1—fragmentation of high molecular weight (HMW) DNA to a size amenable to amplification or cloning;

Step 2—DNA purification to remove nucleases and other reagents;

Step 3—"polishing" of DNA ends by a 3' proofreading DNA polymerase(s) to generate blunt-ended DNA fragments with the 3' hydroxyl and 5' phosphate groups at the termini;

Step 4—DNA purification to remove the polymerase and replace the buffer, or, alternatively, heat inactivation of the DNA polymerase;

Step 5—adaptor ligation; and

Step 6—3' end extension (in the case when an adaptor is ligated only to one strand of DNA, specifically to the 5' phosphate).

However, such a multi-step process takes a considerable amount of time (1-2 days) and can be a major obstacle for high throughput and diagnostic-type applications, for example. The process becomes more complicated when library preparation involves additional enzymatic steps, such as DNA or library digestion with methylation-sensitive or methylation-specific endonucleases (for example, in the preparation of Methylome libraries, such as are described in U.S. patent application Ser. No. 11/071,864, filed Mar. 3, 2005, which is incorporated by reference herein in its entirety), or restriction nuclease cleavage within the adaptor sequence to produce sticky ends for DNA cloning.

The present invention satisfies a long-felt need in the art for obviating the requirement for multiple manipulations for nucleic acid processing. The current invention introduces and demonstrates new methods and compositions that allow reduction of several important multi-step enzymatic DNA processes to a single-step-reaction that is performed in one reaction volume (FIGS. 1B and 1C). Such simplification has been achieved by developing a highly multiplexed enzymatic method (Enz-O-Mix) that combines a substantial number (from 2 to 10) of enzymatic processes into one complex reaction mixture that occurs under universal buffer conditions.

Specifically, the current invention introduces novel processes of DNA library preparation and/or DNA amplification (FIG. 1C) that reduce the whole multi-step process to a single-step multiplexed enzymatic reaction involving as a minimum two Enzymes, a stem-loop (hairpin) Oligonucleotide with a special base/bonds composition, and a universal buffer (Mix), which is herein referred to as Enz-O-Mix, that supports efficient functioning of all enzymatic activities present in the mixture. The invention demonstrates that the Enz-O-Mix approach can be used to prepare a DNA library for whole genome amplification (WGA Library), a Methylome library for amplification and analysis of methylated DNA regions, and/or even directly amplify DNA in a single multi-enzyme reaction, for example.

The Enz-O-Mix library/amplification has no limitations on the size and nature of DNA in the reaction. The method can be applied to high molecular weight DNA, such as is isolated from tissues or cell culture, for example, as well as highly degraded DNA, such as cell-free DNA from blood and urine and/or DNA extracted from formalin-fixed, paraffin-embedded tissues, for example.

The applications of the Enz-O-Mix method are numerous. The Enz-O-Mix method is easy to automate and use in clinical diagnostic and point-of-care applications, for example. In specific embodiments, different enzyme combinations are utilized for many novel kits and assays and utilized in such areas as biotechnology, the pharmaceutical industry, molecular diagnostics, forensics, pathology, biodefense, and/or bio-computing, for example. The Enz-O-Mix approach is a simple and cost-effective alternative to the "lab-on-a chip" microfluidic approach that is currently attempting to solve the same problem (multi-step DNA processing) by reduction of reaction volumes and integration of multiple reactions into a small format (FIG. 2). The method can be used for in vitro as well as for in vivo nucleic acid amplification and/or detection.

In specific aspects, the present invention introduces a concept of multiplexing two or more enzymatic processes in one reaction, teaches how to optimize a highly multiplexed enzymatic process, and demonstrates in multiple specific examples the efficacy of this approach. In particular embodiments, the present invention is directed to compositions and methods for simultaneous processing of DNA molecules with a combination of enzymes in a one-step-one-tube reaction and producing either a collection of molecules suitable for amplification, or amplified DNA molecules.

In particular, the present invention greatly reduces the number of steps for library preparation by consolidating a series of steps into one step. For known whole genome amplification or whole methylome methods, these protocols greatly reduce the number of steps for library syntheses that utilize adaptors. That is, in the case of WGA library preparation from high molecular weight DNA, for example, the number of steps is reduced from about 6 to 1 (FIGS. 1A and 1B). In the case of WMA library preparation from high molecular weight DNA, for example, the number of steps is reduced from about 7 to 1. In the case of WGA library preparation from fragmented DNA (plasma, serum, or urine, for example), the number of steps is reduced from about 4 to 1 (FIG. 1B). In the case of Methylome library preparation from fragmented DNA, for example, the number of steps is reduced from about 5 to 1 (FIG. 1B).

In particular embodiments, the methods of the invention can be easily applied to any type of fragmented double stranded DNA including but not limited to, for example, free DNA isolated from plasma, serum, and/or urine; apoptotic DNA from cells and/or tissues; DNA fragmented enzymatically in vitro (for example, by DNase I and/or restriction endonuclease); and/or DNA fragmented by mechanical forces (hydro-shear, sonication, nebulization, etc.).

In other embodiments, the invention can be easily applied to any high molecular weight double stranded DNA including, for example, DNA isolated from tissues, cell culture, bodily fluids, animal tissue, plant, bacteria, fungi, viruses, etc.

In one embodiment of the invention, there is incubation of DNA with an enzymatic mixture (Enz-O-Mix) comprising from about 2 to about 18 different enzymes in one buffer and a stem-loop (hairpin) oligonucleotide with a specific base/bonds composition.

In particular embodiments, there is a one-step enzymatic process including one or more of the following: a) "polishing" of DNA and stem-loop oligonucleotide ends by Klenow fragment of DNA polymerase I (or other proofreading DNA polymerase); b) ligation of the 3' end of stem-loop oligonucleotide to the 5' end of DNA, such as by a ligase, for example, by T4 DNA ligase; c) "fill-in" DNA synthesis that is initiated at the 3' end of DNA, propagates towards the end of the stem-loop oligonucleotide, and stops at a replication block or at the end of the oligonucleotide; and d) cleavage in the middle of a generated inverted repeat by a restriction nuclease; and e) restriction cleavage with a mixture of methylation-sensitive restriction enzymes or methylation-specific nuclease(s) (such as in embodiments concerning whole methylome amplification library), for example.

In particular aspects of the invention, an inverted repeat (palindrome) at the end of DNA molecules is not generated (or is generated and removed), because it may inhibit the amplification step (PCR), priming of the cDNA strand synthesis (amplification by transcription), or priming of the second DNA strand synthesis (amplification by strand displacement DNA synthesis). Thus, in specific embodiments at least part of the oligonucleotide sequence is eliminated, such as, by termination of replication in the middle of a stem-loop oligonucleotide or by cutting the generated inverted repeat internally, for example.

In one specific embodiment of this invention, a chemical modification, such as hexaethylene glycol (HEG) linker, a bulky base analog, or one or several abasic sites within the loop or adjacent to it, can be introduced during oligonucleotide synthesis. Such modifications will terminate the replication within the stem-loop oligonucleotide.

In another specific embodiment, the replication block is generated during the reaction by incorporating one or more dU bases into the stem-loop oligonucleotide design and including dU-glycosylase (which is also referred to as Uracyl-DNA Glycosylase or UDG) in the reaction mix.

In some embodiments, a specific site for a cleavage enzyme is generated during "fill-in" DNA synthesis that is initiated at the 3' end of the DNA, propagates towards the end of the stem-loop oligonucleotide, and stops at the 5' end of the oligonucleotide. Such a site resides originally either completely or partially within the single-stranded loop of an oligonucleotide and becomes functional (cleavable) only after conversion of this loop into double-stranded form.

In one specific embodiment a cleavage enzyme is represented by a restriction endonuclease, in another by a homing endonuclease.

In some embodiments, the methods further comprise simultaneous digestion with an endonuclease or combination of endonucleases, such as restriction endonucleases, DNase I, benzonase, methylation-specific nuclease McrBC, apoptotic endonucleases, etc., to generate in one step Whole Genome or Whole Methylome library even from high molecular weight (HMW) DNA.

In particular embodiments, a library generated by a one-step process is further amplified by PCR using universal primer complementary to the sequence introduced by attachment of a stem-loop oligonucleotide.

In particular embodiments, library generation and PCR amplification are combined into one integrated, closed-tube process in a thermocycler.

In one particular embodiment, an integrated, closed-tube library preparation/amplification process is supported by a universal PCR primer included in the original Enz-O-Mix.

In another particular embodiment, an integrated, closed-tube library preparation/amplification process is supported by a stem-loop oligonucleotide converted into a functional universal primer as a result of enzymatic and chemical reactions that occur before PCR amplification.

In another embodiment, degradable stem-loop oligonucleotides are used as locus-specific primers for a hot start PCR process.

In another particular embodiment, a library generated by one-step process is further amplified by transcription utilizing a promoter sequence (T7, T3, SP6, etc.) introduced by attachment of a stem-loop oligonucleotide.

In particular embodiments, a stem-loop oligonucleotide design is employed for the one-step library synthesis reaction, although in alternative embodiments other adaptors may be utilized, such as a standard linear two-oligonucleotide adaptor, for example.

In particular embodiments, a stem-loop oligonucleotide provides a synthesized library with a new function that was present neither in the DNA molecule nor in the stem-loop oligonucleotide prior to its attachment. Examples include a functionally inactive T7 promoter sequence, a non-cleavable restriction site, and/or inactive nicking site residing at least partially within the loop or stem region of the stem-loop oligonucleotide and activated only by the attachment process and conversion of the single stranded loop into a double stranded molecule.

In particular embodiments, a stem-loop oligonucleotide provides a synthesized library with a 5' overhang that was not present either in the DNA molecule or in the stem-loop oligonucleotide prior to its attachment, and that can be used for covalent or non-covalent immobilization of a synthesized library on a solid support via hybridization or hybridization and ligation to a covalently attached oligonucleotide.

In a specific embodiment, the library synthesis and its immobilization within the tube (well) occurs simultaneously in a one Enz-O-Mix process. In this case, combinations of enzymes and stem-loop oliginucleotides are mixed together in a special tube with a covalently attached capture oligonucleotide to produce Enz-O-Mix-Immobilization kits for high throughput DNA processing and diagnostic applications in solid phase format.

In particular embodiments, combinations of enzymes and stem-loop oligonucleotides are mixed together to produce Enz-O-Mix kits for high throughput DNA processing and diagnostic applications. In particular embodiments, there is a Universal Enz-O-Mix Buffer that provides simultaneous activity of all enzymes used in the reaction.

In particular embodiments, combinations of enzymes and stem-loop oligonucleotides are mixed together to produce integrated, closed-tube Enz-O-Mix kits for high throughput DNA fragmentation, amplification and labeling. In particular embodiments, there is a Universal Enz-O-Mix Buffer that supports simultaneous activities of all enzymes used in the reaction.

In a specific embodiment, there is a process for optimization of the Universal Buffer and other components of the multiplexed enzymatic reaction.

In particular aspects, the present invention is directed to a system and method for preparing a collection of molecules, particularly molecules suitable for amplification, such as amplification utilizing known sequences on the molecules. In specific embodiments, the oligonucleotide comprises a known sequence.

In an additional embodiment, there is a kit housed in a suitable container that comprises one or more compositions of the invention and/or comprises one or more compositions suitable for at least one method of the invention.

In one embodiment of the invention, there is a method of preparing a nucleic acid molecule, comprising: providing a double stranded nucleic acid molecule; and attaching one strand of a stem-loop oligonucleotide comprising an inverted repeat and a loop to the double stranded nucleic acid molecule to produce an oligonucleotide-attached nucleic acid molecule. The double stranded nucleic acid molecule may be a double stranded DNA molecule, in some embodiments. In specific embodiments, the attaching is further defined as attaching the oligonucleotide to the double stranded nucleic acid molecule under conditions to produce a non-covalent junction, such as a nick, a gap, or a 5' flap structure, in the oligonucleotide-attached nucleic acid molecule. In particular aspects of the invention, the attaching is further defined as ligating. The method may further comprise displacing one strand of the oligonucleotide from the oligonucleotide-attached nucleic acid molecule by strand displacement or by nick translation polymerization. In a specific embodiment, at least part of the oligonucleotide-attached nucleic acid molecule is amplified, such as by polymerase chain reaction, RNA transcription, or strand displacement, for example. Methods of the invention may further comprise amplifying an oligonucleotide-attached nucleic acid molecule, wherein at least part of the inverted repeat is excluded from the amplified oligonucleotide-attached nucleic acid molecule.

Ligating embodiments may be further defined as comprising: generating ligatable ends on the double stranded nucleic acid molecule; generating a ligatable end on the stem-loop oligonucleotide; and ligating one strand of the ligatable end of the stem-loop oligonucleotide to one strand of an end of the nucleic acid molecule, thereby generating a non-covalent junction, such as a nick, a gap, or a 5' flap structure, in the oligonucleotide-attached nucleic acid molecule. In further aspects, the methods comprise generating blunt ends on the nucleic acid molecule; generating a blunt end on the stem-loop oligonucleotide; and ligating one strand of the blunt end of the stem-loop oligonucleotide to one strand of a blunt end of the nucleic acid molecule, thereby generating a nick in the oligonucleotide-ligated nucleic acid molecule.

In specific aspect of the invention, the stem-loop oligonucleotide comprises a known sequence, for example a regulatory sequence, including a RNA polymerase promoter sequence. A regulatory sequence may reside at least in part within the stem of the stem-loop oligonucleotide, within the loop of the stem-loop oligonucleotide, or both.

Methods of the invention may further comprise digesting the DNA molecule with one or more endonucleases to produce DNA fragments; producing blunt ends on the DNA fragments; producing a blunt end on the stem-loop oligonucleotide; and ligating one strand of the blunt end of a stem-loop oligonucleotide to one strand of a blunt end of a DNA fragment, thereby generating a nick in an oligonucleotide-ligated DNA fragment. In a specific embodiment, the endonuclease is a restriction endonuclease, DNAse I, or an apoptotic endonuclease, or a mixture thereof. In particular embodiments, the restriction endonuclease is methylation-specific or methylation-sensitive.

In additional embodiments, the oligonucleotide-attached nucleic acid molecule comprises a nick having a 3' hydroxy group, wherein there is polymerization from the 3' hydroxy group of at least part of the oligonucleotide-attached nucleic acid molecule.

Strand displacement or nick translation polymerization may be further defined as polymerization that ceases at a non-replicable base or region in the loop or in a region of the stem adjacent to the loop.

In a specific aspect of the invention, the method further comprises the step of digesting the double stranded DNA molecule with an endonuclease to generate DNA fragments, wherein the oligonucleotide becomes ligated to one strand of the DNA fragment and wherein polymerization of an oligonucleotide-ligated DNA fragment excludes at least part of the inverted repeat by subjecting the oligonucleotide-ligated DNA fragment to strand displacement or nick translation polymerization that halts at a base or sequence in the loop or in a region of the stem adjacent to the loop.

In some embodiments, the stem-loop oligonucleotide is further defined as comprising a non-replicable base or sequence. In particular, in some cases at least part of the non-replicable base or sequence is present in the loop of the oligonucleotide or in a sequence of the stem adjacent to the loop. The non-replicable base or sequence may comprise an abasic site or sequence, hexaethylene glycol, and/or a bulky chemical moiety attached to the sugar-phosphate backbone or the base. In specific embodiments, the abasic site or sequence is introduced by one or more enzymes in the single solution. In a further specific embodiment, the loop of the stem-loop oligonucleotide comprises at least one deoxyuridine.

In one particular embodiment, strand displacement or nick translation polymerization of the oligonucleotide-attached nucleic acid molecule generates an endonuclease site. In particular aspects, the methods further comprise the step of digesting the double stranded DNA molecule with an endonuclease to generate DNA fragments, wherein the oligonucleotide becomes blunt end ligated to one strand of the DNA fragment to produce an oligonucleotide-ligated DNA fragment, and wherein strand displacement or nick translation polymerization of the oligonucleotide-ligated DNA fragment generates an endonuclease site.

In particular aspects, the endonuclease site is a site-specific restriction endonuclease site and at least part of the inverted repeat is removed by cleavage with said restriction endonuclease. The endonuclease site may reside within the stem and/or loop regions. Examples of endonucleases include Eco NI or PacI. The endonuclease site may be a homing endonuclease site, such as I-Ceu I, I-Sce I, PI-Psp I, or PI-Sce I. In specific embodiments, RNA transcription is initiated from the regulatory sequence, thereby producing at least one transcribed polynucleotide.

In specific embodiments, a regulatory sequence resides at least in part within the stem of the stem-loop oligonucleotide, or at least in part within the loop of the stem-loop oligonucleotide. In a specific aspect, the regulatory sequence comprises a bacteriophage regulatory sequence, such as a T7 regulatory sequence, a T3 regulatory sequence, or a Sp6 regulatory sequence, for example. In specific aspects, a transcribed polynucleotide is replicated by a reverse transcriptase, which may be initiated by hybridization of the oligonucleotide complementary to the 3' end of the transcribed polynucleotide.

The stem-loop oligonucleotide may further comprise a recognition sequence for a nicking endonuclease and the oligonucleotide-attached nucleic acid molecule is amplified by strand displacement synthesis and second strand synthesis, in particular aspects of the invention. In a specific aspect, the recognition sequence for a nicking endonuclease resides at least in part within the stem of the stem-loop oligonucleotide. The recognition sequence for a nicking endonuclease may reside at least in part within the loop of the stem-loop oligonucleotide. In specific embodiments, the nicking endonuclease is N.Alw I, N.Bbv CIA, N.Bbv CIB, Nb.Bpu10I, Nb.BsmI, N.BstNBI, or N.Bst 9I.

In specific aspects, a 5' end of the stem-loop oligonucleotide lacks a phosphate.

In particular embodiments, the oligonucleotide-attached nucleic acid molecule is further modified, such as by cloning, including by incorporation of the modified molecule into a vector, said incorporation occurring at ends in the modified molecule generated by endonuclease cleavage within the inverted repeat.

In additional embodiments of the invention, methods of the invention occur in a single suitable solution, wherein the process occurs in the absence of exogenous manipulation. The method may occur at one temperature, such as from about 10° C. to about 75° C. In particular embodiments, the solution comprises one or more of the following: ligase; DNA polymerase; one or more endonucleases; RNA polymerase; reverse transcriptase; RNase H; deoxy-uridine glycosylase (which is also referred to as Uracyl-DNA Glycosylase or UDG); nickase; thermophilic DNA polymerase; ATP; rNTPs; and dNTPs.

In one aspect of the invention, there is a kit, housed in a suitable container, comprising: a stem-loop oligonucleotide; and a solution suitable for ligation of the oligonucleotide onto a double stranded molecule; and, optionally, one or more of the following: ligase; DNA polymerase one or more restriction enzymes; RNA polymerase; reverse transcriptase; RNase H; nickase; thermophilic DNA polymerase; ATP; rNTPs; and dNTPs. In specific embodiments, the oligonucleotide of the kit comprises a RNA polymerase promoter sequence, such as a T7 RNA polymerase promoter sequence, for example. The one or more endonucleases may be methylation-specific, methylation-sensitive, or may be a homing endonuclease.

In specific embodiments, methods of the invention occur in a single suitable solution, wherein the process of preparing and amplifying of a oligonucleotide-attached nucleic acid molecule occurs in the absence of exogenous manipulation. The method may be further defined as occurring at one temperature, such as between about 10° C. to about 85° C. or between about 10° C. to about 85° C. In specific embodiments, the method is further defined as occurring at least two different temperatures, such as wherein at least one of the temperatures is from about 10° C. to about 100° C.

In specific embodiments, the oligonucleotide-attached nucleic acid molecule is immobilized to a solid support, such as non-covalently or covalently.

Some methods of the invention further comprise the step of digesting the DNA molecule with an endonuclease to generate DNA fragments, wherein the oligonucleotide becomes attached to one strand of the DNA fragment, wherein strand displacement polymerization of the oligonucleotide-ligated DNA fragment and its arrest at a base or sequence in the loop or in a region of the stem adjacent to the loop generates a 5' overhang, and wherein the single stranded 5' overhang hybridizes to a complementary oligonucleotide covalently immobilized to a solid support.

Additional embodiments of the invention include a library of DNA molecules prepared by the methods of the invention.

In some embodiments of the invention, there is a method of preparing a DNA molecule, comprising: providing an oligonucleotide; and mixing the oligonucleotide with a double stranded DNA molecule, such that upon attachment of the oligonucleotide to the double stranded DNA molecule, the oligonucleotide attached to the DNA molecule is capable of demonstrating a function that it was incapable of before the attachment to the double stranded DNA molecule, thereby producing an oligonucleotide-attached DNA molecule suitable for modification. In specific aspects, the method occurs in a single suitable solution, wherein the process occurs in the absence of exogenous manipulation. Exemplary modifications include site-specific nicking, site-specific double-strand cleavage, transcription, recombination, amplification, polymerization, nick translation, strand displacement, immobilization or a combination thereof.

In an additional embodiment of the invention, there is a composition comprising a stem-loop oligonucleotide, said oligonucleotide comprising an inverted repeat, a loop and at least one thermo-sensitive site or site capable of becoming a thermo-sensitive site, wherein the oligonucleotide is capable of producing a suitable primer upon exposure to heat. In additional embodiments, the composition further comprises a repair enzyme, such as one capable of converting damaged bases into an abasic site. Examples of DNA repair enzymes include a DNA glycosylase, such as dU-glycosylase, for example. In a specific aspect, the thermo-sensitive site is an abasic site, such as an apyrimidine site or an apurine site, for example. In an additional specific embodiment, the site capable of becoming a thermo-sensitive site is further defined as a base that can be enzymatically converted to a thermo-sensitive site. The base that can be enzymatically converted to a thermo-sensitive site may be deoxy-uridine and the enzyme may be dU-glycosylase (which is also referred to as Uracyl-DNA Glycosylase or UDG). In a specific aspect, the thermo-sensitive site is introduced into the oligonucleotide during synthesis, such as chemical synthesis. The composition may be capable of comprising a breakage of a strand of the oligonucleotide at one or more deoxy-uridine bases upon exposure to heat. The thermosensitive site or site capable of becoming a thermo-sensitive site may be located in the stem, in the loop, or both. The oligonucleotide may be blunt ended or have a 5' overhang.

In an additional embodiment, there is a method of producing a primer, comprising providing a composition of the invention and subjecting the composition to heat such that the primer is produced. In a specific aspect, the composition further comprises a DNA repair enzyme and the subjecting to heat is further defined as subjecting to two or more exposures of heat. One exposure to heat may comprise about 37° C. and another exposure to heat may comprise about 95° C. One exposure to heat may comprise about 10° C. to about 100° C. whereas another exposure to heat may comprise about 80° C. to about 100° C. The method may further comprise amplification of a DNA molecule utilizing said composition.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features that are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawings.

FIGS. 5A-5B are schematic descriptions of the amplification of a library of DNA fragments with inverted repeat sequences at their ends by RNA transcription. Promoter sequence can be added to a DNA end either as a part of the oligonucleotide stem-region (A), or as a part of the oligonucleotide loop region (B). The products of the amplification are RNA molecules in this embodiment.

FIG. 11A shows a standard adaptor formed by two different oligonucleotides, wherein one of them has a 5' phosphate group, and possible products formed when such adaptor is used in the multi-enzyme one-step ligation process.

FIG. 18 shows composition of five exemplary different Stem-Loop Oligo Attachment Master Mixes of the invention that are used for the one-step nucleic acid library synthesis.

In FIG. 24A, there is PCR using STS #4 primers. In FIG. 24B, there is PCR using STS #19 primers. In FIG. 24C, there is PCR using STS #35 primers (Table II). Results show little or no representational bias for all 3 STS sequences.

FIG. 29 shows the products of simultaneous library synthesis and isothermal amplification of cell-free urine DNA using the nicking activity of the nuclease N.BbvC IB and strand displacement DNA synthesis.

FIG. 30A shows a 2-step, opened-tube protocol. In this case, Enz-O-Mix library synthesis/amplification is performed in two operational steps: step 1—a tube containing DNA is supplemented with the library (WGA or WMA) synthesis reagents and incubated at 37° C. for 1 h, and step 2—the tube is opened, supplemented with PCR amplification buffer/reagents and subjected to temperature cycling. FIG. 30B shows a 1-step, closed-tube protocol. In this case, Enz-O-Mix library synthesis/amplification is performed in one operational step when a tube containing DNA is supplemented with the library synthesis/amplification (PCR) reagents and universal buffer, and subjected to programmed temperature conditions within a thermocycler.

In FIG. 35A, there is non-covalent library immobilization by hybridization of the exposed 5' stem region to an oligo S covalently attached to a tube/well surface. In FIG. 35B, there is a covalent library immobilization by hybridization and ligation of the exposed 5' stem region to an oligo S covalently attached to a tube/well surface.

DETAILED DESCRIPTION OF THE INVENTION

Figure 1A:
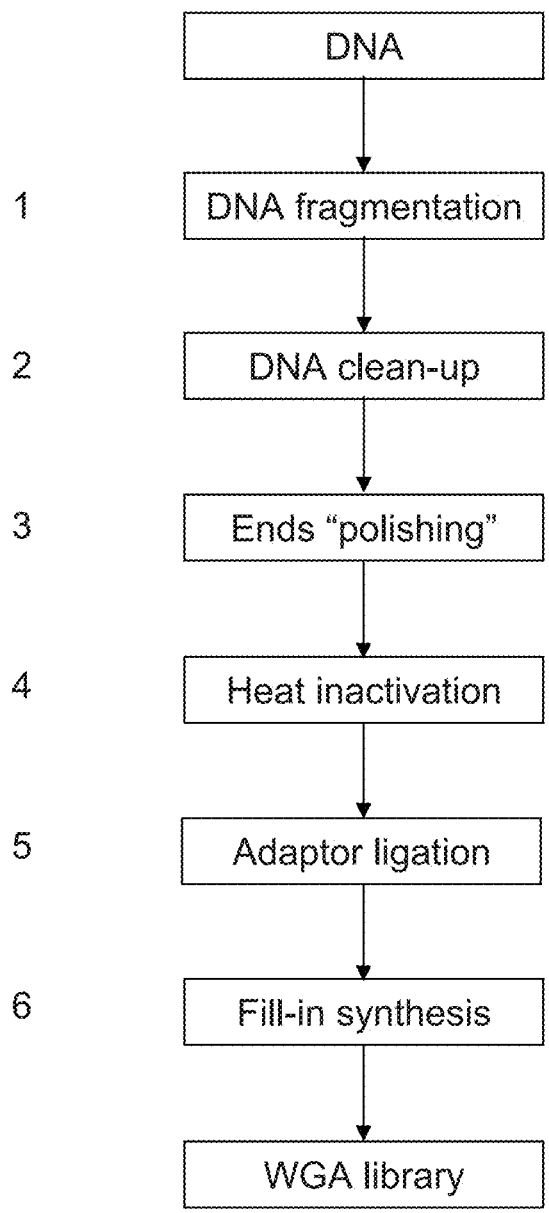
FIG. 1A shows a standard multi-step DNA adaptor attachment process.
Figure 1B:
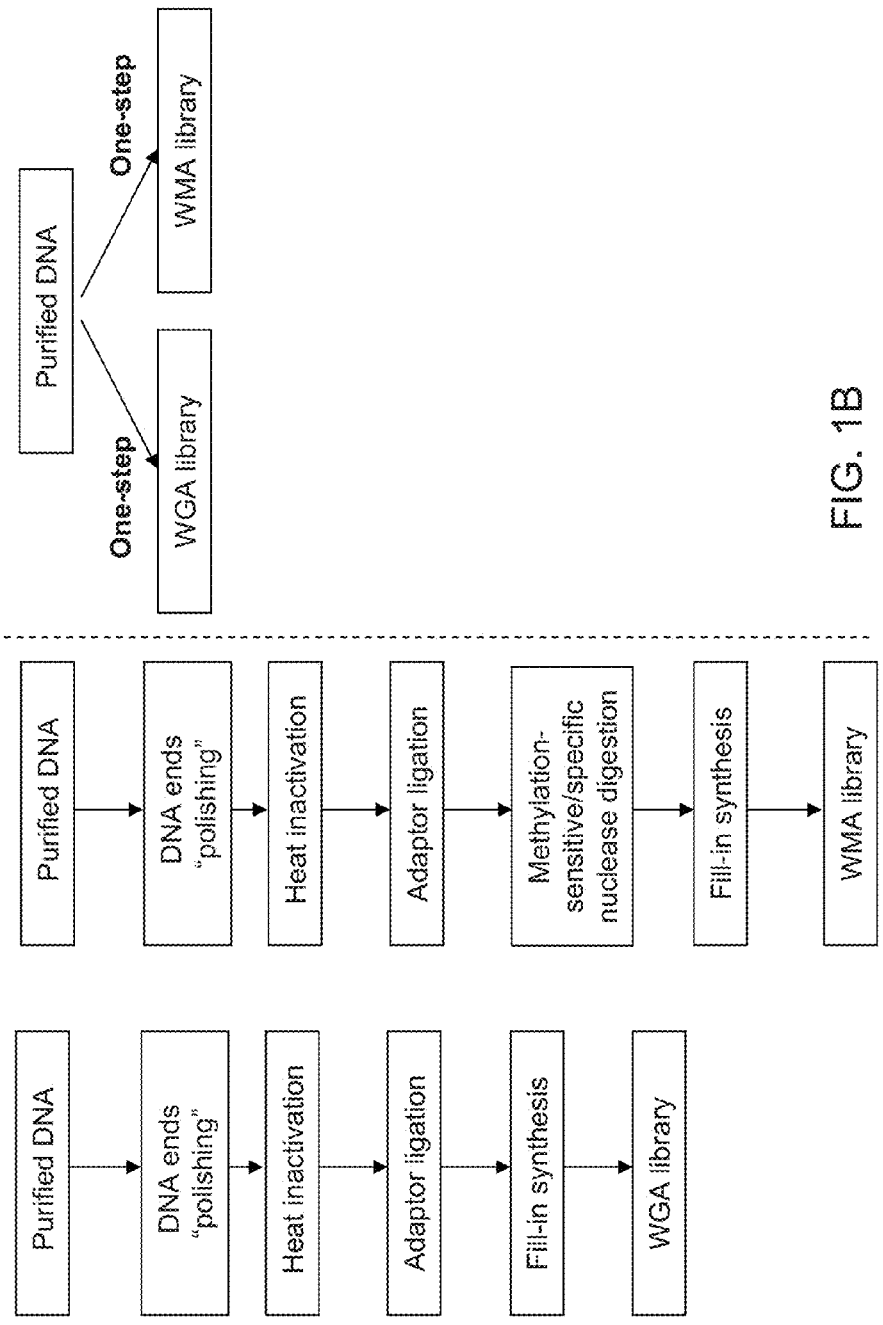
FIG. 1B compares preparation processes for WGA and WMA libraries from degraded serum and urine DNA described in the present invention and in previously filed patent applications (U.S. patent application Ser. No. 11/071,864, filed Mar. 3, 2005).
Figure 1C:
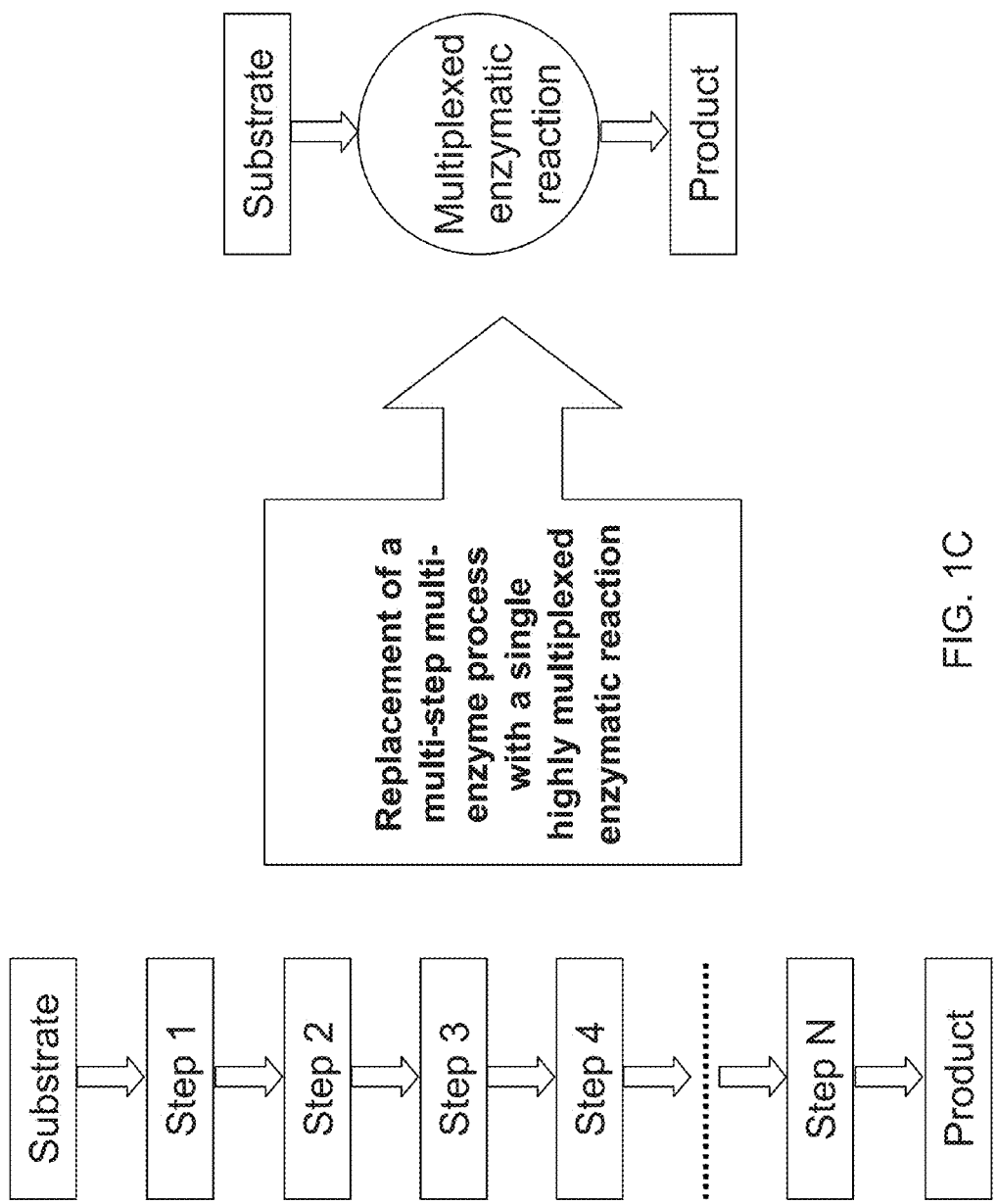
FIG. 1C is a general representation of the invention that can be described as a reduction of several important multi-step enzymatic DNA processes to a single-step multiplexed enzymatic reaction that is performed in one reaction volume (Enz-O-Mix Method).
Figure 2:
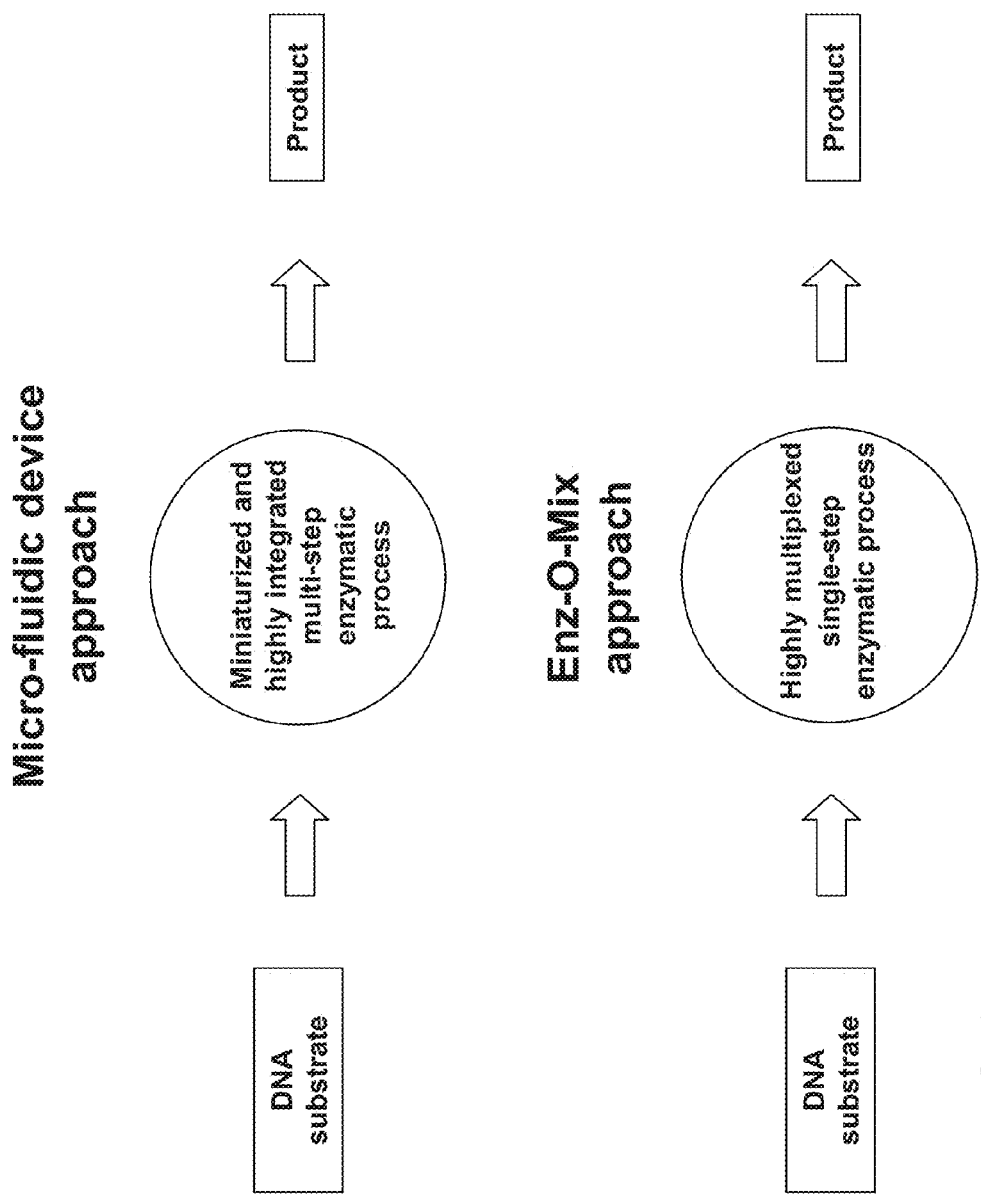
FIG. 2 shows that the Enz-O-Mix approach can be viewed as a simple and cost-effective alternative to the "lab-on-a chip" microfluidic approach that is currently attempting to solve the same problem by reduction of reaction volumes and integration of multiple reactions into a small format.

The present application incorporates by reference herein in its entirety U.S. patent application Ser. No. 11/071,864, filed Mar. 3, 2005. Also incorporated by reference herein in its entirety is U.S. patent application Ser. No. 11/367,046, filed Mar. 2, 2006, entitled "Isolation of CpG Islands by Thermal Segregation and Enzymatic Selection-Amplification Method," which itself claims priority to U.S. Provisional Patent Application Ser. No. 60/704,541, filed Aug. 2, 2005.

I. Definitions

In keeping with long-standing patent law convention, the words "a" and "an" when used in the present specification in concert with the word comprising, including the claims, denote "one or more." Some embodiments of the invention may consist of or consist essentially of one or more elements, method steps, and/or methods of the invention. It is contemplated that any method or composition described herein can be implemented with respect to any other method or composition described herein.

The practice of the present invention will employ, unless otherwise indicated, conventional techniques of molecular biology, microbiology, recombinant DNA, and so forth which are within the skill of the art. Such techniques are explained fully in the literature. See e.g., Sambrook, Fritsch, and Maniatis, MOLECULAR CLONING: A LABORATORY MANUAL, Second Edition (1989), OLIGONUCLEOTIDE SYNTHESIS (M. J. Gait Ed., 1984), ANIMAL CELL CULTURE (R. I. Freshney, Ed., 1987), the series METHODS IN ENZYMOLOGY (Academic Press, Inc.); GENE TRANSFER VECTORS FOR MAMMALIAN CELLS (J. M. Miller and M. P. Calos eds. 1987), HANDBOOK OF EXPERIMENTAL IMMUNOLOGY, (D. M. Weir and C. C. Blackwell, Eds.), CURRENT PROTOCOLS IN MOLECULAR BIOLOGY (F. M. Ausubel, R. Brent, R. E. Kingston, D. D. Moore, J. G. Siedman, J. A. Smith, and K. Struhl, eds., 1987), CURRENT PROTOCOLS IN IMMUNOLOGY (J. E. Coligan, A. M. Kruisbeek, D. H. Margulies, E. M. Shevach and W. Strober, eds., 1991); ANNUAL REVIEW OF IMMUNOLOGY; as well as monographs in journals such as ADVANCES IN IMMUNOLOGY. All patents, patent applications, and publications mentioned herein, both supra and infra, are hereby incorporated herein by reference.

A skilled artisan recognizes that there is a conventional single letter code in the art to represent a selection of nucleotides for a particular nucleotide site. For example, R refers to A or G; Y refers to C or T; M refers to A or C; K refers to G or T; S refers to C or G; W refers to A or T; H refers to A or C or T; B refers to C or G or T; V refers to A or C or G; D refers to A or G or T; and N refers to A or C or G or T.

The term "blunt end" as used herein refers to the end of a dsDNA molecule having 5' and 3' ends, wherein the 5' and 3' ends terminate at the same nucleotide position. Thus, the blunt end comprises no 5' or 3' overhang.

The term "double stranded molecule" as used herein refers to a molecule that is double stranded at least in part.

The term "homing endonuclease" as used herein refers to proteins that are encoded by polynucleotides having mobile, self-splicing introns. Homing endonucleases promote the movement of at least part of the DNA sequences that encode them from one polynucleotide location to another by generating a site-specific double-stranded break at a target site in an allele that lacks the corresponding mobile intron. Examples include but are not limited to at least the following: I-Ceu I, I-Sce I, Pl-Psp I, Pl-Sce I, or a mixture thereof.

The terms "hairpin" and "stem-loop oligonucleotide" as used herein refer to a structure formed by an oligonucleotide comprised of 5' and 3' terminal regions that are inverted repeats and a non-self-complementary central region, wherein the self-complementary inverted repeats form a double-stranded stem and the non-self-complementary central region forms a single-stranded loop.

The term "in the absence of exogenous manipulation" as used herein refers to there being modification of a DNA molecule without changing the solution in which the DNA molecule is being modified. In specific embodiments, it occurs in the absence of the hand of man or in the absence of a machine that changes solution conditions, which may also be referred to as buffer conditions. In further specific embodiments, changes in temperature occur during the modification.

The term "nonidentical function" as used herein refers to two or more enzymes that do not comprise the same activity. For example, two restriction endonucleases would be considered to have identical function, although a restriction endonuclease and a ligase would be considered to have nonidentical function. Further, endonucleases are defined as enzymes that cut double stranded DNA and therefore that have identical function, although this may be performed in a variety of ways. For example, some restriction endonucleases cut frequently enough that they may be considered to have a DNA fragmentation function (such as to reduce an average DNA size to the size appropriate for efficient WGA, for example), and other restriction endonucleases have a function of cleaving unmethylated restriction sites, for example to generate a Methylome library (such as cleavage that would not reduce an average DNA size), for example.

The term "polished" as used herein refers to the repair of dsDNA fragment termini that may be enzymatically repaired, wherein the repair constitutes the fill in of recessed 3' ends or the exonuclease activity trimming back of 5' ends to form a "blunt end" compatible with adaptor ligation.

II. Specific Embodiments of the Invention

The present invention may employ particular compositions and methods as described in the following exemplary embodiments.

Figure 3:
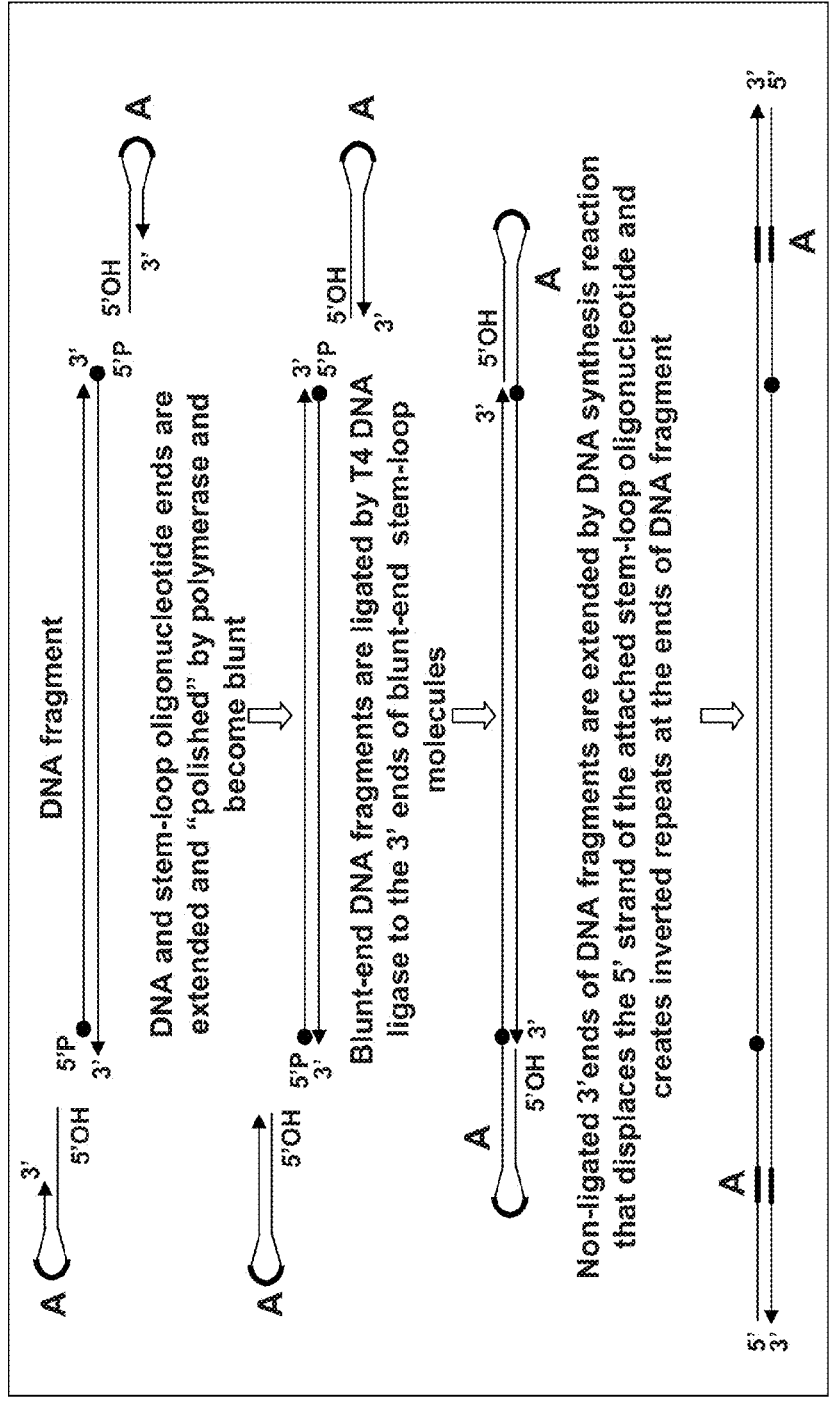
FIG. 3 is a schematic description and composition of specific components of the Enz-O-Mix method and reagents involved in the attachment of stem-loop oligonucleotides to DNA ends. Four enzymatic reactions are taking place nearly simultaneously: "polishing" of the DNA ends and the hairpin double-stranded stem-region; ligation of the stem-loop oligonucleotide 3' end to the 5' phosphate of the DNA, leaving a nick between the 3' end of DNA and the 5' end of the hairpin double-stranded stem-region; polymerase extension of the 3' DNA end that propagates toward the end of stem-loop oligonucleotide; and by strand-displacement reaction within the oligonucleotide stem region. The process results in the library of DNA fragments with inverted repeat sequences at their ends.
Figure 4:
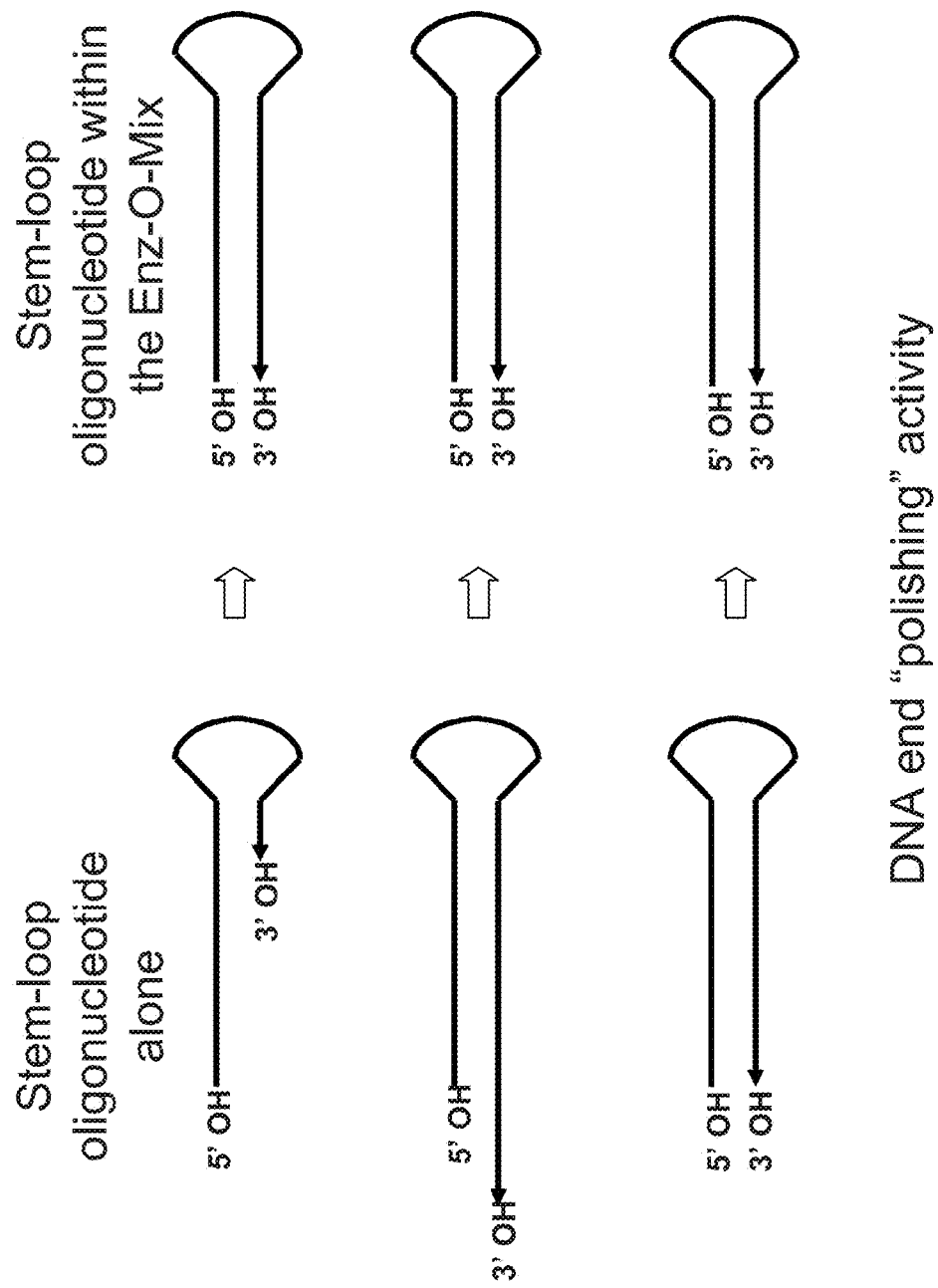
FIG. 4 shows three original secondary structures of the stem-loop oligonucleotide with the 3' or 5' protruding, or blunt end, and its final (blunt end) structure within the Enz-O-Mix.

A. One-Step Attachment of Double-Stranded Inverted Repeat DNA Sequences to DNA Fragments Using Stem-Loop Oligonucleotides In this embodiment of the present invention, as illustrated in FIG. 3, DNA is incubated with an exemplary mixture comprising a stem-loop oligonucleotide with 3' recessed, 3' protruding, or blunt end (FIG. 4); a 3' proofreading DNA polymerase (Klenow fragment of the DNA polymerase I, T4 DNA polymerase, etc.); T4 DNA ligase; Enz-O-Mix Universal Buffer; ATP; and dNTPs. Four exemplary enzymatic reactions are taking place simultaneously: "polishing" of the DNA ends and the oligonucleotide double-stranded stem-region; ligation of the oligonucleotide 3' end to the 5' phosphate of the DNA leaving a nick between the 3' end of DNA and the 5' end of the oligonucleotide double-stranded stem-region; polymerase extension of the 3' DNA end that propagates toward the end of the stem-loop oligonucleotide; and a strand-displacement reaction within the oligonucleotide stem region. The process results in a library of DNA fragments with inverted repeat adaptors at their ends.

B. Transcription-Mediated Amplification of DNA Library with Attached Promoter Sequence In this embodiment of the present invention, as illustrated in FIG. 5, a DNA library produced by incubation with an exemplary mixture comprising a stem-loop oligonucleotide with 3' recessed, 3' protruding, or blunt end (FIG. 4) and T7 promoter sequence within the stem or loop region; a 3' proofreading DNA polymerase (Klenow fragment of the DNA polymerase I, T4 DNA polymerase, etc.); T4 DNA ligase; Enz-O-Mix Universal Buffer; ATP; and dNTPs (as shown in FIG. 3), is used as a template for the transcription-mediated amplification. In FIG. 5A, promoter sequence resides within the stem region of a stem-loop oligonucleotide, and there are two inversely oriented promoters at the ends of all DNA fragments: internally located promoter that initiates synthesis of long RNA molecules, and terminal promoter that initiates synthesis of very short (<10 bases) RNA initiation products (not shown in FIG. 5A) (similar products will be produced from the non-attached stem-loop oligonucleotides present in the mixture). In FIG. 5B, the promoter sequence resides within the loop region of a stem-loop oligonucleotide, and there is only one active promoter element that supports synthesis of long RNA products. The transcription-mediated amplification is achieved by incubation of the synthesized DNA library (see above) with T7 RNA polymerase in the presence of ribonucleotides (rNTPs). The products of this reaction are RNA molecules.

Supplementation of a transcription-mediated amplification reaction with additional ingredients, such as a reverse transcriptase polymerase (M-MuLV reverse transcriptase, AMV reverse transcriptase, etc.) and a primer complementary to the T7 promoter or the internal stem region at the 3' end of the RNA molecule (see FIG. 6B), would allow the synthesis of a complementary cDNA. Efficient priming at the 3' ends of RNA is achieved by blocking the transcription-mediated RNA synthesis within the adaptor region to prevent formation of a folded structure at the 3' ends of RNA. Transcriptional arrest can be achieved by using the same chemical or enzymatic modifications of a stem-loop oligonucleotide as described herein in Sections E, F, G, and H and shown in FIGS. 8, 10, and 16C. The products of such a reaction are double stranded DNA/RNA hybrid molecules.

Figure 6A:
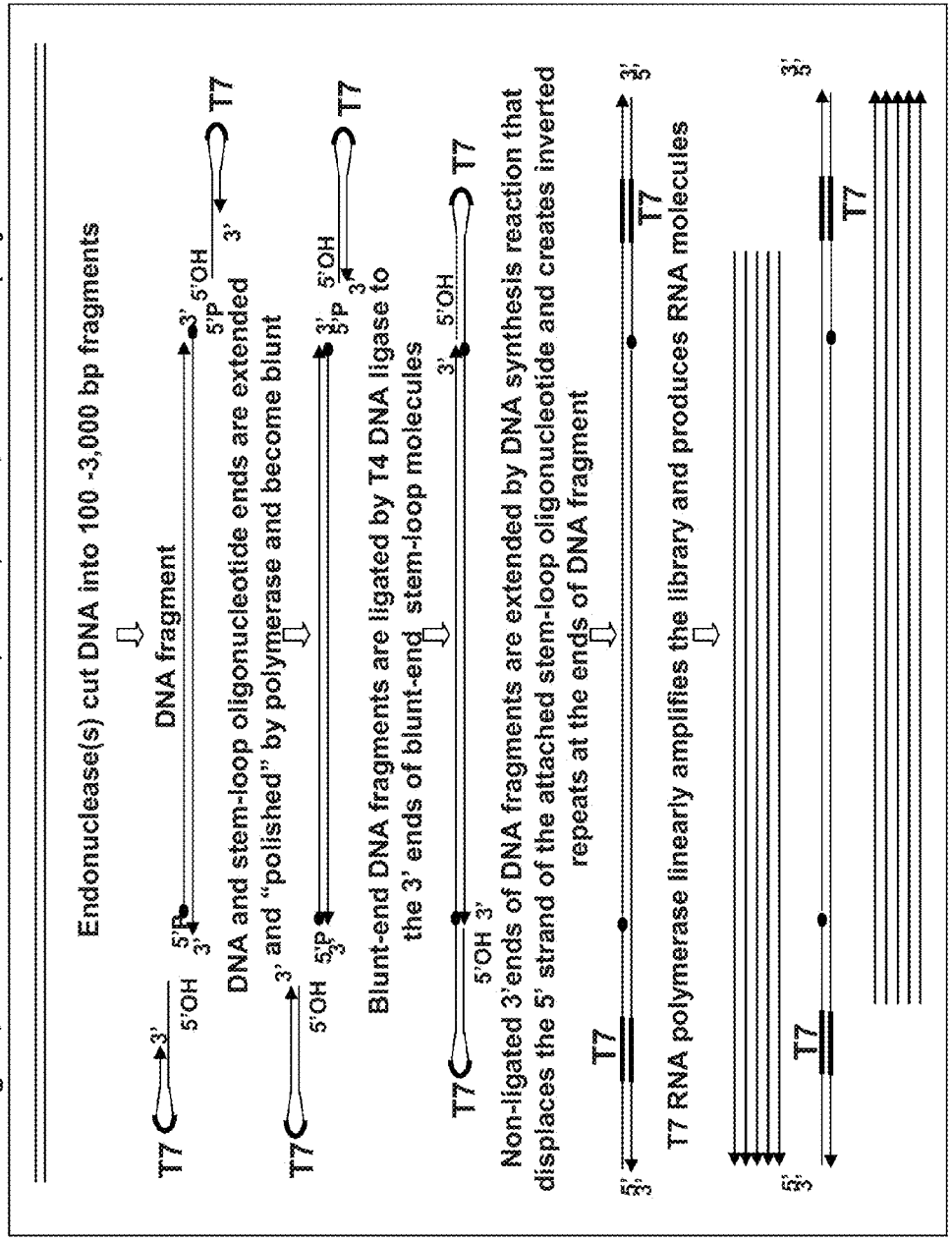
FIG. 6A illustrates the components and enzymatic reactions involved in the one-step DNA amplification by transcription using Enz-O-Mix reagent (Enz-O-Mix 5 in FIG. 19B, for example). The process linearly amplifies DNA and produces single stranded RNA molecules.

C. Enz-O-Mix Reagents and Procedures for One-Step Library Synthesis and Linear Amplification by Transcription This embodiment is shown in FIG. 6A and illustrates exemplary components and enzymatic reactions involved in the process catalyzed by Enz-O-Mix reagent (Enz-O-Mix 5, FIG. 19B). This reagent simultaneously synthesizes a DNA library with T7 promoter at the ends and amplifies it linearly by transcription. The Enz-O-Mix reagent 5 comprises a stem-loop oligonucleotide with T7 promoter sequence in the loop region; a DNA fragmentation endonuclease (a restriction enzyme, DNase I, methylation-specific nuclease McrBC, benzonase, apoptotic endonuclease, etc.); a 3' proofreading DNA polymerase; T4 DNA ligase; T7 RNA polymerase; Enz-O-Mix Universal Buffer; rNTP; and dNTPs. First, HMW DNA is fragmented by an endonuclease to produce 100-3,000 bp DNA fragments. The T4 DNA polymerase "polishes" the DNA ends and the stem-loop oligonucleotide double-stranded stem-region, and T4 ligase ligates the 3' end of the oligonucleotide to the 5' phosphate of the DNA leaving a nick between the 3' end of DNA and the 5' end of the oligonucleotide double-stranded stem-region. DNA polymerase extends the available 3' DNA end toward the end of a stem-loop oligonucleotide and generates a library of DNA fragments with active conformation of T7 promoter at their ends. RNA polymerase transcribes the library, linearly amplifying DNA and producing single stranded RNA molecules.

In the case of fragmented DNA (for example, cell-free DNA from blood and/or urine) the reaction does not require a fragmentation endonuclease (Enz-O-Mix 2, FIG. 19A); all other components may be the same as described above.

Figure 6B:
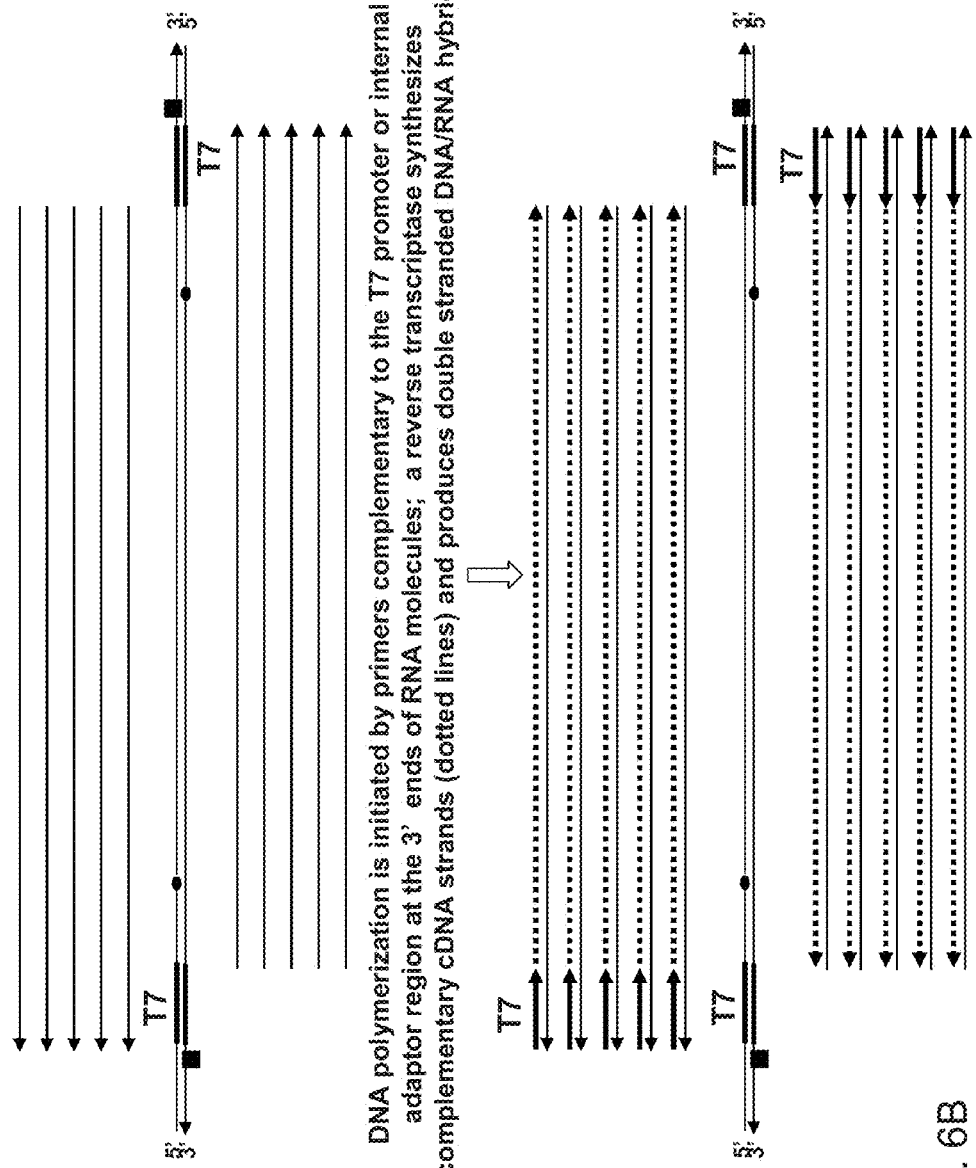
FIG. 6B illustrates additional components and enzymatic reactions involved in the one-step DNA amplification by transcription accompanied by the synthesis of complementary cDNA strand. The transcription (replication) block (see Sections E-H and FIGS. 8-10) is introduced into the stem-loop oligonucleotide upstream of the T7 promoter region to prevent formation of an inverted repeat at the 3' end of RNA molecules and thus increase the efficiency of the oligo T7 priming (the transcription block is shown as a black square). The process can linearly amplify DNA and produce double stranded DNA/RNA hybrids.

In another embodiment, as shown in FIG. 6B, supplementation of a transcription-mediated amplification reaction with the additional ingredients, such as a reverse transcriptase polymerase (M-MuLV reverse transcriptase, AMV reverse transcriptase, etc.) and T7 primer, allows the synthesis of a complementary cDNA. Efficient priming at the 3' ends of RNA is achieved by blocking the transcription-mediated RNA synthesis within the adaptor region to prevent formation of a folded structure at the 3' ends of RNA. Transcriptional arrest can be achieved by using the same chemical or enzymatic modifications of a stem-loop oligonucleotide as described herein in Sections E, F, G, and H and shown in FIGS. 8, 10, and 16C. The products of such a reaction are double stranded DNA/RNA hybrid molecules.

Figure 7:
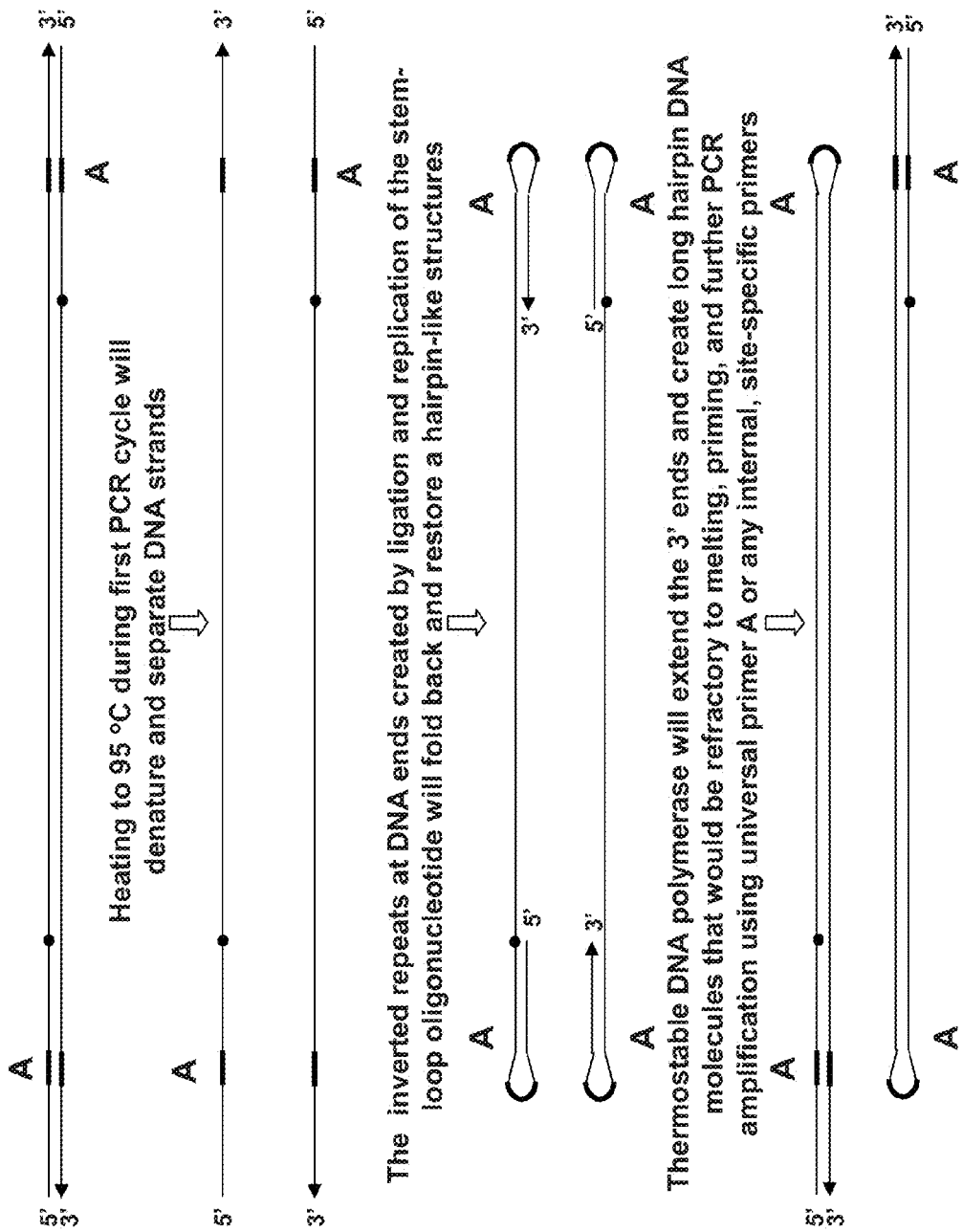
FIG. 7 is an illustration of the inhibitory effect on PCR of inverted repeats attached to both ends of DNA fragments. Heating and replication generates DNA molecules refractory to melting, priming, and PCR amplification either using the universal primer A or any internal site-specific primer pair.

D. Inhibitory Effect of Inverted Repeats at DNA Ends on Whole Genome Amplification and Locus-Specific PCR As shown in FIG. 7, inverted repeats attached to both ends of DNA fragments have an inhibitory effect on PCR process. Heating to 95° C. during a first PCR cycle denatures DNA strands and generates hairpin-like structures at both 3' and 5' ends of DNA fragments due to the folding of terminal inverted repeat sequences (the melting temperature for these structures is usually more than 100° C.). Subsequent cooling activates a thermostable DNA polymerase and results in extension of the self-primed 3' ends and creation of long hairpin DNA molecules refractory to melting, priming, and PCR amplification. Neither the universal primer A nor any internal, site-specific primer pair would produce any detectable PCR product.

Figure 8:
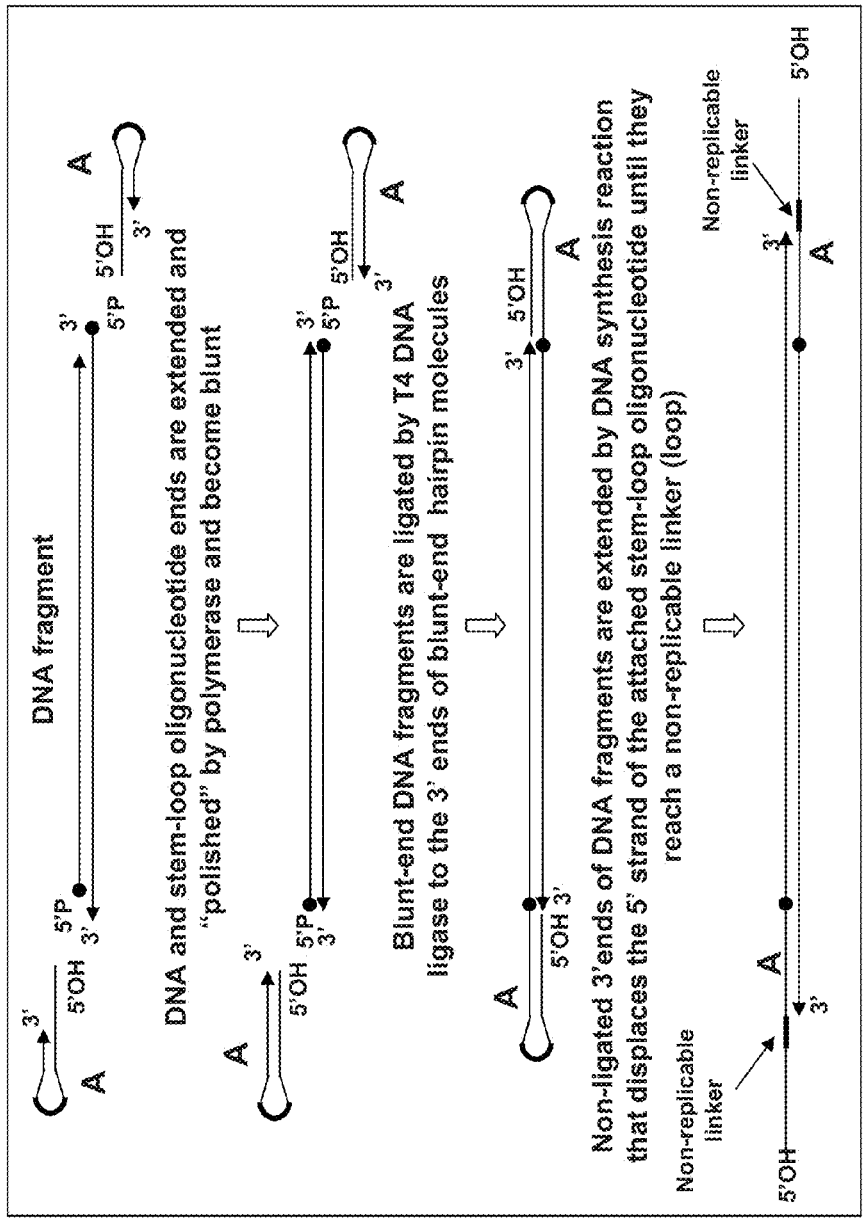
FIG. 8 is a schematic description of the one-step Enz-O-Mix attachment process for a stem-loop oligonucleotide with non-replicable linker. The following enzymatic reactions are taking place nearly simultaneously: "polishing" of the DNA ends and the stem-loop oligonucleotide double-stranded stem-region; ligation of the oligonucleotide 3' end to the 5' phosphate of the DNA, leaving a nick between the 3' end of DNA and the 5' end of the hairpin double-stranded stem-region; polymerase extension of the 3' DNA end that propagates toward the end of oligonucleotide and stops at the replication block (non-replicable linker) within the loop or outside the loop but no more than about six bases away from the loop. The process results in the library of DNA fragments with universal sequence A at the ends and an inverted repeat attached only to the 5' end of DNA.

E. Library Created by Enz-O-Mix Attachment Process with a Stem-Loop Oligonucleotide with a Non-Replicable Linker This embodiment is illustrated in FIG. 8 and describes the one-step Enz-O-Mix attachment process for a stem-loop oligonucleotide with a non-replicable linker. The exemplary reaction mix comprises fragmented DNA; a stem-loop oligonucleotide with 3' recessed, 3' protruding or blunt end (FIG. 4), and a non-replicable linker (such as about in the central part of the oligonucleotide); a 3' proofreading DNA polymerase (Klenow fragment of the DNA polymerase I, T4 DNA polymerase, etc.); T4 DNA ligase; Enz-O-Mix Universal Buffer; ATP; and dNTPs. At least the following enzymatic reactions are taking place: "polishing" of the DNA ends and the stem-loop oligonucleotide double-stranded stem-region; ligation of the oligonucleotide 3' end to the 5' phosphate of the DNA, leaving a nick between the 3' end of DNA and the 5' end of the oligonucleotide double-stranded stem-region; polymerase extension of the 3' DNA end that propagates toward the end of stem-loop oligonucleotide and stops somewhere within the loop or close to the loop region at the replication block, for example. The process results in the library of DNA fragments with universal sequence A at the ends and an inverted repeat attached only to the 5' end of DNA.

Figure 9:
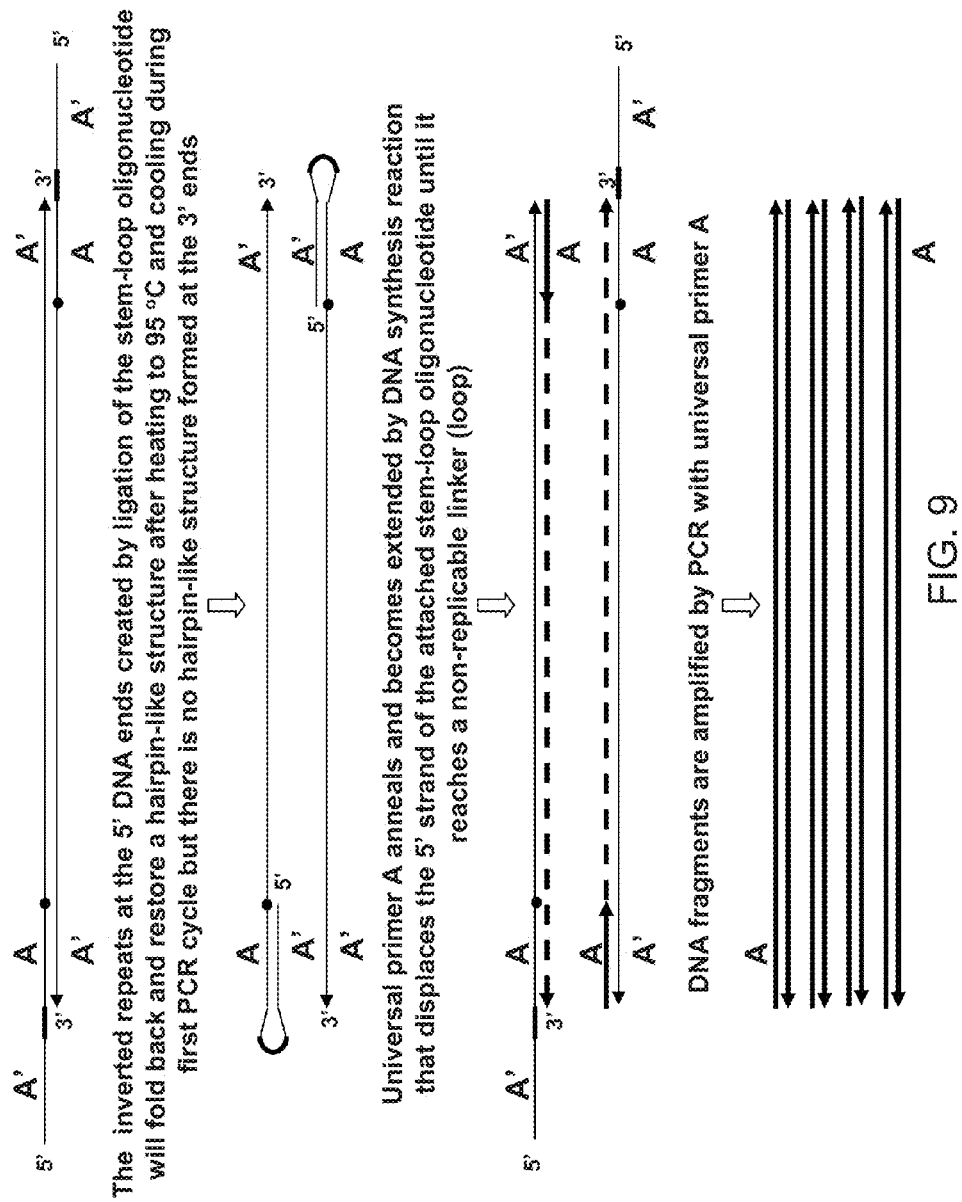
FIG. 9 is an illustration of the absence of an inhibitory effect on PCR of inverted repeats attached to only 5' ends of DNA fragments. Heating and replication generates DNA molecules with the universal sequence A and no inverted repeats at the ends (shown by dash lines) that can be successfully amplified by PCR.

F. Libraries Produced by the Enz-O-Mix Attachment Process with a Stem-Loop Oligonucleotide Comprising a Non-Replicable Linker have No Inhibitory Effect on PCR As shown in FIG. 9, a DNA library produced by the Enz-O-Mix (Enz-O-Mix 1 in the case of fragmented DNA, FIG. 19A, or Enz-O-Mix 4 in the case of HMW DNA, FIG. 19B) attachment process with a stem-loop oligonucleotide with a non-replicable linker has no inhibitory effect on WGA and PCR. Heating to 95° C. during first PCR cycle denatures DNA strands and generates hairpin-like structures only at the 5' ends of DNA fragments. At a lower PCR temperature, the universal primer A anneals to the A' region at the 3' ends of DNA fragments, and a thermostable DNA polymerase replicates DNA until it reaches a non-replicable linker in the loop or in the region adjacent to the loop stem region of the stem-loop oligonucleotide attached to the 5' DNA end. Replication of the hairpin region is accompanied by a strand-displacement reaction within the oligonucleotide stem region. Synthesized DNA molecules with the universal sequence A and no inverted repeats at the ends (shown by dashed lines) can then successfully be amplified by PCR.

Figure 10A:
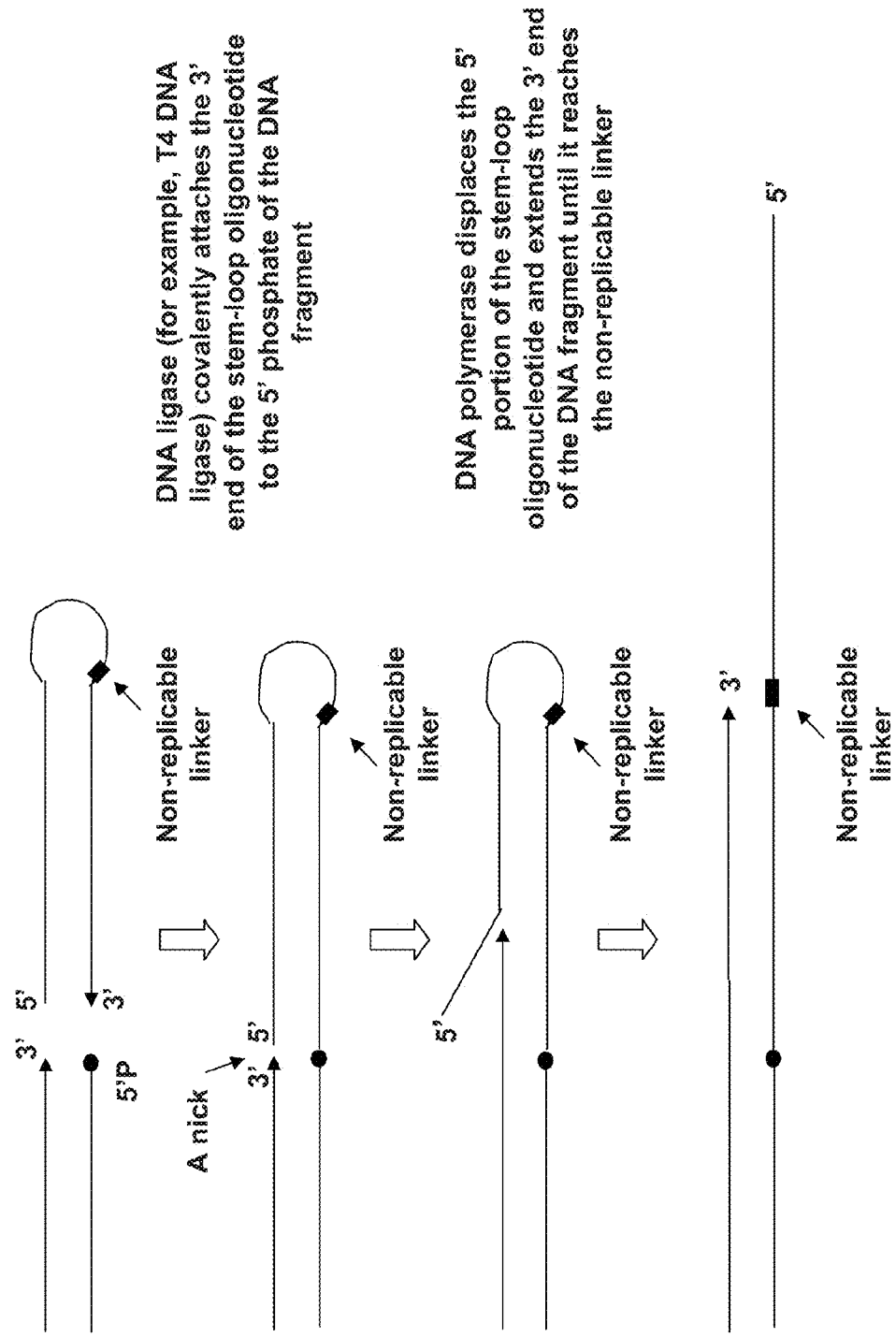
FIG. 10A shows the structure of a stem-loop oligonucleotide with non-replicable linker introduced chemically during oligonucleotide synthesis and detailed events occurring at a DNA end during the multi-enzyme attachment process. The process occurs as described in FIG. 8.

G. Stem-Loop Oligonucleotide with a Non-Replicable Linker Introduced During Chemical Synthesis FIG. 10A shows the structure of a stem-loop oligonucleotide with a non-replicable linker introduced chemically during oligonucleotide synthesis and shows detailed events occurring at DNA end during the exemplary multi-enzyme attachment process. Many structural modifications within the oligonucleotide, such as the exemplary hexaethelene glycol linker, the abasic site, or a cluster of abasic sites (a gap), a bulky group within the base or backbone, etc. can block propagation of the DNA replication. The exemplary process occurs as described in FIG. 8.

Figure 10B:
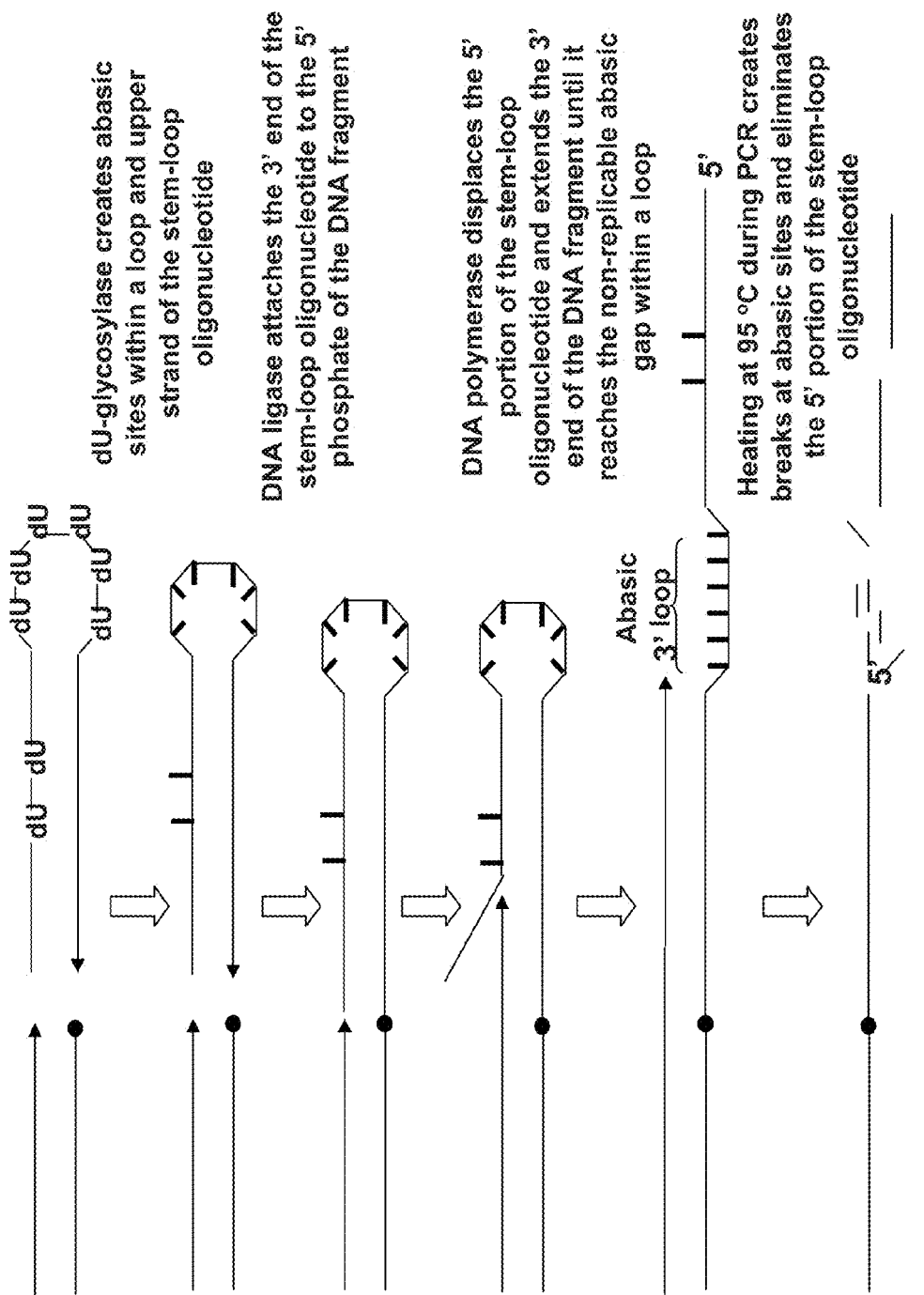
FIG. 10B shows the structure of a stem-loop oligonucleotide with non-replicable linker introduced enzymatically during the attachment reaction and detailed events occurring at a DNA end during the multi-enzyme attachment process. Specifically, dU-glycosylase generates abasic sites within the loop and upper strand of the stem region of the stem-loop oligonucleotide. The abasic sites within a loop generate a non-replicable region, while the sites in a stem destabilize the duplex and facilitate strand displacement reaction. The process results in a library of DNA fragments with universal sequence at the ends and an inverted repeat attached only to the 5' end of DNA. Heating at 95° C. during PCR generates breaks at abasic sites and completely eliminates the 5' portion of a stem-loop oligonucleotide.

H. Stem-Loop Oligonucleotide with a Non-Replicable Abasic Gap Generated Enzymatically by dU-Glycosylase During the Attachment Process This embodiment is illustrated in FIG. 10B and shows the structure of a stem-loop oligonucleotide with non-replicable linker introduced enzymatically during the attachment reaction and shows detailed events occurring at a DNA end during the exemplary multi-enzyme attachment process. The exemplary reaction mix comprises fragmented DNA; a stem-loop oligonucleotide with 3' recessed, 3' protruding or blunt end (FIG. 4), and dU bases within the loop and stem regions (optional); a dU-glycosylase; a 3' proofreading DNA polymerase; T4 DNA ligase; Enz-O-Mix Universal Buffer; ATP; and dNTPs. dU-glycosylase creates abasic sites within the loop and upper strand of the stem region of the oligonucleotide; DNA polymerase "polishes" the ends of DNA and the stem-loop oligonucleotide and generates blunt ends; T4 DNA ligase attaches the 3' end of the oligonucleotide and the 5' end of DNA fragment, leaving a nick between the 3' end of DNA and the 5' end of the hairpin double-stranded stem-region; a DNA polymerase extends the 3' end of DNA toward the end of the stem-loop oligonucleotide and stops somewhere within the loop or close to the loop region of the oligonucleotide, such as at the replication block generated by a contiguous abasic site region. The role of abasic sites in the about central stem region is to destabilize base pairing and facilitate the strand displacement reaction. The process results in a library of DNA fragments with universal sequence at both ends and an inverted repeat attached only to the 5' end of DNA, thereby suitable for PCR amplification. Heating at 95° C. during PCR generates breaks at abasic sites and completely eliminates the 5' portion of a stem-loop oligonucleotide.

I. Stem-Loop Oligonucleotides are Advantageous for the Enz-O-Mix Attachment Process This embodiment illustrates the low efficiency and problems associated with use of standard adaptors in the Enz-O-Mix attachment process, although in alternative embodiments standard adaptors may be employed.

FIG. 11A shows a standard adaptor formed by two different oligonucleotides, wherein one of them has the 5' phosphate group, and possible products formed when such an adaptor is used in the multi-enzyme one-step ligation process. The adaptor should be present at high concentration to provide efficient ligation to DNA ends. Because both ends of a standard adaptor can be ligated to DNA and form adaptor-adaptor conjugates (a dominating product of the reaction), a number of undesirable products may be high, and the yield of desirable molecules may be low, in certain aspects.

Figure 11B:
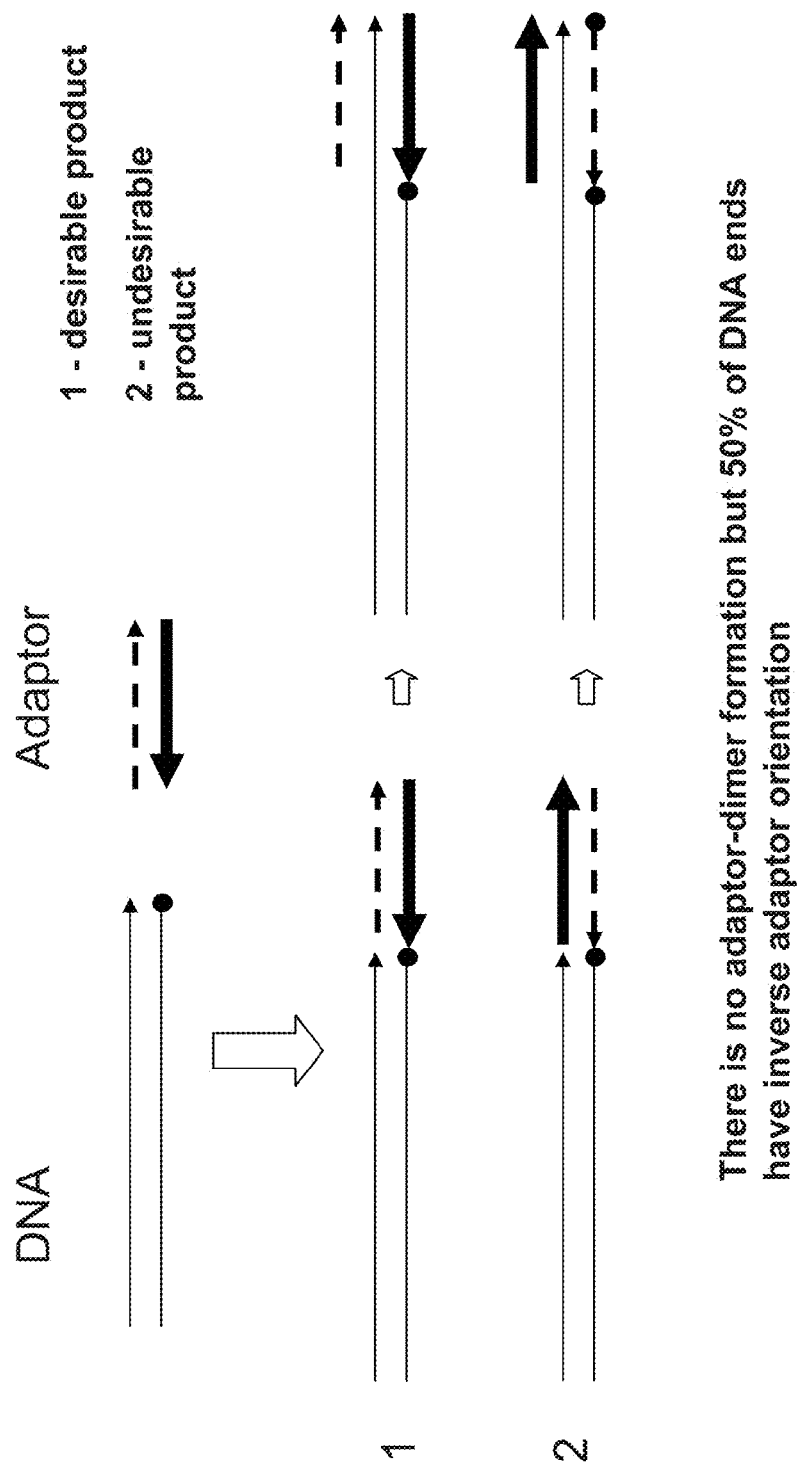
FIG. 11B shows a standard adaptor formed by two different oligonucleotides without phosphate group and two products formed when such an adaptor is used in the multi-enzyme one-step ligation process. Only 50% of formed molecules are desirable products with correct orientation of the adaptor, whereas the other 50% of molecules have inverse adaptor orientation.

FIG. 11B shows a standard adaptor formed by two different oligonucleotides without phosphate group and two products formed when such an adaptor is used in the multi-enzyme one-step ligation process. Only 50% of formed molecules are desirable products with correct orientation of the adaptor, while the other 50% of molecules have inversed adaptor orientation.

Figure 11C:
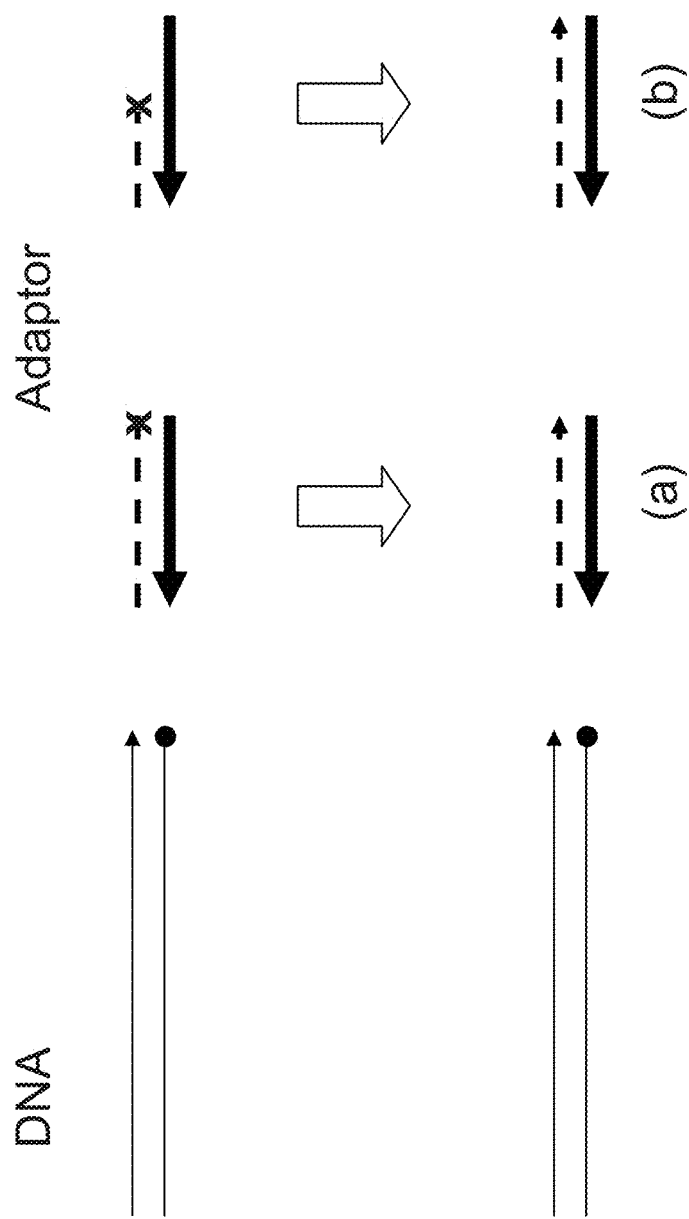
FIG. 11C shows a standard adaptor formed by two different oligonucleotides without a phosphate group, a protective group at the 3' end of one oligonucleotide, and products formed when such an adaptor is used in the multi-enzyme one-step ligation process. As in the case described on FIG. 11B, only 50% of formed molecules are desirable products with correct orientation of the adaptor, whereas the other 50% of molecules have inversed adaptor orientation.

FIG. 11C shows a standard adaptor formed by two different oligonucleotides without phosphate group but with a protective group at the 3' end of one oligonucleotide and the products formed when such adaptor is used in the multi-enzyme one-step ligation process. A blocked 3' end or recessive 3' end or both are well-known in the art and have been used to prevent formation of products with inversed adaptor orientation during ligation reaction. Presence of a 3' proofreading DNA polymerase in the mix will replace the terminal 3' blocked nucleotide with normal nucleotide (a), and repair and extend the recessed, blocked 3' end (b). As in the case described for FIG. 11B, only 50% of formed molecules are desirable products with correct orientation of the adaptor, while the other 50% of molecules have inversed adaptor orientation.

Figure 12:
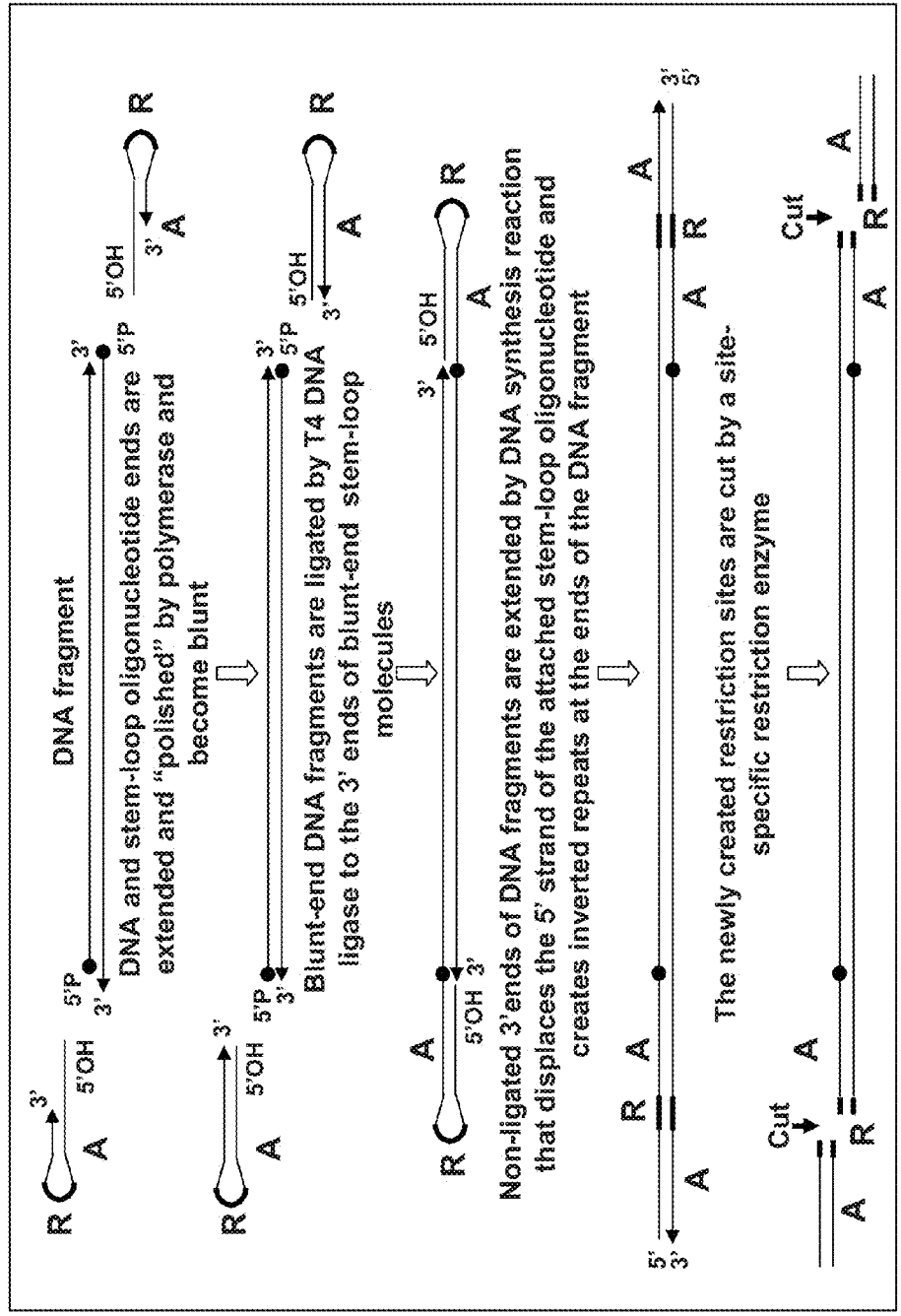
FIG. 12 is a schematic description of the one-step Enz-O-Mix attachment process for a stem-loop oligonucleotide with an enzymatically cleavable site generated during the multi-enzyme reaction. Specifically, the endonuclease recognizes and cuts the oligonucleotide specific oligo-sequence R when it adopts a double-stranded conformation as a result of the attachment process. The reaction results in a library of DNA fragments with universal sequence A at the ends and no inverted repeat attached to the ends of DNA fragments.

J. Library Generated by the Enz-O-Mix Attachment Process Using a Stem-Loop Oligonucleotide with a Cleavable Site Generated During the Multi-Enzyme Reaction In this embodiment of the present invention, as illustrated in FIG. 12, there is a schematic description of the one-step Enz-O-Mix attachment process for a stem-loop oligonucleotide with an enzymatically cleavable site generated during the multi-enzyme reaction. The reaction mix contains fragmented DNA, a stem-loop oligonucleotide with 3' recessed, 3' protruding or blunt end (FIG. 4), and a specific DNA sequence R within the loop or in the loop and adjacent stem region; a 3' proofreading DNA polymerase (Klenow fragment of the DNA polymerase I, T4 DNA polymerase, etc.); T4 DNA ligase; an endonuclease that recognizes and cuts the oligonucleotide specific oligo-sequence R when it adopts a double-stranded conformation; Enz-O-Mix Universal Buffer; ATP; and dNTPs. Four enzymatic reactions are taking place nearly simultaneously: "polishing" of the DNA ends and the stem-loop oligonucleotide double-stranded stem-region; ligation of the oligonucleotide 3' end to the 5' phosphate of the DNA leaving a nick between the 3' end of DNA and the 5' end of the hairpin double-stranded stem-region, polymerase extension of the 3' DNA end that propagates toward the end of stem-loop oligonucleotide and generates inverted repeats at the ends of DNA fragments;

and, finally, cleavage of inverted repeats by an endonuclease at the R sites. The process results in a library of DNA fragments with universal sequence A at the ends, and no inverted repeat attached to the ends of DNA fragments, which is thereby competent for PCR amplification.

Figure 13A:
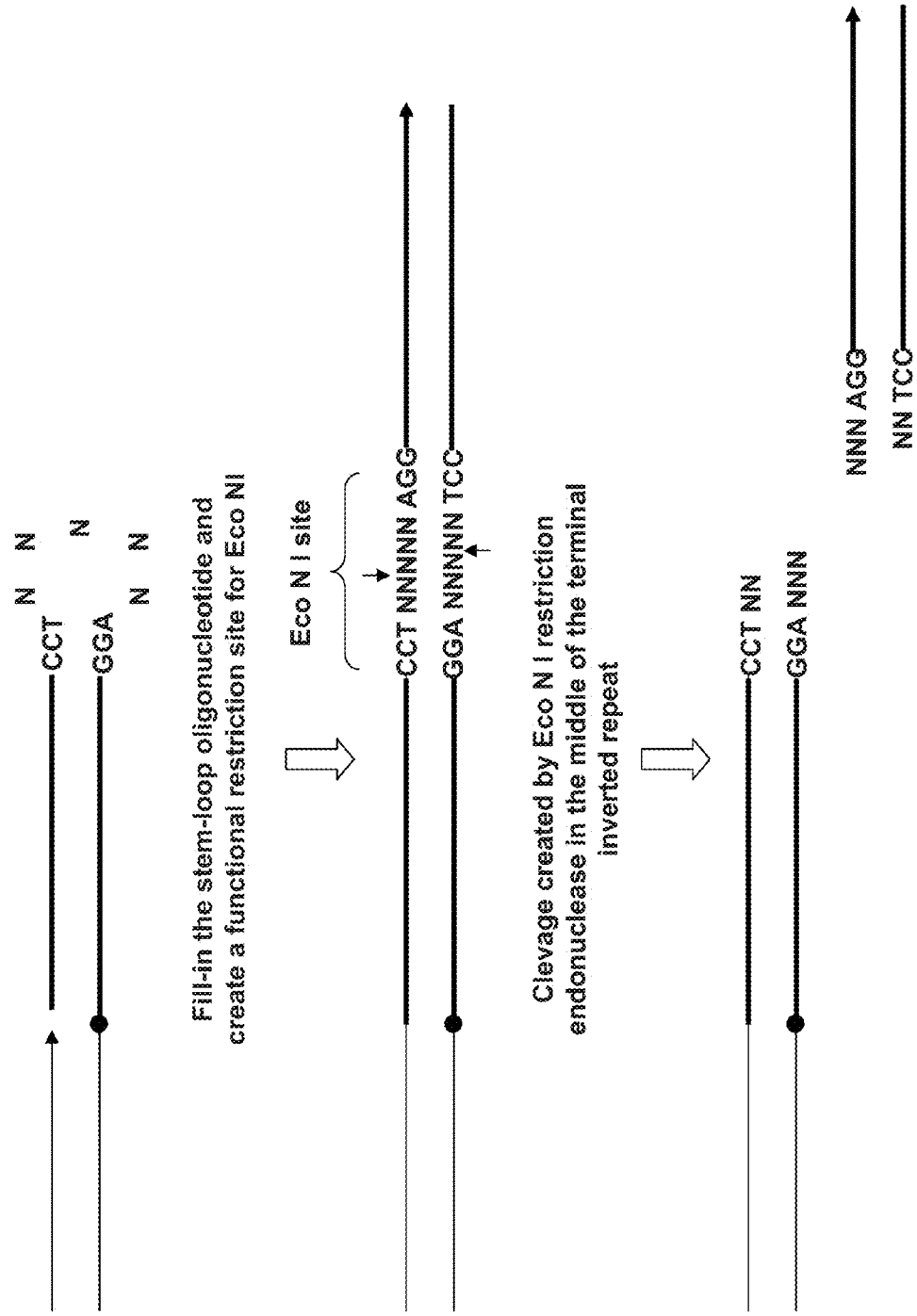
FIG. 13A shows the stem-loop oligonucleotide with the recognition sequence for the restriction endonuclease Eco NI located at the loop region. The enzyme can not cut the CCTNNNNNAGG (SEQ ID NO: 20) region within the stem-loop oligonucleotide (not a recognizable structure) but it can cut it efficiently when the oligonucleotide is attached to a DNA end and adopts a canonical (double-stranded) Watson-Crick conformation.

K. Examples of Stem-Loop Adaptors with a Cleavable Restriction Site Generated by DNA Synthesis FIG. 13A shows an exemplary stem-loop oligonucleotide with recognition sequence for the restriction endonuclease Eco NI located at the loop region. The enzyme can not cut the CCTNNNNNAGG (SEQ ID NO: 20) region within the stem-loop oligonucleotide (an unrecognizable structure) but it will cut it efficiently when the oligonucleotide is attached to a DNA end and adopts a canonical (double-stranded) Watson-Crick conformation. Cleavage with Eco NI eliminates inverted repeats that inhibit PCR applications.

Figure 13B:
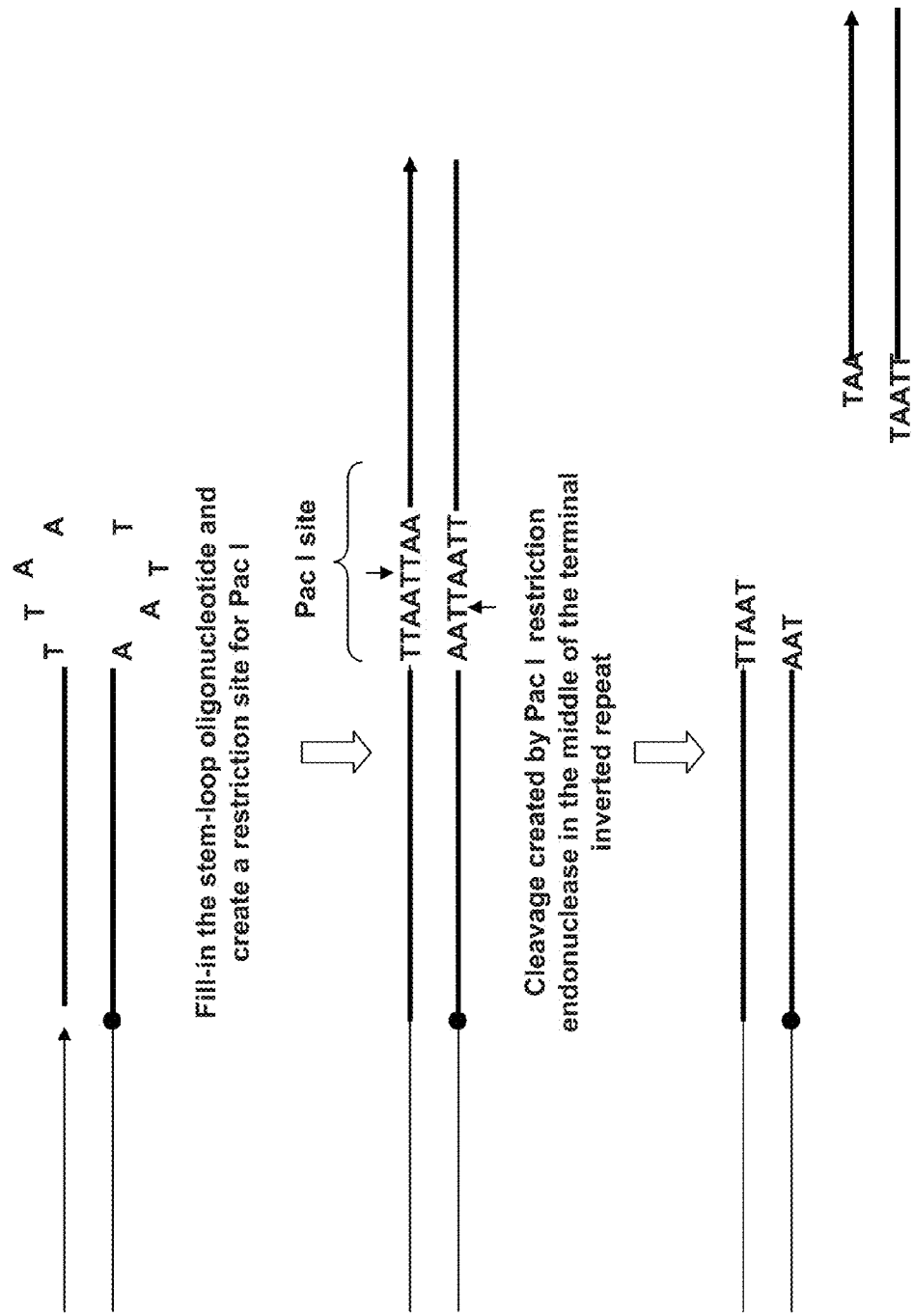
FIG. 13B shows the stem-loop oligonucleotide with the recognition sequence for the restriction endonuclease Pad located within the loop region. The enzyme can not cut the single stranded TTAATTAA region within the stem-loop oligonucleotide, but it cuts it efficiently when the oligonucleotide is attached to a DNA end and adopts a canonical (double-strand) Watson-Crick conformation.

FIG. 13B shows an exemplary stem-loop oligonucleotide with recognition sequence for the restriction endonuclease Pac I located within the loop region. The enzyme can not cut the TTAATTAA region within the stem-loop oligonucleotide, but it will cut it efficiently when the oligonucleotide is attached to a DNA end and adopts a canonical (double-stranded) Watson-Crick conformation. Cleavage eliminates inverted repeats that inhibit PCR applications. Use of a rare-cutting restriction enzyme such as Pac I reduces the number of DNA fragments affected by the enzyme cleavage.

Figure 13C:
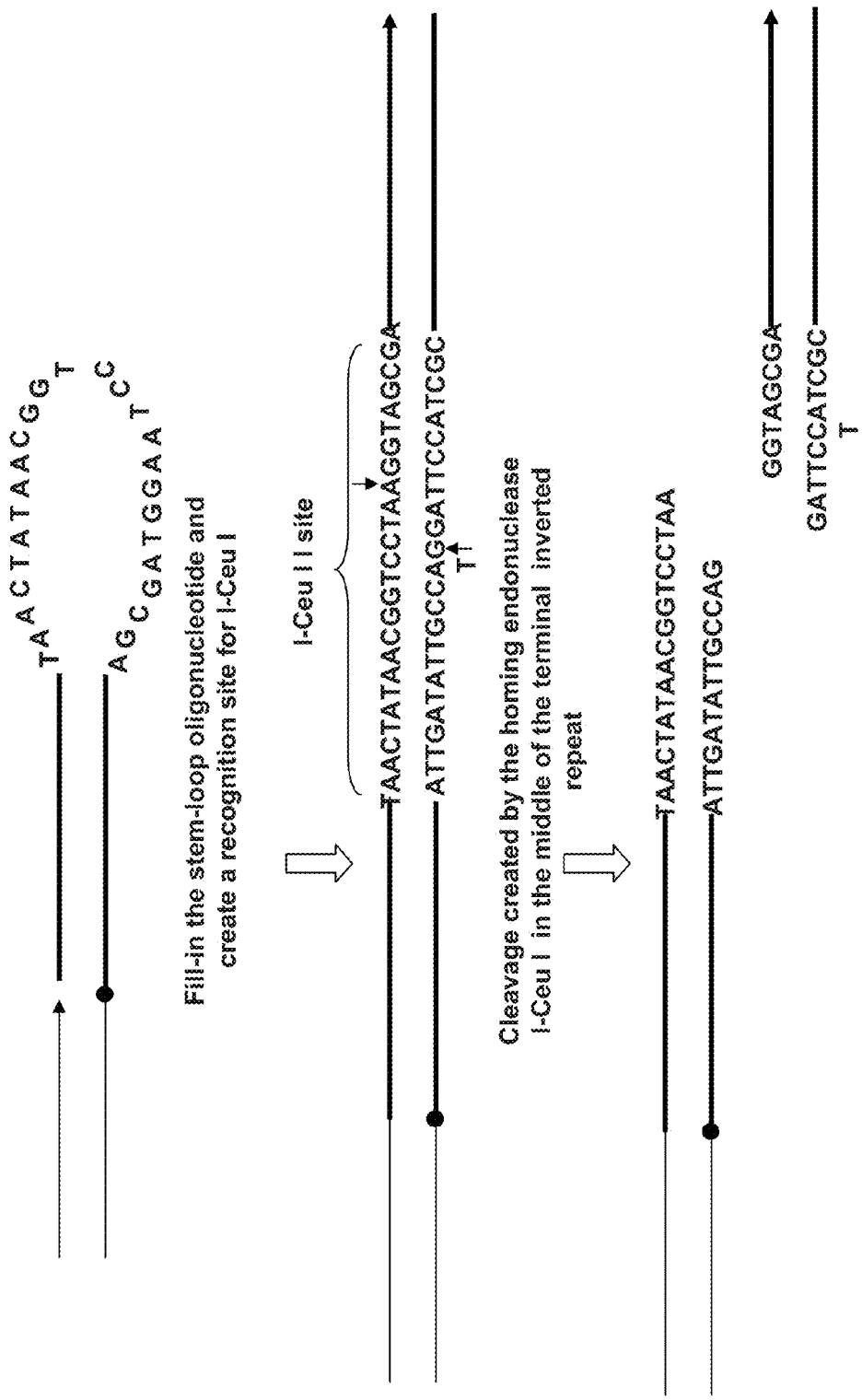
FIG. 13C shows the stem-loop oligonucleotide with the recognition sequence for the exemplary homing endonuclease I-Ceu I located within the loop region. The enzyme can not cut the 26-base single-stranded region within the hairpin loop, but it cuts efficiently when the oligonucleotide is attached to a DNA end and adopts a canonical (double-stranded) Watson-Crick conformation.

FIG. 13C shows the stem-loop oligonucleotide with recognition sequence for the homing endonuclease I-Ceu I located within the loop region. The enzyme can not cut the 26-base single-stranded region within the loop, but it cuts efficiently when the stem-loop oligonucleotide is attached to a DNA end and adopts a canonical (double-stranded) Watson-Crick conformation. Cleavage eliminates inverted repeats that inhibit PCR applications. Use of a homing endonuclease dramatically reduces and practically eliminates cleavage of genomic DNA.

Figure 14:
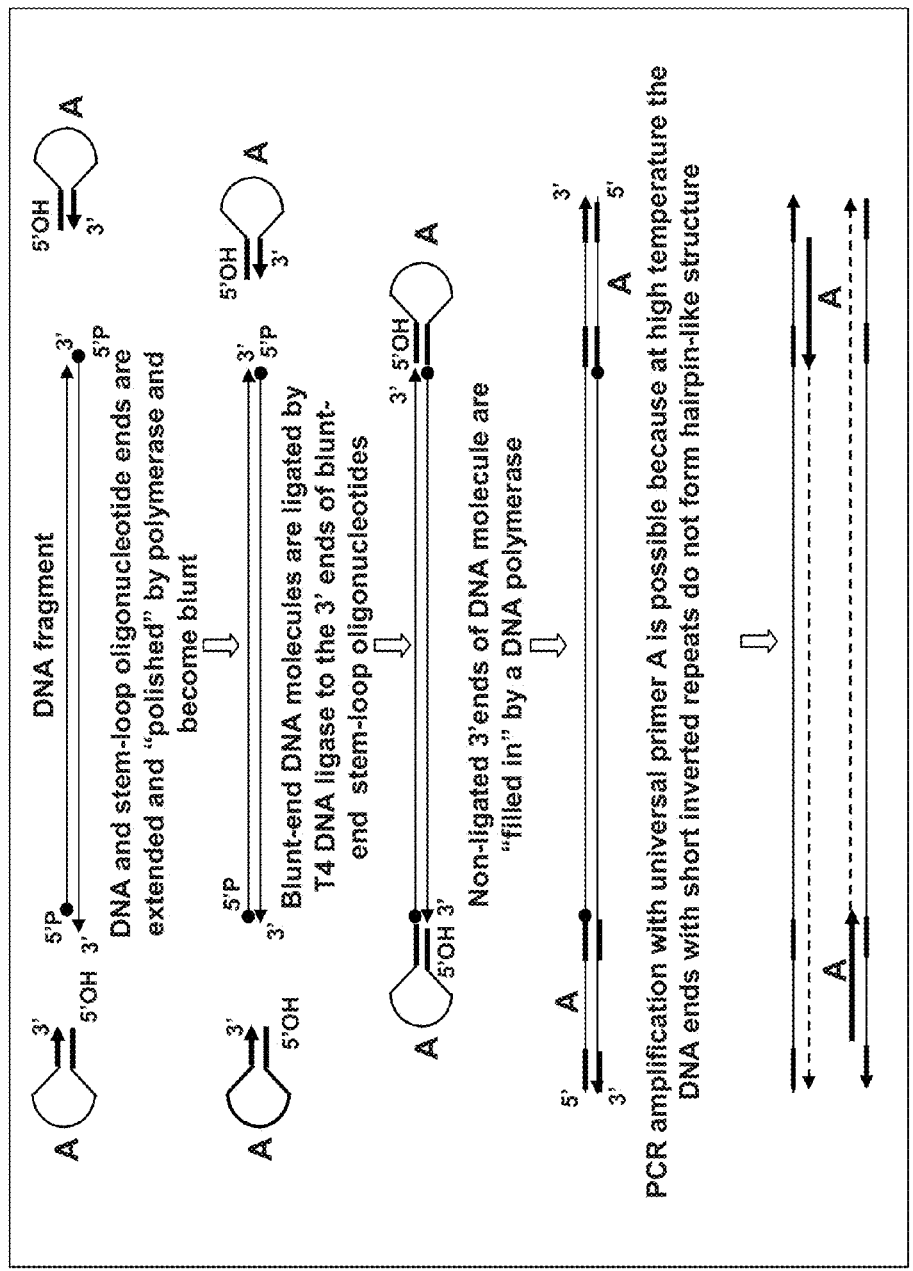
FIG. 14 is a schematic description of the one-step Enz-O-Mix attachment process for a stem-loop oligonucleotide with a very short stem. The process results in the library of DNA fragments with universal sequence A at the ends and very short inverted repeat attached to the ends of DNA fragments. Amplification by PCR is possible, because the melting temperature for terminal hairpins is low enough to prevent folding, self-priming and formation of long hairpin molecules, as shown on FIG. 7.

L. Library Generated by the Enz-O-Mix Attachment Process with a Stem-Loop Oligonucleotide with a Short Stem Amplifiable libraries can be synthesized in the presence of but not limited to a stem-loop oligonucleotide with a non-replicable or cleavable linker. FIG. 14 shows a schematic description of an exemplary one-step Enz-O-Mix attachment process using a stem-loop oligonucleotide with a very short stem. The exemplary reaction mix comprises fragmented DNA, a stem-loop oligonucleotide with 3' recessed, 3' protruding or blunt end (FIG. 4), and a short stem region (5-8 bases); a 3' proofreading DNA polymerase (Klenow fragment of the DNA polymerase I, T4 DNA polymerase, etc.); T4 DNA ligase; Enz-O-Mix Universal Buffer; ATP; and dNTPs. Three enzymatic reactions are taking place: "polishing" of the DNA ends and the stem-loop oligonucleotide double-stranded stem-region; ligation of the oligonucleotide 3' end to the 5' phosphate of the DNA, leaving a nick between the 3' end of DNA and the 5' end of the hairpin double-stranded stem-region; and polymerase extension of the 3' DNA end that propagates toward the end of the stem-loop oligonucleotide and generates short inverted repeats at the ends of DNA fragments. The process results in a library of DNA fragments with universal sequence A at the ends and a very short inverted repeat attached to the ends of DNA fragments (FIG. 14, shown in bold). PCR is possible because the melting temperature for terminal hairpins is low enough to prevent folding, self-priming and formation of long hairpin molecules, as shown on FIG. 7. Primer A (representing the 3' portion of a stem-loop oligonucleotide without the complementary 5' region) or even the whole stem-loop oligonucleotide can be utilized as a primer for PCR amplification.

Figure 15:
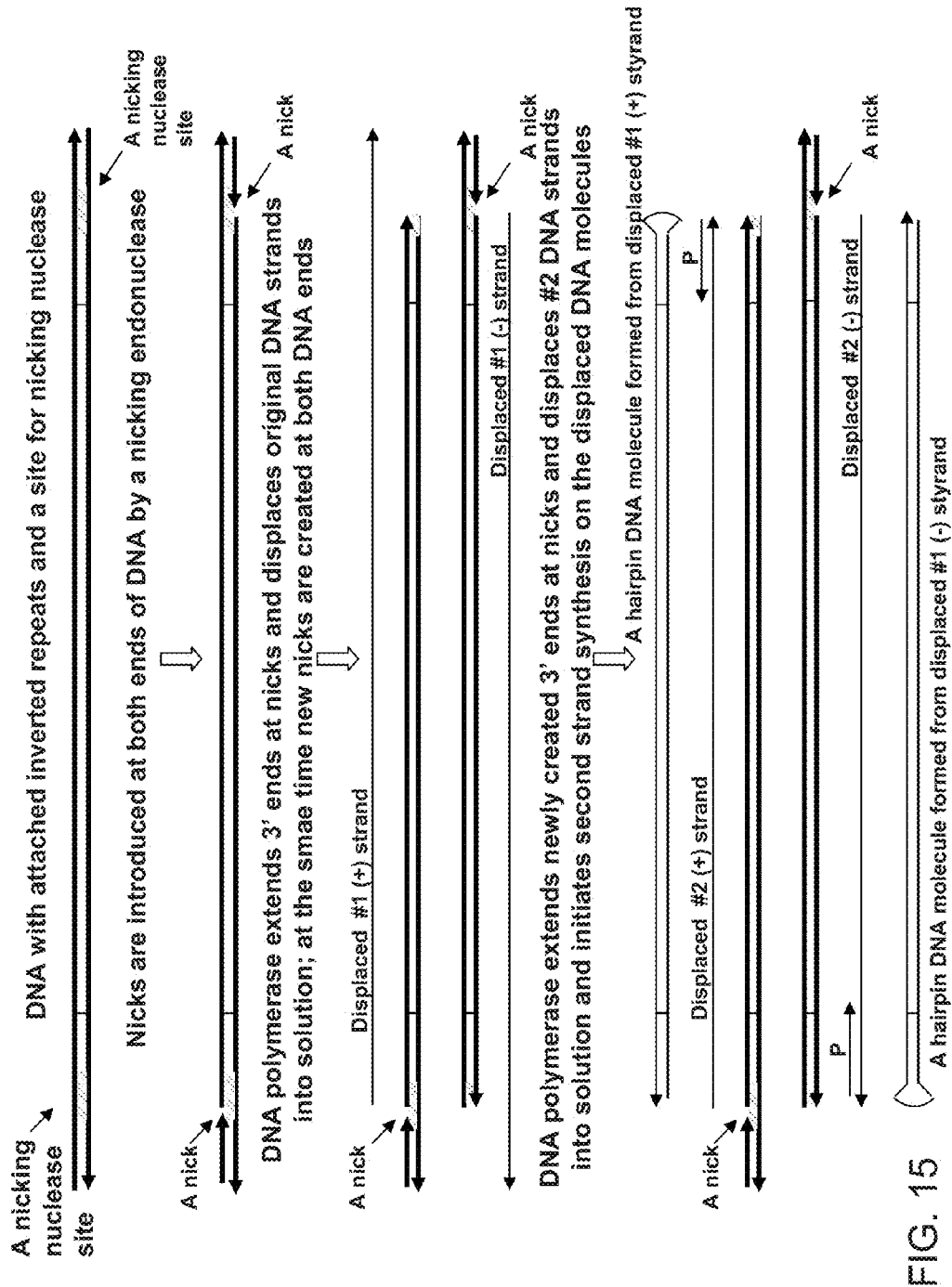
FIG. 15 illustrates the components and enzymatic reactions involved in exemplary one-step or two-step (after library synthesis) DNA amplification by strand displacement DNA synthesis using Enz-O-Mix reagents (Enz-O-Mix 3 and Enz-O-Mix 6 in FIGS. 19A and 19B, for example). The amplification is initiated and further maintained by the generation of a nick within the attached oligonucleotide sequence. The process linearly amplifies DNA and produces double stranded DNA molecules.
Figure 15:
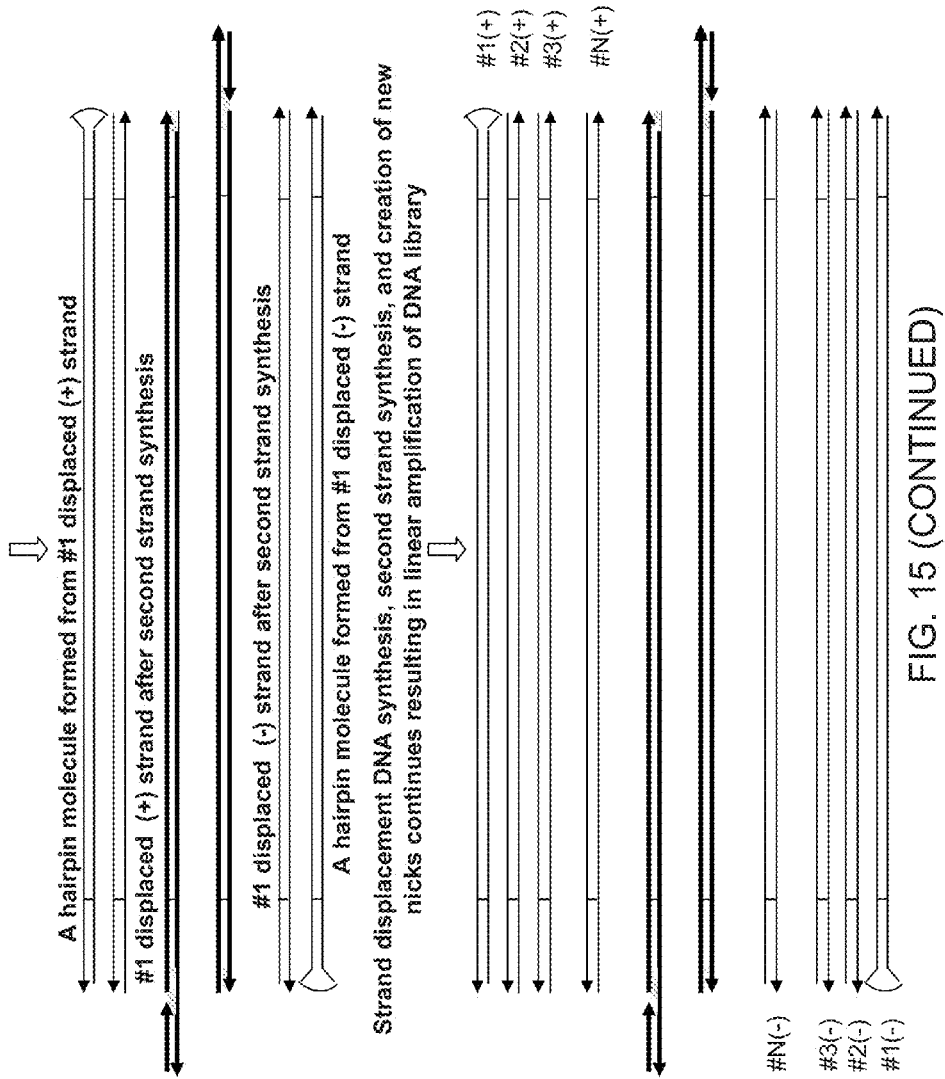

M. Enz-O-Mix Reagents and Procedures for One-Step Library Synthesis and One-Step Library Synthesis/Amplification Utilizing Strand Displacement DNA Amplification This embodiment is shown in FIG. 15 and illustrates exemplary components and enzymatic reactions involved in the process catalyzed by Enz-O-Mix reagents (Enz-O-Mix 3 and Enz-O-Mix 6, FIGS. 19A and 19B). The reagent Enz-O-Mix 3 can use fragmented (cell-free serum DNA or urine DNA, for example), while the reagent Enz-O-Mix 6 can utilize HMW DNA and synthesize a library of DNA fragments with the recognition sites for a nicking endonuclease (N.AlwI, N.BbvCIA, N.BbvCIB, Nb.Bpu10I, Nb.BsmI, N.Bst9I, N.BstNBI, etc.) at their ends to allow their subsequent amplification by strand displacement DNA synthesis. The presence of nicking endonuclease and strand displacing polymerase in the reagents Enz-O-Mix 3 and Enx-O-Mix 6 allows one to simultaneously synthesize and amplify DNA library by strand displacement DNA synthesis.

For example, the Enz-O-Mix reagent 3 (suitable for fragmented DNA) comprises a stem-loop oligonucleotide with a recognition sequence for a nicking nuclease; a primer P complementary at least partially to the stem region of a stem-loop oligonucleotide; a 3' proofreading DNA polymerase; a strand displacing DNA polymerase; T4 DNA ligase; a nicking endonuclease; Enz-O-Mix Universal Buffer; and dNTPs. T4 DNA polymerase "polishes" the DNA ends and the stem-loop oligonucleotide double-stranded stem-region. T4 ligase ligates the 3' end of the oligonucleotide to the 5' phosphate of the DNA, leaving a nick between the 3' end of DNA and the 5' end of the oligonucleotide double-stranded stem-region. DNA polymerase extends the available 3' DNA end toward the end of a stem-loop oligonucleotide and generates a library of DNA fragments with functional recognition site for a nicking endonuclease (N.AlwI, N.BbvCIA, N.BbvCIB, Nb.Bpu10I, Nb.BsmI, N.Bst9I, N.BstNBI, etc.) at their ends. DNA polymerase initiates multiple rounds of strand displacement DNA synthesis at nicks generated by a nicking nuclease, followed by synthesis of a second DNA strand (primed by primer P), producing double stranded DNA molecules and linearly amplifying DNA.

In the case of HMW DNA (Enz-O-Mix 6, FIG. 19B), the reaction requires a DNA fragmentation endonuclease (a restriction enzyme, DNase I, methylation-specific nuclease McrBC, benzonase, apoptotic endonuclease etc.), and all other components may be the same as described above for Enz-O-Mix 3.

Figure 16A:
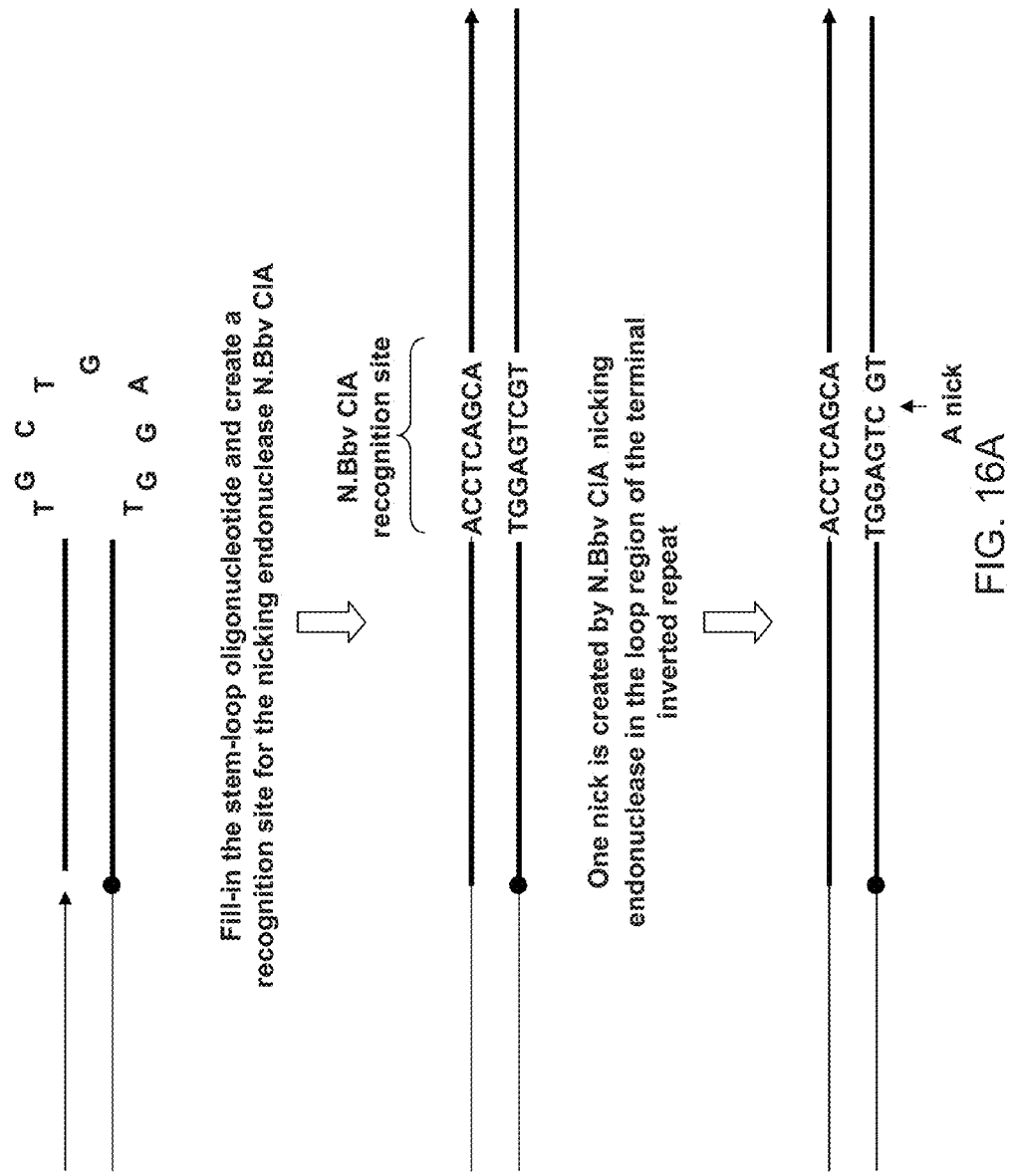
FIG. 16A shows the stem-loop oligonucleotide with the recognition sequence for the nicking endonuclease N. Bbv CIA located at the loop region. The enzyme can not cut the single stranded GCTGAGG region within the stem-loop oligonucleotide (not a recognizable structure) but it can nick it efficiently when the oligonucleotide is attached to a DNA end and adopts a canonical (double-stranded) Watson-Crick conformation.

N. Examples of Stem-Loop Adaptors with a Nicking Endonuclease Recognition Site Generated by DNA Synthesis FIG. 16A shows the stem-loop oligonucleotide with recognition sequence for the exemplary nicking endonuclease N.Bbv CIA located at the loop region. The enzyme can not nick the single stranded GCTGAGG region within the stem-loop oligonucleotide (an unrecognizable structure), but it will nick it efficiently when the oligonucleotide is attached to a DNA end and adopts a canonical (double-stranded) Watson-Crick conformation.

Figure 16B:
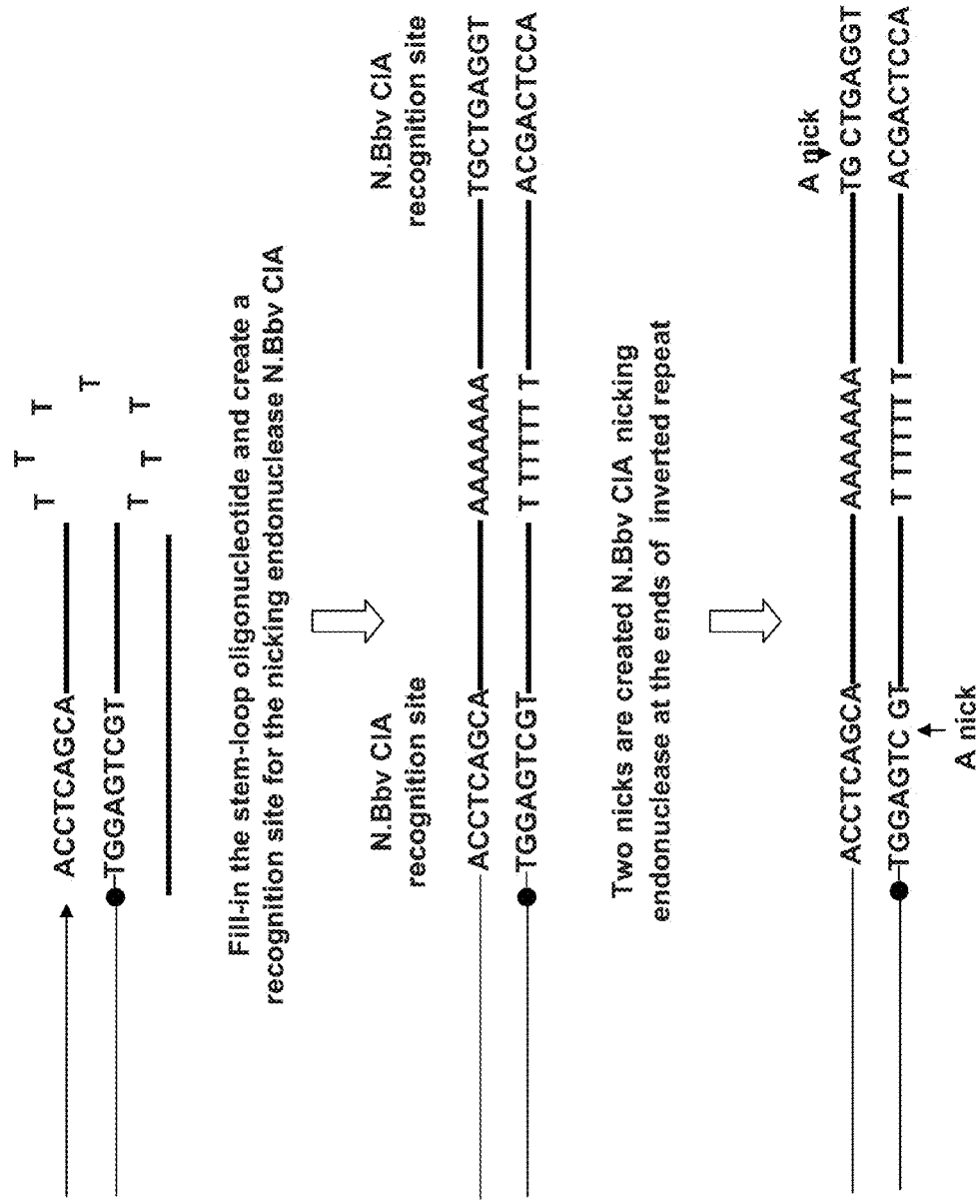
FIG. 16B shows a stem-loop oligonucleotide with the recognition sequence for the nicking endonuclease N. Bbv CIA located at the end of a stem region. The enzyme can not nick efficiently the GCTGAGG region within the stem-loop oligonucleotide (it is too close to the end) but it can nick it efficiently when the oligonucleotide is attached to a DNA end; the second site generated by attachment is not a good substrate for nicking (it is too close to the end).

FIG. 16B shows an exemplary stem-loop oligonucleotide with recognition sequence for the nicking endonuclease N.Bbv CIA located at the end of the stem region. The enzyme can not nick efficiently the terminally located TTAATTAA region within the stem-loop oligonucleotide, but it will nick it efficiently when the oligonucleotide is attached to a DNA end and the site acquires an internal location. A second nicking site, generated by the oligonucleotide attachment process, would have a terminal location and low nicking efficiency.

Figure 16C:
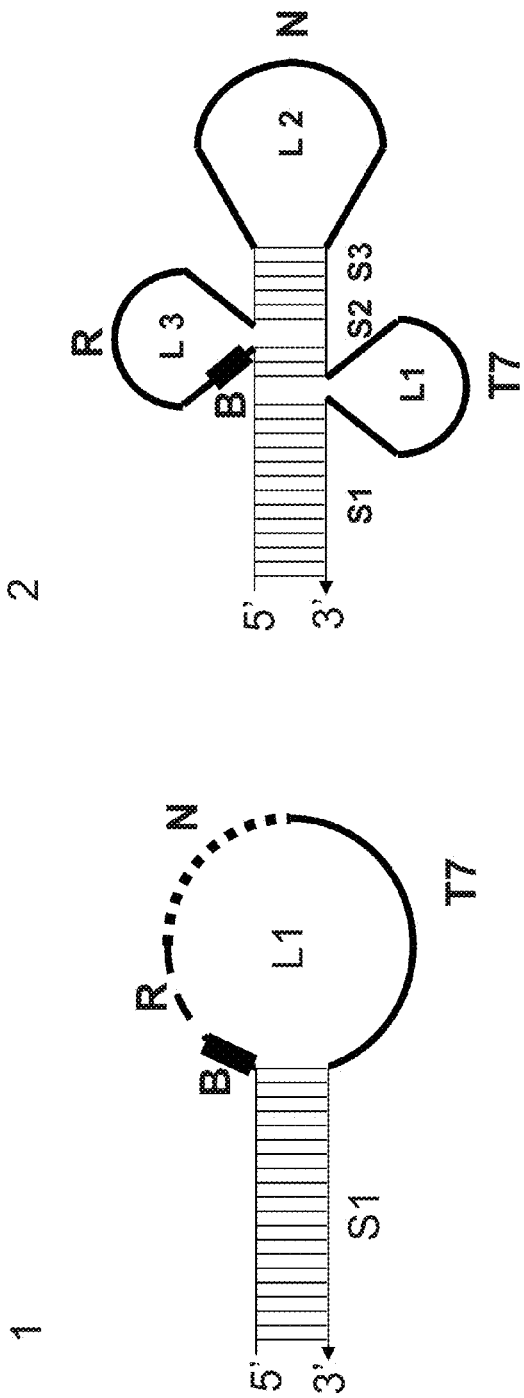
FIG. 16C shows two exemplary multifunctional stem-loop oligonucleotides with several regulatory elements within a single (1) or multiple (2) loop regions: T7 promoter sequence (that includes all regions necessary for transcription), recognition sequence N for a nicking endonuclease, recognition sequence for a restriction endonuclease, and a replication/transcription block region (a chemical modification or a string of 2-4 dU bases). A multifunctional stem loop oligonucleotide can support different types of DNA amplification, including PCR, isothermal amplification by transcription, isothermal amplification by strand displacement synthesis, or even a combination thereof and it can also facilitate other modifications, including DNA immobilization, DNA recombination, DNA cloning, and a combination thereof, for example.

FIG. 16C shows an exemplary stem-loop oligonucleotides 1 and 2 that contains several functional elements within the loop region including the recognition sequence for a nicking endonuclease. Multifunctional stem-loop oligonucleotide have several regulatory elements within the loop region: T7 promoter sequence (that includes all regions necessary for transcription); recognition sequence N for a nicking endonuclease (N.AlwI, N.BbvCIA, N.BbvCIB, Nb.Bpu10I, Nb.BsmI, N.Bst9I, N.BstNBI, etc.); recognition sequence for a restriction endonuclease; and a replication/transcription block region (a chemical modification or a string of 2-4 dU bases). The regulatory elements can reside within a single loop region (L1 in the stem-loop oligonucleotide 1), or be distributed across several loop regions (L1, L2, and L3 in the stem-loop oligonucleotide 2). A multifunctional stem-loop oligonucleotide can support different types of DNA amplification, including PCR, isothermal amplification by transcription, isothermal amplification by strand displacement synthesis, or even a combination thereof and can also facilitate modification such as DNA immobilization, DNA recombination, DNA cloning, or a combination thereof. Activation of the RNA transcription, DNA nicking, DNA double-stranded cleavage, and generation of the 5' overhang functions of the stem-loop adaptor occurs only upon its enzymatic processing and attachment to DNA ends.

Figure 17:
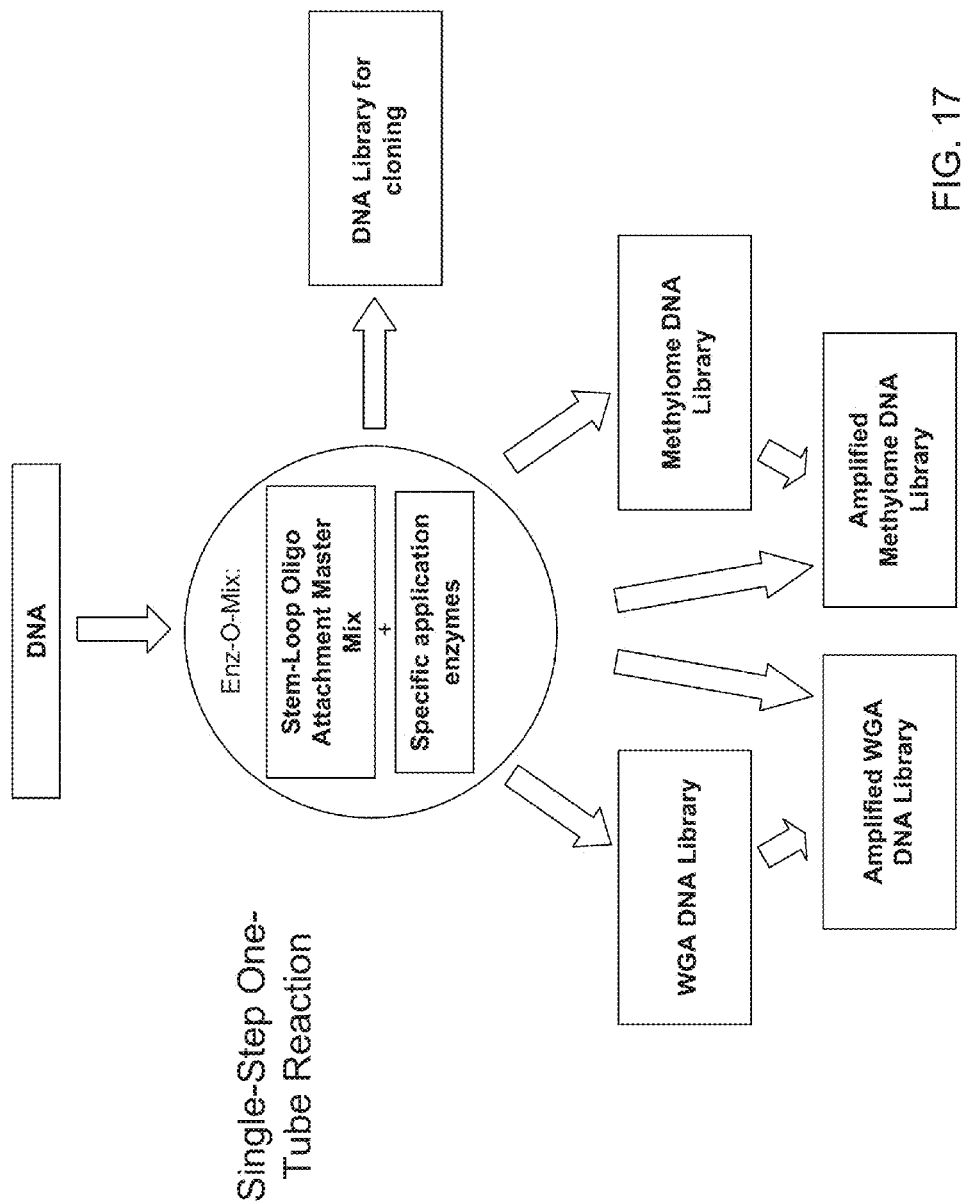
FIG. 17 shows generalization of the Enz-O-Mix method and demonstrates specific but exemplary applications.

O. Enz-O-Mix is a General Method for Synthesis and Amplification of DNA Libraries This embodiment of the present invention, as illustrated in FIG. 17, shows generalization of the Enz-O-Mix method and demonstrates its specific applications. When Enz-O-Mix reagent is combined with DNA and incubated at optimal temperature (for example, 37° C.) for a time necessary to complete the reaction (for example, 1 hour), although it can be more or less, it results in either a DNA library that can be amplified or cloned in a separate reaction, or a DNA library that is amplified isothermally during the incubation with the Enz-O-Mix reagent. For example, the exemplary products of reaction could be as follows: 1) a library of DNA fragments with universal sequence or sequences attached to the ends of DNA fragments so that it can be amplified by PCR (PCR WGA Library); 2) a library of DNA fragments with a promoter sequence attached at the ends of DNA fragments so that it can be amplified by transcription (Transcription WGA Library); 3) a Methylome Library, i.e. the library of adapted DNA fragments where all non-methylated CpG islands are eliminated (such as are described in U.S. patent application Ser. No. 11/071,864, filed Mar. 3, 2005, which is incorporated by reference herein in its entirety); 4) a library of DNA fragments with ready-to-clone sticky-end adaptors at the ends; 5) an amplified DNA library where the product is DNA or RNA; and/or 6) an amplified Methylome library where the product is DNA or RNA.

P. Stem-Loop Oligo Attachment Master Mix is a Key Component of all Enz-O-Mix Reactions This embodiment is shown in FIG. 18 and illustrates the components of four different Stem-Loop Oligo Attachment Master Mixes described in the invention and utilized in different Enz-O-Mix reactions involved in the DNA library synthesis. The Stem-Loop Oligo Attachment Master Mix is a key component of the Enz-O-Mix reaction, and it is present in all Enz-O-Mix reagents.

The exemplary Stem-Loop Oligo Attachment Master Mix I comprises a stem-loop oligonucleotide; a 3' proofreading DNA polymerase; a DNA ligase; Enz-O-Mix Universal Buffer; ATP; and dNTPs (see also FIG. 3 and FIG. 14).

The exemplary Stem-Loop Oligo Attachment Master Mix II comprises a stem-loop oligonucleotide with a non-replicable chemically introduced linker; a 3' proofreading DNA polymerase; a DNA ligase; Enz-O-Mix Universal Buffer; ATP; and dNTPs (see also FIG. 10A).

An exemplary Stem-Loop Oligo Attachment Master Mix III comprises a stem-loop oligonucleotide with a non-replicable enzymatically-introduced abasic linker; dU-glycosylase; a 3' proofreading DNA polymerase; a DNA ligase; Enz-O-Mix Universal Buffer; ATP; and dNTPs (see also FIG. 10B).

An exemplary Stem-Loop Oligo Attachment Master Mix IV comprises a stem-loop oligonucleotide with a cleavable site introduced by DNA replication; a site-specific endonuclease; a 3' proofreading DNA polymerase; a DNA ligase; Enz-O-Mix Universal Buffer; ATP; and dNTPs (see also FIG. 12 and FIGS. 14A, 14B, and 14C).

Q. Enz-O-Mix Reagents and Procedures for the One-Step Whole Genome Library Synthesis and Combined Whole Genome Library Synthesis-Amplification Whole Genome Amplification (WGA) is a process that is used to amplify total genomic DNA for many important research and diagnostic applications when the amount of DNA is limited. WGA is frequently preceded by a multi-step WGA library synthesis process. These embodiments describe the Enz-O-Mix reagents and procedures for the one-step Whole Genome Library synthesis and combined one-step, close-tube Whole Genome Library synthesis-amplification processes.

Figure 19A:
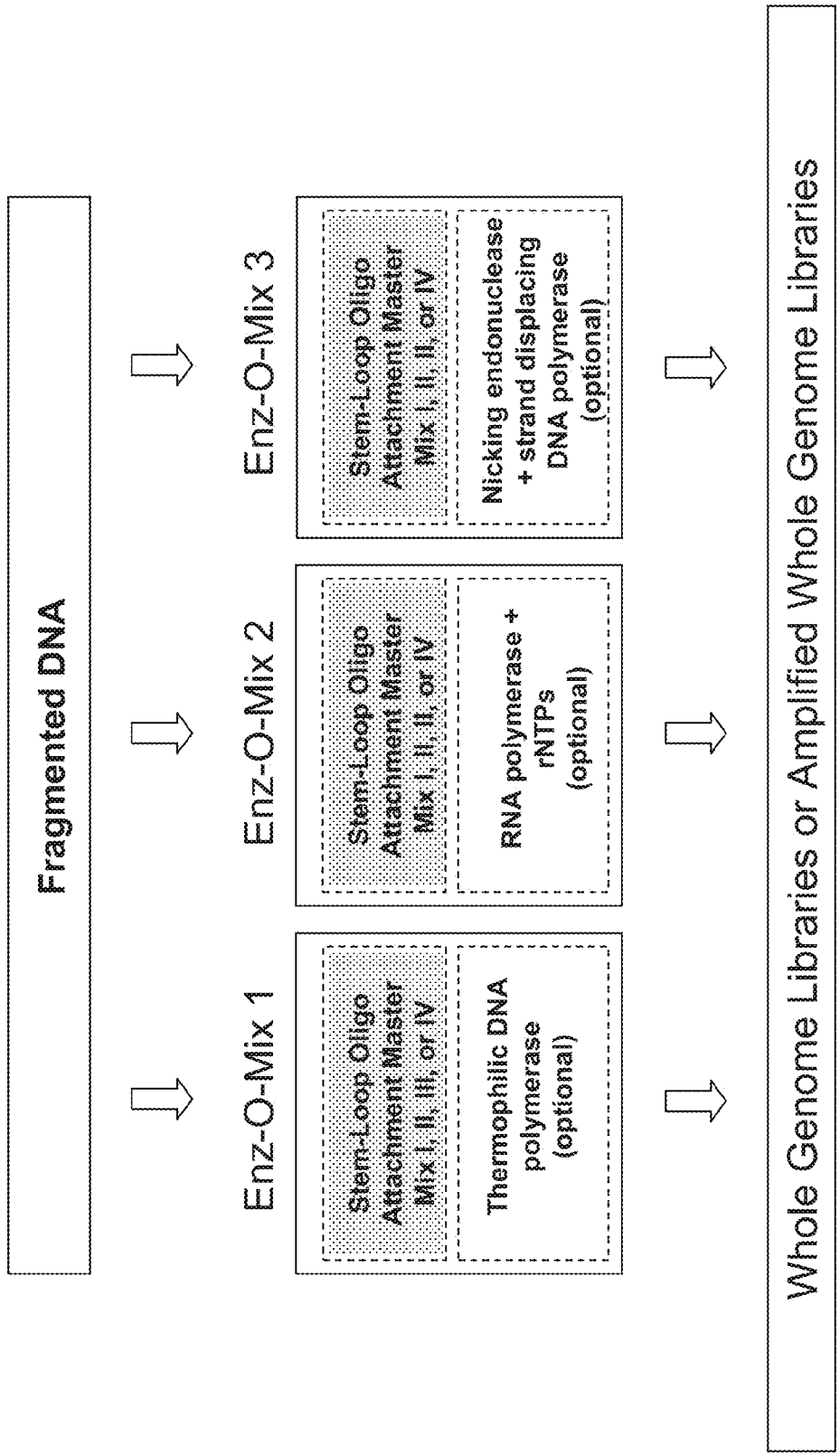
FIG. 19A schematically shows compositions of several Enz-O-Mix reagents, specifically, Enz-O-Mix 1, designed to convert fragmented DNA into a Whole Genome Library that can be amplified by PCR in an open, or close-tube format. Enz-O-Mix 2 and Enz-O-Mix 3 are designed to convert fragmented DNA into a Whole Genome Library that can be amplified after or during the Whole Genome Library synthesis by transcription and strand displacement, respectively.

FIG. 19A shows schematically compositions of three Enz-O-Mix reagents, specifically Enz-O-Mix 1, Enz-O-Mix 2, and Enz-O-Mix 3 designed to convert fragmented DNA into a Whole Genome Library competent for amplification by PCR, transcription, or strand displacement amplification, respectively.

Figure 30:
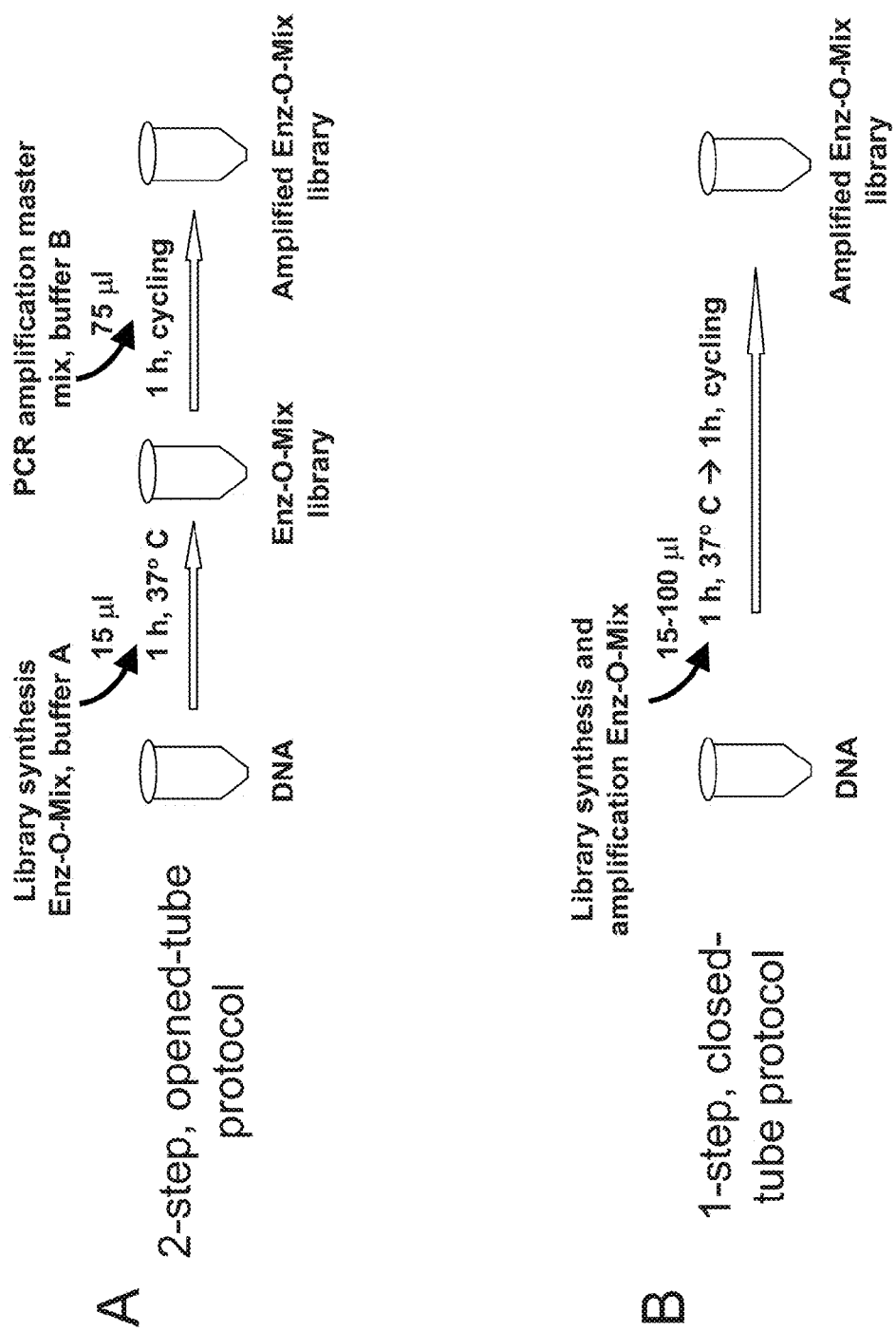
FIGS. 30A-30B compare two Enz-O-Mix library synthesis/PCR amplification processes (Enz-O-Mix 1 and Enz-O-Mix 4 from FIGS. 19A and 19B).

Reagent Enz-O-Mix 1 may comprise Stem-Loop Oligo Attachment Master Mixes shown in FIG. 18, and it could be also supplemented with a thermophilic DNA polymerase. The library prepared by the Enz-O-Mix 1 process can be used for PCR-mediated WGA in a open-tube (two-step process) or a close-tube (one-step process) formats (as shown in FIG. 30).

Reagent Enz-O-Mix 2 may comprise Stem-Loop Oligo Attachment Master Mixes shown in FIG. 18 (in this case a stem-loop oligonucleotide has the T7 promoter sequence in the loop or stem region in addition to other necessary base/backbone modifications), and it could be also supplemented with the T7 RNA polymerase and rNTPs. The Enz-O-Mix 2 can be used for a two-step transcription-mediated Whole Genome Amplification (when the library is prepared first, and then amplified) or for a one-step ithothermal amplification process when the Whole Genome library synthesis and its amplification by transcription occurs simultaneously (as shown in FIG. 6).

Reagent Enz-O-Mix 3 may comprise Stem-Loop Oligo Attachment Master Mixes shown in FIG. 18 (in this case, a stem-loop oligonucleotide has a recognition sequence for a nicking endonuclease in the loop or stem region in addition to other necessary base/backbone modifications). It could be also supplemented with a nicking endonuclease (N.AlwI, N.BbvCIA, N.BbvCIB, Nb.Bpu10I, Nb.BsmI, N.Bst9I, N.BstNBI, etc.), a strand displacing DNA polymerase (Klenow exo-, Phi 29, Bst I, etc.), and primer P (FIG. 15). The Enz-O-Mix 3 can be used for a two-step strand displacement-mediated Whole Genome Amplification (when the library is prepared first, and then amplified) or for a one-step ithothermal amplification process when the Whole Genome library synthesis and its amplification by a strand displacement synthesis occurs simultaneously (as shown in FIG. 15).

Figure 19B:
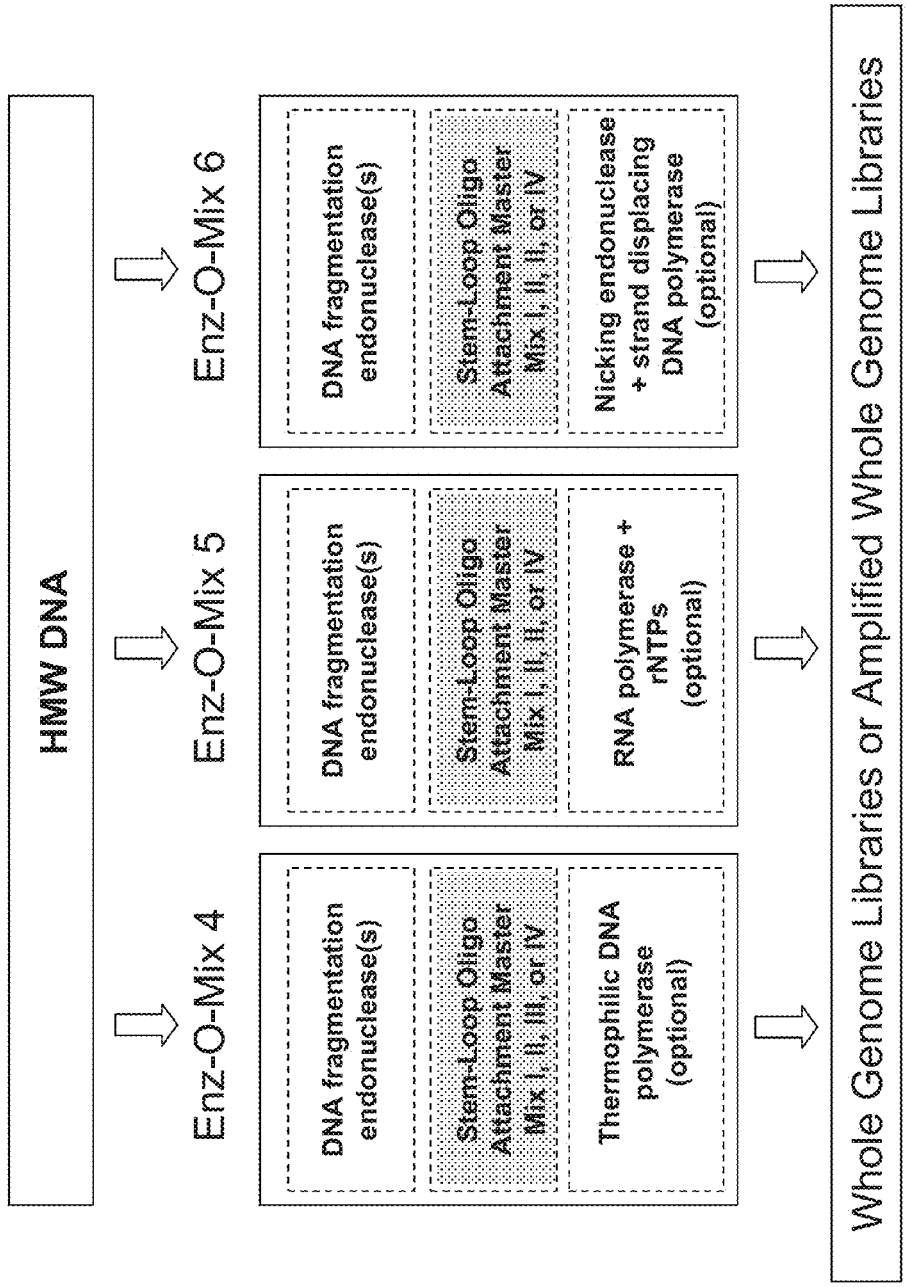
FIG. 19B shows schematically compositions of several Enz-O-Mix reagents, specifically, Enz-O-Mix 4, designed to convert HMW DNA into a Whole Genome Library that can be amplified by PCR in an open, or close-tube format. Enz-O-Mix 5 and Enz-O-Mix 6 are designed to convert fragmented DNA into a Whole Genome Library that can be amplified after or during the Whole Genome Library synthesis by transcription and strand displacement, respectively.

FIG. 19B shows schematically compositions of three Enz-O-Mix reagents, specifically Enz-O-Mix 4, Enz-O-Mix 5, and Enz-O-Mix 6 designed to convert high molecular DNA into a Whole Genome Library competent for amplification by PCR, transcription, or strand displacement amplification, respectively.

Reagent Enz-O-Mix 4 may comprise Stem-Loop Oligo Attachment Master Mixes shown in FIG. 18; it is also supplemented with a DNA fragmentation endonuclease such as restriction enzyme DNase I, Benzonase, methylation-specific nuclease McrBC, apoptotic endonuclease, etc.; and it could be also supplemented with a thermophilic DNA polymerase. The library prepared by the Enz-O-Mix 4 process can be used for PCR-mediated WGA in a open-tube (two-step process) or a close-tube (one-step process) formats (as shown in FIG. 30).

Reagent Enz-O-Mix 5 may comprise Stem-Loop Oligo Attachment Master Mixes shown in FIG. 18 (in this case, a stem-loop oligonucleotide has the T7 promoter sequence in the loop or stem region in addition to other necessary base/backbone modifications), and it is also supplemented with a DNA fragmentation endonuclease such as restriction enzyme DNase I, benzonase, methylation-specific nuclease McrBC, apoptotic endonuclease, etc.; and it could be also supplemented with RNA polymerase and rNTPs. The Enz-O-Mix 5 can be used for a two-step transcription-mediated Whole Genome Amplification of HMW DNA (when the library is prepared first, and then amplified) or for a one-step ithothermal amplification process when the Whole Genome library synthesis and its amplification by transcription occurs simultaneously (as shown in FIG. 6).

Reagent Enz-O-Mix 6 may comprise Stem-Loop Oligo Attachment Master Mixes shown in FIG. 18 (in this case, a stem-loop oligonucleotide has a recognition sequence for a nicking endonuclease in the loop or stem region in addition to other necessary base/backbone modifications), and it is supplemented with a DNA fragmentation endonuclease such as restriction enzyme, DNase I, benzonase, methylation-specific nuclease McrBC, apoptotic endonuclease. It could also be supplemented with a nicking endonuclease (N.AlwI, N.BbvCIA, N.BbvCIB, Nb.Bpu10I, Nb.BsmI, N.Bst9I, N.BstNBI, etc.); a strand displacing DNA polymerase (Klenow exo-, Phi 29, Bst I, etc.); and primer P (FIG. 15). The Enz-O-Mix 6 can be used for a two-step strand displacement-mediated Whole Genome Amplification of HMW DNA (when the library is prepared first, and then amplified) or for a one-step ithothermal amplification process when the Whole Genome library synthesis and its amplification by a strand displacement synthesis occurs simultaneously (as shown in FIG. 15).

R. Enz-O-Mix Reagents and Procedures for One-Step Whole Methylome Library Synthesis and Combined Whole Methylome Library Synthesis-Amplification Whole Methylome Amplification (WMA) is a process that was recently developed to amplify methylated DNA and suppress amplification of non-methylated genomic (promoter) regions for many important research and diagnostic applications, especially when the amount of DNA is limited (see, for example, U.S. patent application Ser. No. 11/071,864, filed Mar. 3, 2005, which is incorporated by reference herein in its entirety). In a standard protocol, WMA is preceded by a multi-step WMA library synthesis process. This embodiment describes the exemplary Enz-O-Mix reagents and procedures for the one-step Whole Methylome Library synthesis and combined Whole Methylome Library synthesis-amplification processes.

Figure 19C:
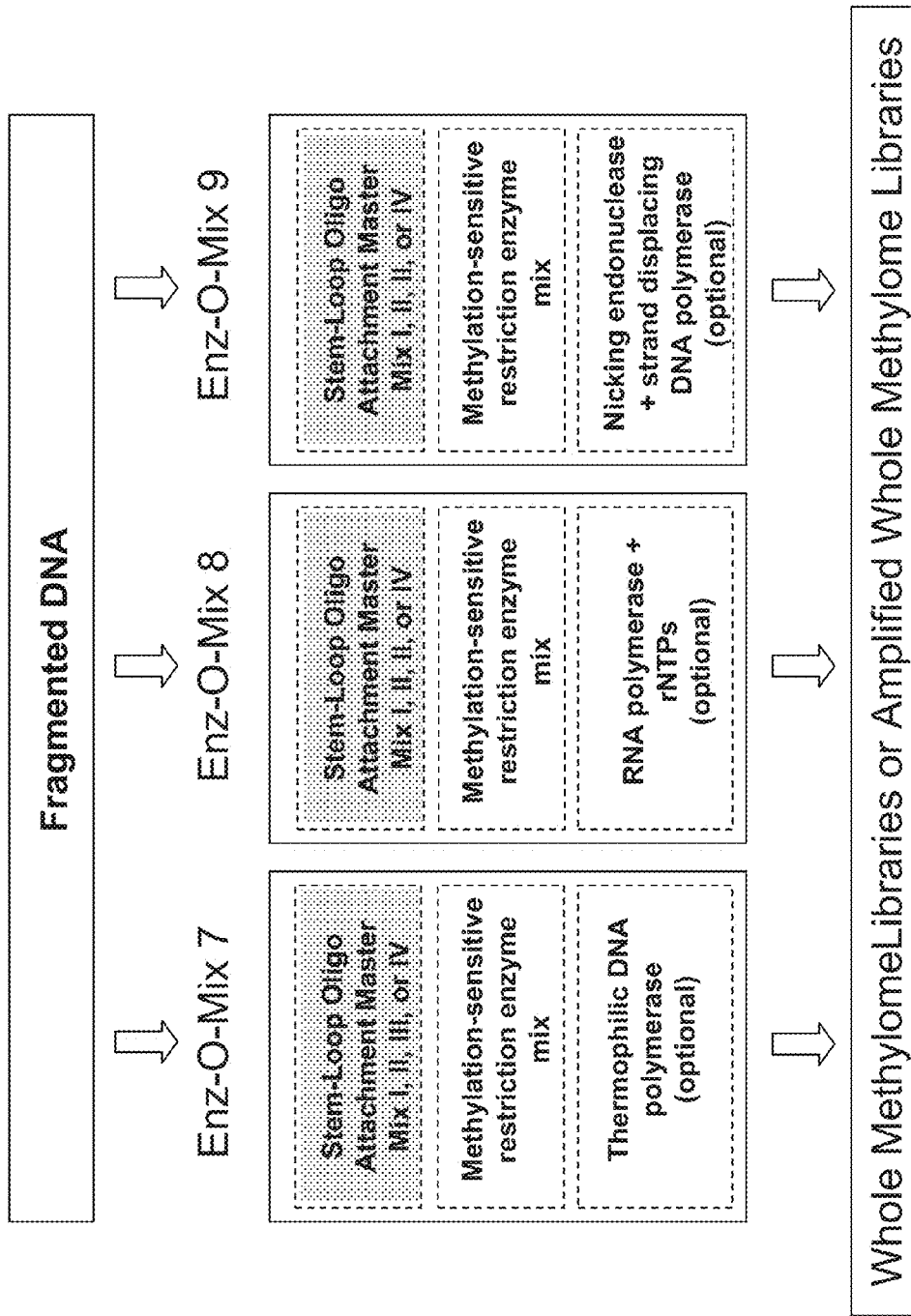
FIG. 19C shows schematically compositions of several Enz-O-Mix reagents, specifically, Enz-O-Mix 7, designed to convert fragmented DNA into a Whole Methylome Library that can be amplified by PCR. Enz-O-Mix 8 and Enz-O-Mix 9 are designed to convert fragmented DNA into a Whole Methylome Library that can be amplified after or during the Whole Methylome Library synthesis by transcription and strand displacement, respectively.

FIG. 19C shows schematically compositions of three Enz-O-Mix reagents, Enx-O-Mix 7, Enx-O-Mix 8, and Enx-O-Mix 9, designed to convert fragmented DNA into a Whole Methylome Library competent for amplification by PCR, transcription, or strand displacement, for example.

Reagent Enz-O-Mix 7 may comprise one of Stem-Loop Oligo Attachment Master Mixes shown in FIG. 18, and it is also supplemented with a mixture of several (about 5-about 12) methylation-sensitive restriction enzymes, such as Aci I, Acc II, Asp LE I, Ava I, Bce AI, Bsa HI, Bsh 1236 I, Bsi E1, Bsi SI, Bst FN I, Bst HH I, Bst UI, Cfo I, Hap II, Hga I, Hha I, HinP1 I, Hin 6I, Hpa II, Hpy 99I, Hpy CH4 IV, Hsp AI, Mvn I, and Ssi I, to produce a substantial fragmentation of all non-methylated CpG islands (see, for example, U.S. patent application Ser. No. 11/071,864, filed Mar. 3, 2005, which is incorporated by reference herein in its entirety). Reagent Enz-O-Mix 7 could be also supplemented with a thermophilic DNA polymerase. The Methylome library prepared by the Enz-O-Mix 7 process can be used for PCR-mediated WMA in a open-tube (two-step process) or a close-tube (one-step process) formats (as shown in FIG. 30).

Reagent Enz-O-Mix 8 may comprise Stem-Loop Oligo Attachment Master Mixes shown in FIG. 18 (in this case a stem-loop oligonucleotide has the T7 promoter sequence in the loop or stem region in addition to other necessary base/backbone modifications), and it is also supplemented with a mixture of several (about 5-about 12) methylation-sensitive restriction enzymes, such as Aci I, Acc II, Asp LE I, Ava I, Bce AI, Bsa HI, Bsh 1236 I, Bsi E1, Bsi SI, Bst FN I, Bst HH I, Bst UI, Cfo I, Hap II, Hga I, Hha I, HinP1 I, Hin 6I, Hpa II, Hpy 99I, Hpy CH4 IV, Hsp AI, Mvn I, and Ssi I, to produce a substantial fragmentation of all non-methylated CpG islands (U.S. patent application Ser. No. 11/071,864, filed Mar. 3, 2005, which is incorporated by reference herein in its entirety). Reagent Enz-O-Mix 8 could be also supplemented with T7 RNA polymerase and rNTPs. The Enz-O-Mix 8 can be used for a two-step transcription-mediated Whole Methylome Amplification (when the Whole Methylome library is prepared first, and then amplified) or for a one-step ithothermal amplification process when the Methylome library synthesis and its amplification by transcription occurs simultaneously.

Reagent Enz-O-Mix 9 may comprise Stem-Loop Oligo Attachment Master Mixes shown in FIG. 18 (in this case, a stem-loop oligonucleotide has a recognition sequence for a nicking endonuclease in the loop or stem region in addition to other necessary base/backbone modifications), and it is also supplemented with a mixture of several (about 5-12) methylation-sensitive restriction enzymes, such as Aci I, Acc II, Asp LE I, Ava I, Bce AI, Bsa HI, Bsh 1236 I, Bsi E1, Bsi SI, Bst FN I, Bst HH I, Bst UI, Cfo I, Hap II, Hga I, Hha I, HinP1 I, Hin 6I, Hpa II, Hpy 99I, Hpy CH4 IV, Hsp AI, Mvn I, and Ssi I, to produce a substantial fragmentation of all non-methylated CpG islands (see, for example, U.S. patent application Ser. No. 11/071,864, filed Mar. 3, 2005, which is incorporated by reference herein in its entirety). Reagent Enz-O-Mix 9 could be also supplemented with nicking endonuclease (N.AlwI, N.BbvCIA, N.BbvCIB, Nb.Bpu10I, Nb.BsmI, N.Bst9I, N.BstNBI, etc.), a strand displacing DNA polymerase (Klenow exo-, Phi 29, Bst I, etc.), and primer P (FIG. 15). The Enz-O-Mix 9 can be used for a two-step strand displacement-mediated Whole Methylome Amplification (when the library is prepared first, and then amplified) or for a one-step ithothermal amplification process when the Methylome library synthesis and its amplification by a strand displacement synthesis occurs simultaneously (as shown in FIG. 15).

Figure 19D:
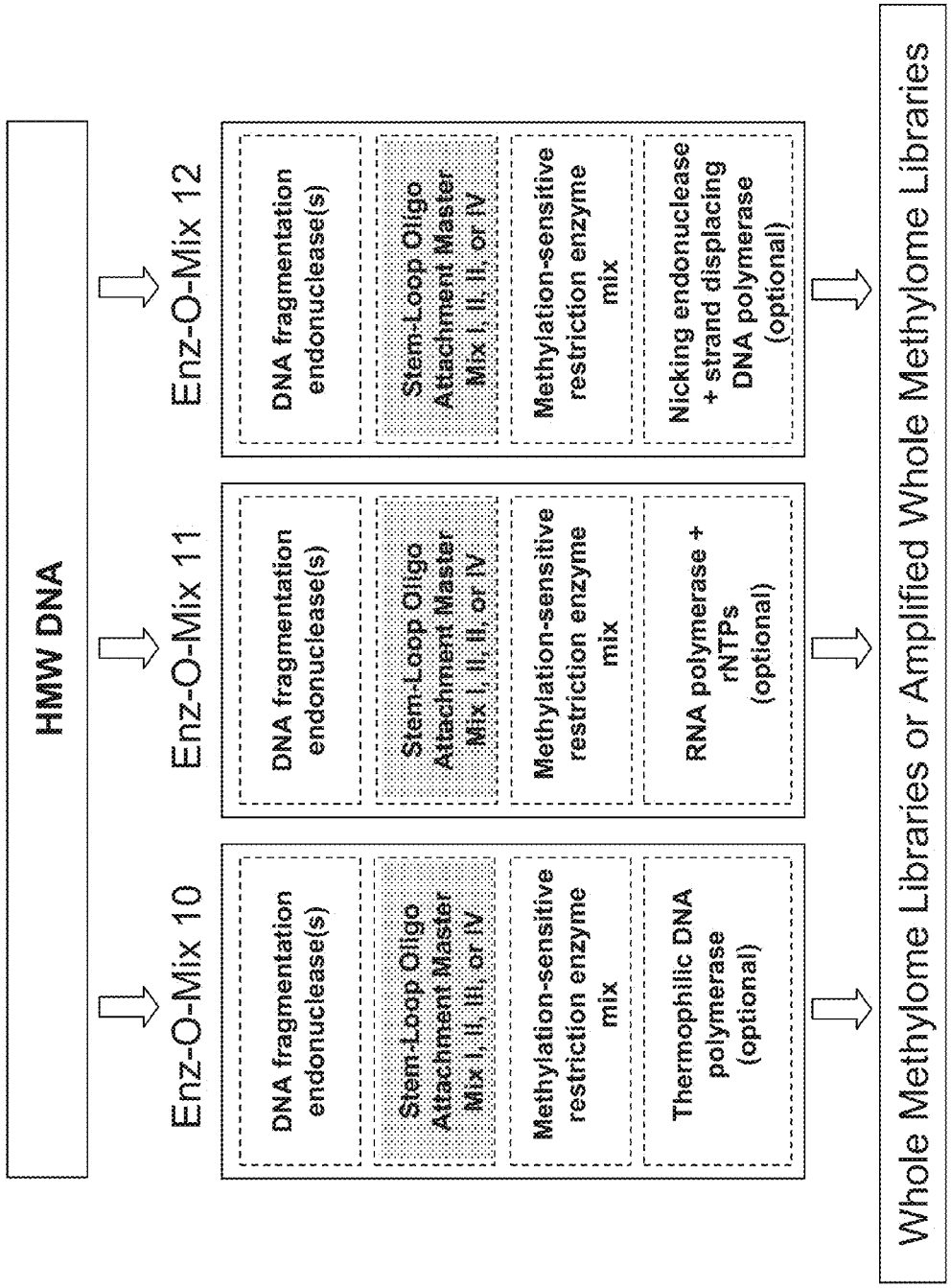
FIG. 19D shows schematically compositions of several Enz-O-Mix reagents, specifically, Enz-O-Mix 10, designed to convert HMW DNA into a Whole Methylome Library that can be amplified by PCR. Enz-O-Mix 11 and Enz-O-Mix 12 are designed to convert fragmented DNA into a Whole Methylome Library that can be amplified after or during the Whole Methylome Library synthesis by transcription and strand displacement, respectively.

FIG. 19D show schematically compositions of another three Enz-O-Mix reagents, Enx-O-Mix 10, Enx-O-Mix 11, and Enx-O-Mix 12, designed to convert HMW DNA into a Whole Methylome Library competent for amplification by PCR, transcription, or strand displacement, for example.

Reagent Enz-O-Mix 10 may comprise one of Stem-Loop Oligo Attachment Master Mixes shown in FIG. 18, and it is also supplemented with a DNA fragmentation endonuclease such as restriction enzyme, DNase I, benzonase, methylation-specific nuclease McrBC, apoptotic endonuclease, and a mixture of several (about 5-12) methylation-sensitive restriction enzymes, such as Aci I, Acc II, Asp LE I, Ava I, Bce AI, Bsa HI, Bsh 1236 I, Bsi E1, Bsi SI, Bst FN I, Bst HH I, Bst UI, Cfo I, Hap II, Hga I, Hha I, HinP1 I, Hin 6I, Hpa II, Hpy 99I, Hpy CH4 IV, Hsp AI, Mvn I, and Ssi I, to produce a substantial fragmentation of all non-methylated CpG islands (see, for example, U.S. patent application Ser. No. 11/071,864, filed Mar. 3, 2005, which is incorporated by reference herein in its entirety). It could be also supplemented with a thermophilic DNA polymerase. The Methylome library prepared by the Enz-O-Mix 10 process can be used for PCR-mediated WMA in a open-tube (two-step process) or a close-tube (one-step process) formats (as shown in FIG. 30).

Reagent Enz-O-Mix 11 may comprise Stem-Loop Oligo Attachment Master Mixes shown in FIG. 18 (in this case a stem-loop oligonucleotide has the T7 promoter sequence in the loop or stem region in addition to other necessary base/backbone modifications), and it is also supplemented with a DNA fragmentation endonuclease, such as restriction enzyme, DNase I, benzonase, methylation-specific nuclease McrBC, apoptotic endonuclease, etc.; and a mixture of several (about 5-about 12) methylation-sensitive restriction enzymes, such as Aci I, Acc II, Asp LE I, Ava I, Bce AI, Bsa HI, Bsh 1236 I, Bsi E1, Bsi SI, Bst FN I, Bst HH I, Bst UI, Cfo I, Hap II, Hga I, Hha I, HinP1 I, Hin 6I, Hpa II, Hpy 99I, Hpy CH4 IV, Hsp AI, Mvn I, and Ssi I, to produce a substantial fragmentation at all non-methylated CpG islands (see, for example, U.S. patent application Ser. No. 11/071,864, filed Mar. 3, 2005, which is incorporated by reference herein in its entirety). Reagent Enz-O-Mix 11 could be also supplemented with T7 RNA polymerase and rNTPs. The Enz-O-Mix 11 can be used for a two-step transcription-mediated Whole Methylome Amplification (when the Whole Methylome library is prepared first, and then amplified) or for a one-step ithothermal amplification process when the Methylome library synthesis and its amplification by transcription occurs simultaneously.

Reagent Enz-O-Mix 12 may comprise Stem-Loop Oligo Attachment Master Mixes shown in FIG. 18 (in this case, a stem-loop oligonucleotide has a recognition sequence for a nicking endonuclease in the loop or stem region in addition to other necessary base/backbone modifications), and it is also supplemented with a DNA fragmentation endonuclease, such as restriction enzyme, DNase I, benzonase, methylation-specific nuclease McrBC, apoptotic endonuclease; and a mixture of several (about 5-12) methylation-sensitive restriction enzymes, such as Aci I, Acc II, Asp LE I, Ava I, Bce AI, Bsa HI, Bsh 1236 I, Bsi E1, Bsi SI, Bst FN I, Bst HH I, Bst UI, Cfo I, Hap II, Hga I, Hha I, HinP1 I, Hin 6I, Hpa II, Hpy 99I, Hpy CH4 IV, Hsp AI, Mvn I, and Ssi I, to produce a substantial fragmentation of all non-methylated CpG islands (see, for example, U.S. patent application Ser. No. 11/071,864, filed Mar. 3, 2005, which is incorporated by reference herein in its entirety). Reagent Enz-O-Mix 12 could be also supplemented with nicking endonuclease (N.AlwI, N.BbvCIA, N.BbvCIB, Nb.Bpu10I, Nb.BsmI, N.Bst9I, N.BstNBI, etc.), a strand displacing DNA polymerase (Klenow exo-, Phi 29, Bst I, etc.), and primer P (FIG. 15). The Enz-O-Mix 12 can be used for a two-step strand displacement-mediated Whole Methylome Amplification (when the library is prepared first, and then amplified) or for a one-step ithothermal amplification process when the Methylome library synthesis and its amplification by a strand displacement synthesis occurs simultaneously (as shown in FIG. 15).

S. Enz-O-Mix Reagents and Procedures for the One-Step Whole Genome Library Synthesis for Cloning DNA cloning is a powerful tool for whole genome DNA sequencing and analysis of cDNA libraries, for example. In a standard process, DNA is randomly fragmented, repaired, attached to linkers, and then integrated into a vector. This embodiment describes the Enz-O-Mix reagents for the one-step preparation of DNA fragments with sticky ends that is easy to clone.

Figure 19E:
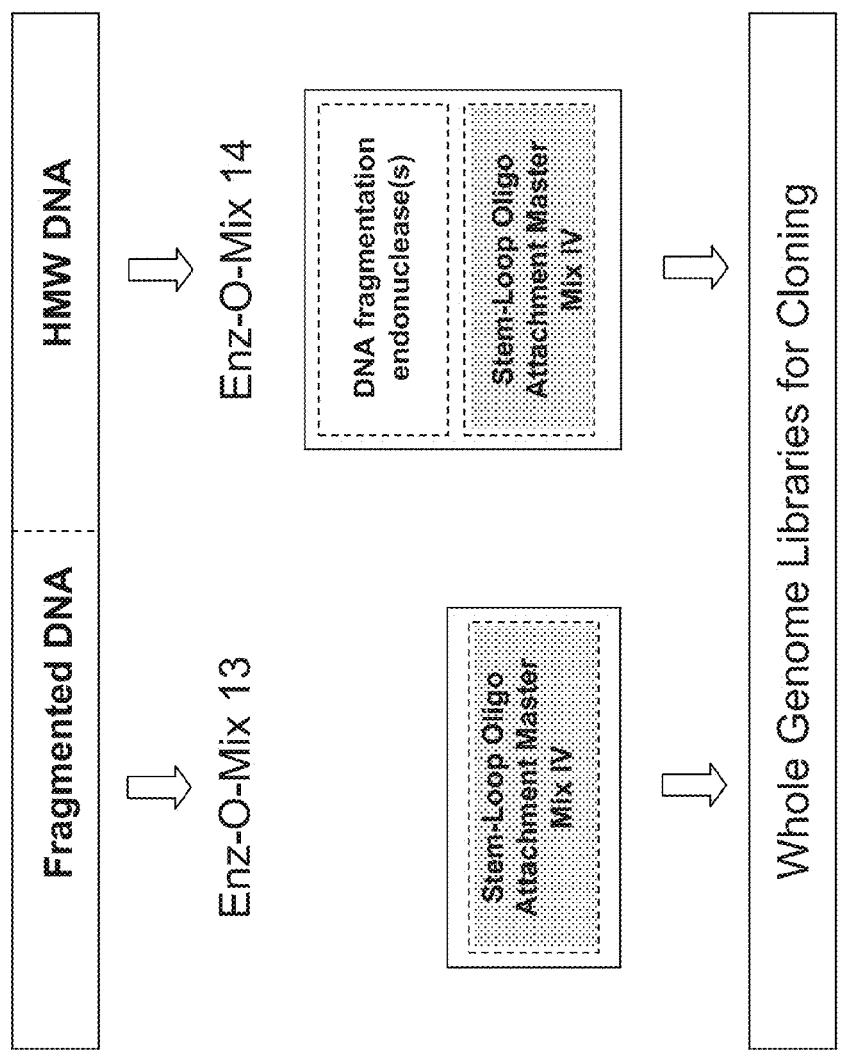
FIG. 19E shows schematically compositions of Enz-O-Mix reagents 13 and 14 designed to convert fragmented and HMW DNA, respectively, into a Whole Genome Library that can be directly cloned into an appropriate vector.

FIG. 19E shows schematically exemplary compositions of two Enz-O-Mix reagents designed to convert fragmented (Enz-O-Mix 13) or HMW DNA (Enz-O-Mix 14) into a Whole Genome Library for cloning.

Reagent Enz-O-Mix 13 may comprise a Stem-Loop Oligo Attachment Master Mix IV shown in FIG. 18, and it is the only component of the Enz-O-Mix 13 reagent. The library generated by the Enz-O-Mix 13 process can only utilize a fragmented DNA (for example, cell-free DNA from blood and/or urine, or DNA fragmented enzymatically or mechanically, for example) and be used for cloning.

Reagent Enz-O-Mix 14 may comprise a Stem-Loop Oligo Attachment Master Mix IV shown in FIG. 18 that is supplemented with a DNA fragmentation endonuclease, such as restriction enzyme, DNase I, benzonase, methylation-specific nuclease McrBC, apoptotic endonuclease, etc. The library generated by the Enz-O-Mix 14 process can utilize HMW DNA from any type of cells and tissues and be used for cloning.

Figure 20:
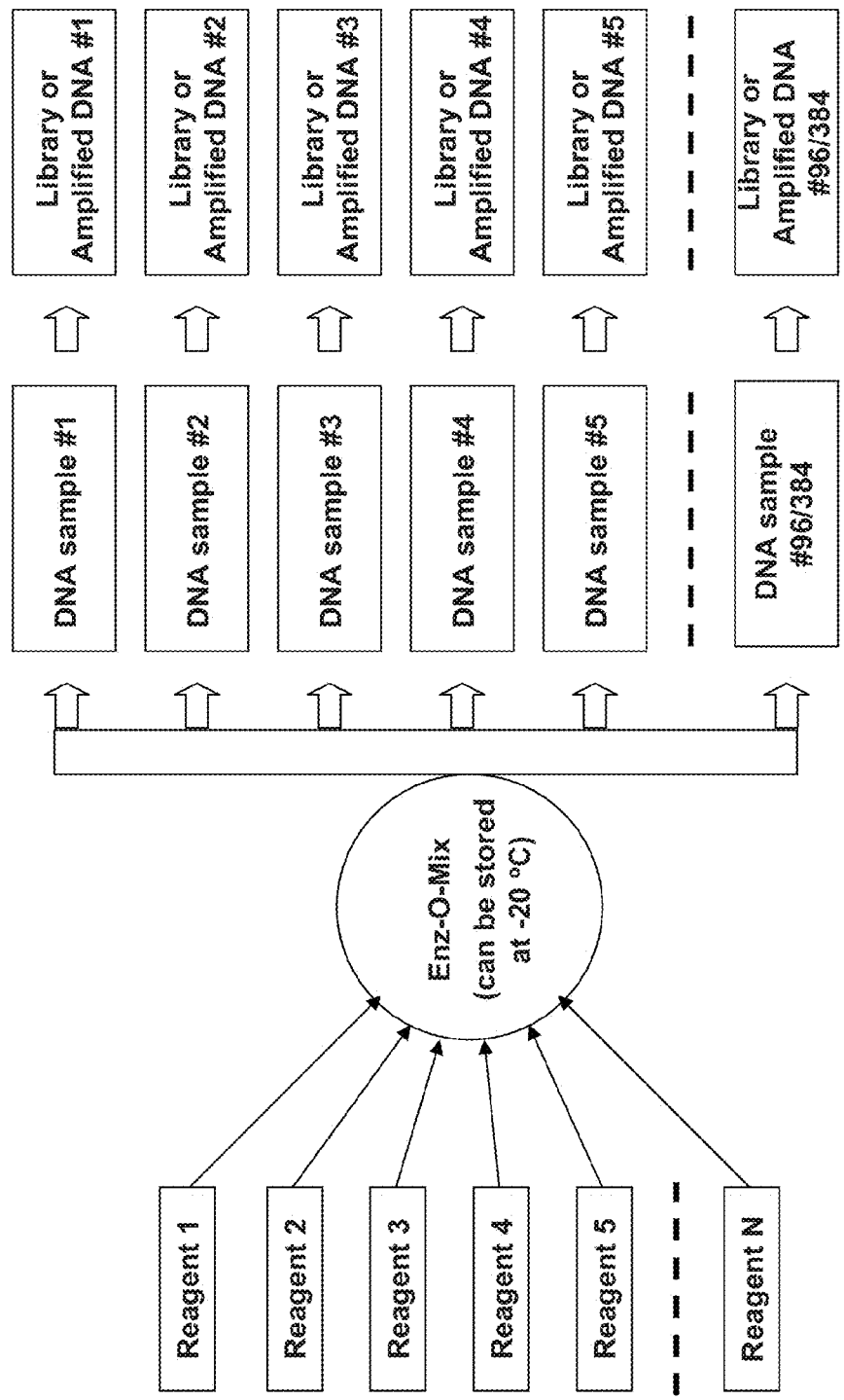
FIG. 20 illustrates assembly, storage and use of Enz-O-Mix reagent(s) as a kit in high throughput applications and clinical diagnostics, for example.

T. Enz-O-Mix Reagent Kits and their Use in High-Throughput Applications and Clinical Diagnostics In this embodiment of the present invention, as illustrated in FIG. 20, pre-assembled Enz-O-Mix reagents can be stored at −20° C. and used as ready-to-use kits.

Exemplary pre-assembled Enz-O-Mix 1 comprises all major components of the reaction, such as a stem-loop oligonucleotide; DNA polymerase; a DNA ligase; dU-glycosylase (when the hairpin non-replicable region is generated by abasic sites); a hairpin-specific endonuclease (when the hairpin has a cleavable site generated during oligonucleotide attachment process); thermophilic DNA polymerase (close-tube WGA library synthesis/PCR-mediated amplification reaction); ATP; and dNTPs.

Exemplary pre-assembled Enz-O-Mix 2 comprises a stem-loop oligonucleotide with a promoter sequence in a stem or loop region; DNA polymerase; a DNA ligase; dU-glycosylase (when the non-replicable region is formed by abasic sites); a site-specific endonuclease (when the stem-loop oligonucleotide has a cleavable site created during oligonucleotide attachment process); ATP; and dNTPs; In the case of close-tube, isothermal library synthesis/transcription-mediated amplification reaction it also comprises RNA polymerase and rNTPs.

Exemplary pre-assembled Enz-O-Mix 3 may comprise a stem-loop oligonucleotide with a nicking endonuclease sequence in a stem or a loop region; DNA polymerase; a DNA ligase; dU-glycosylase (when the non-replicable region is formed by abasic sites); a site-specific endonuclease (when the stem-loop oligonucleotide has a cleavable site generated during oligonucleotide attachment process); a DNA fragmentation endonuclease, such as restriction enzyme(s), DNase I, Benzonase, methylation-specific nuclease McrBC, apoptotic endonuclease etc.; ATP; and dNTP, In the case of close-tube, isothermal library synthesis/strand displacement-mediated amplification reaction it also comprises a nicking endonuclease (N.AlwI, N.BbvCIA, N.BbvCIB, Nb.Bpu10I, Nb.BsmI, N.Bst9I, N.BstNBI, etc.); a strand displacing DNA polymerase (Klenow exo-, Phi 29, Bst I, etc.); and a primer.

Exemplary pre-assembled Enz-O-Mix 4 may comprise all major components of the reaction, such as a stem-loop oligonucleotide; DNA polymerase; a DNA ligase; dU-glycosylase (when the hairpin non-replicable region is created by abasic sites); a hairpin-specific endonuclease (when the hairpin has a cleavable site created during oligonucleotide attachment process); a DNA fragmentation endonuclease such as restriction enzyme, DNase I, Benzonase, methylation-specific nuclease McrBC, apoptotic endonuclease; thermophilic DNA polymerase (close-tube WGA library synthesis/PCR-mediated amplification reaction); ATP; and dNTPs.

Exemplary pre-assembled Enz-O-Mix 5 may comprise a stem-loop oligonucleotide with a promoter sequence in a stem or loop region; DNA polymerase; DNA ligase; dU-glycosylase (when the non-replicable region is formed by abasic sites); a site-specific endonuclease (when the stem-loop oligonucleotide has a cleavable site created during the oligonucleotide attachment process); a DNA fragmentation endonuclease, such as restriction enzyme, DNase I, benzonase, methylation-specific nuclease McrBC, apoptotic endonuclease, etc.; ATP; and dNTPs. In the case of close-tube, isothermal library synthesis/transcription-mediated amplification reaction it also comprises RNA polymerase and rNTPs.

Exemplary pre-assembled Enz-O-Mix 6 comprises a stem-loop oligonucleotide with a nicking endonuclease sequence in a stem or a loop region, DNA polymerase, a DNA ligase, dU-glycosylase (when the non-replicable region is formed by abasic sites), a site-specific endonuclease (when the stem-loop oligonucleotide has a cleavable site created during oligonucleotide attachment process), a DNA fragmentation endonuclease such as restriction enzyme(s), DNase I, Benzonase, methylation-specific nuclease McrBC, apoptotic endonuclease; ATP; and dNTPs. In the case of close-tube, isothermal library synthesis/strand displacement-mediated amplification reaction it also comprises a nicking endonuclease (N.AlwI, N.BbvCIA, N.BbvCIB, Nb.Bpu10I, Nb.BsmI, N.Bst9I, N.BstNBI, etc.); a strand displacing DNA polymerase (Klenow exo-, Phi 29, Bst I, etc.); and a primer.

Exemplary pre-assembled Enz-O-Mix 7 may comprise all major components of the reaction, such as a stem-loop oligonucleotide; DNA polymerase; T4 DNA ligase; dU-glycosylase (when the hairpin non-replicable region is created by abasic sites); a hairpin-specific endonuclease (when the hairpin has a cleavable site created during oligonucleotide attachment process); a mixture of several (about 5-about 12) methylation-sensitive restriction enzymes, such as Aci I, Acc II, Asp LE I, Ava I, Bce AI, Bsa HI, Bsh 1236 I, Bsi E1, Bsi SI, Bst FN I, Bst HH I, Bst UI, Cfo I, Hap II, Hga I, Hha I, HinP1 I, Hin 6I, Hpa II, Hpy 99I, Hpy CH4 IV, Hsp AI, Mvn I, and Ssi I, to produce a substantial fragmentation at all non-methylated CpG islands (see, for example, U.S. patent application Ser. No. 11/071,864, filed Mar. 3, 2005, which is incorporated by reference herein in its entirety); thermophilic DNA polymerase (close-tube WMA library synthesis/PCR-mediated amplification reaction); ATP; and dNTPs.

Exemplary pre-assembled Enz-O-Mix 8 may comprise a stem-loop oligonucleotide with a promoter sequence in a stem or loop region; DNA polymerase; a DNA ligase; dU-glycosylase (when the non-replicable region is formed by abasic sites); a site-specific endonuclease (when the stem-loop oligonucleotide has a cleavable site created during the oligonucleotide attachment process); a mixture of several (about 5-about 12) methylation-sensitive restriction enzymes, such as Aci I, Acc II, Asp LE I, Ava I, Bce AI, Bsa HI, Bsh 1236 I, Bsi E1, Bsi SI, Bst FN I, Bst HH I, Bst UI, Cfo I, Hap II, Hga I, Hha I, HinP1 I, Hin 6I, Hpa II, Hpy 99I, Hpy CH4 IV, Hsp AI, Mvn I, and Ssi I, to produce a substantial fragmentation at all non-methylated CpG islands (see, for example, U.S. patent application Ser. No. 11/071, 864, filed Mar. 3, 2005, which is incorporated by reference herein in its entirety); ATP; and dNTPs. In the case of close-tube, isothermal library synthesis/transcription-mediated amplification reaction it also comprises RNA polymerase and rNTPs.

Exemplary pre-assembled Enz-O-Mix 9 may comprise a stem-loop oligonucleotide with a nicking endonuclease sequence in a stem or a loop region; DNA polymerase; a DNA ligase; dU-glycosylase (when the non-replicable region is formed by abasic sites); a site-specific endonuclease (when the stem-loop oligonucleotide has a cleavable site created during oligonucleotide attachment process); a DNA fragmentation endonuclease, such as restriction enzyme(s), DNase I, Benzonase, methylation-specific nuclease McrBC, apoptotic endonuclease, etc.; a mixture of several (about 5-about 12) methylation-sensitive restriction enzymes, such as Aci I, Acc II, Asp LE I, Ava I, Bce AI, Bsa HI, Bsh 1236 I, Bsi E1, Bsi SI, Bst FN I, Bst HH I, Bst UI, Cfo I, Hap II, Hga I, Hha I, HinP1 I, Hin 6I, Hpa II, Hpy 99I, Hpy CH4 IV, Hsp AI, Mvn I, and Ssi I, to produce a substantial fragmentation at all non-methylated CpG islands (see, for example, U.S. patent application Ser. No. 11/071, 864, filed Mar. 3, 2005, which is incorporated by reference herein in its entirety); ATP; and dNTPs. In the case of close-tube, isothermal library synthesis/strand displacement-mediated amplification reaction it also comprises a nicking endonuclease (N.AlwI, N.BbvCIA, N.BbvCIB, Nb.Bpu10I, Nb.BsmI, N.Bst9I, N.BstNBI, etc.); a strand displacing DNA polymerase (Klenow exo-, Phi 29, Bst I, etc.); and a primer.

Exemplary pre-assembled Enz-O-Mix 10 may comprise all major components of the reaction, such as a stem-loop oligonucleotide; DNA polymerase; a DNA ligase; dU-glycosylase (when the hairpin non-replicable region is created by abasic sites); a hairpin-specific endonuclease (when the hairpin has a cleavable site created during oligonucleotide attachment process); a DNA fragmentation endonuclease, such as restriction enzyme, DNase I, Benzonase, methylation-specific nuclease McrBC, apoptotic endonuclease, etc.; a mixture of several (about 5-about 12) methylation-sensitive restriction enzymes, such as Aci I, Acc II, Asp LE I, Ava I, Bce AI, Bsa HI, Bsh 1236 I, Bsi E1, Bsi SI, Bst FN I, Bst HH I, Bst UI, Cfo I, Hap II, Hga I, Hha I, HinP1 I, Hin 6I, Hpa II, Hpy 99I, Hpy CH4 IV, Hsp AI, Mvn I, and Ssi I, to produce a substantial fragmentation at all non-methylated CpG islands (see, for example, U.S. patent application Ser. No. 11/071,864, filed Mar. 3, 2005, which is incorporated by reference herein in its entirety); thermophilic DNA polymerase (close-tube WGA library synthesis/PCR-mediated amplification reaction); ATP; and dNTPs.

Exemplary pre-assembled Enz-O-Mix 11 may comprise a stem-loop oligonucleotide with a promoter sequence in a stem or loop region; DNA polymerase; a DNA ligase; dU-glycosylase (when the non-replicable region is formed by abasic sites); a site-specific endonuclease (when the stem-loop oligonucleotide has a cleavable site created during oligonucleotide attachment process); a DNA fragmentation endonuclease, such as restriction enzyme, DNase I, benzonase, methylation-specific nuclease McrBC, apoptotic endonuclease; a mixture of several (about 5-12) methylation-sensitive restriction enzymes, such as Aci I, Acc II, Asp LE I, Ava I, Bce AI, Bsa HI, Bsh 1236 I, Bsi E1, Bsi SI, Bst FN I, Bst HH I, Bst UI, Cfo I, Hap II, Hga I, Hha I, HinP1 I, Hin 6I, Hpa II, Hpy 99I, Hpy CH4 IV, Hsp AI, Mvn I, and Ssi I, to produce a substantial fragmentation at all non-methylated CpG islands (see, for example, U.S. patent application Ser. No. 11/071,864, filed Mar. 3, 2005, which is incorporated by reference herein in its entirety); ATP; and dNTPs. In the case of close-tube, isothermal library synthesis/transcription-mediated amplification reaction it also comprises RNA polymerase and rNTPs.

Exemplary pre-assembled Enz-O-Mix 12 may comprise a stem-loop oligonucleotide with a nicking endonuclease sequence in a stem or a loop region; DNA polymerase; a DNA ligase; dU-glycosylase (when the non-replicable region is formed by abasic sites); a site-specific endonuclease (when the stem-loop oligonucleotide has a cleavable site created during oligonucleotide attachment process); a DNA fragmentation endonuclease, such as restriction enzyme(s), DNase I, benzonase, methylation-specific nuclease McrBC, apoptotic endonuclease; a mixture of several (about 5-about 12) methylation-sensitive restriction enzymes, such as Aci I, Acc II, Asp LE I, Ava I, Bce AI, Bsa HI, Bsh 1236 I, Bsi E1, Bsi SI, Bst FN I, Bst HH I, Bst UI, Cfo I, Hap II, Hga I, Hha I, HinP1 I, Hin 6I, Hpa II, Hpy 99I, Hpy CH4 IV, Hsp AI, Mvn I, and Ssi I, to produce a substantial fragmentation at all non-methylated CpG islands (see, for example, U.S. patent application Ser. No. 11/071,864, filed Mar. 3, 2005, which is incorporated by reference herein in its entirety); ATP; and dNTPs. In the case of close-tube, isothermal library synthesis/strand displacement-mediated amplification reaction it also comprises a nicking endonuclease (N.AlwI, N.BbvCIA, N.BbvCIB, Nb.Bpu10I, Nb.BsmI, N.Bst9I, N.BstNBI, etc.) a strand displacing DNA polymerase (Klenow exo-, Phi 29, Bst I, etc.); and a primer.

Kits comprising the exemplary Enz-O-Mixes described above may be supplied with the Enz-O-Mix Universal Buffer. When used in high-throughput applications and clinical diagnostics, the Enz-O-Mix reagent is first diluted by the Enz-O-Mix Universal Buffer, aliquoted into microplate wells, pre-incubated at the reaction temperature (for example, about 37° C.) for a few minutes, supplemented with DNA, and incubated at the reaction temperature for about 1-about 16 h.

FIG. 20 demonstrates an exemplary application of the Enz-O-Mix kits for high-throughput library preparation/amplification in the 96- or 384-well format.

U. Enz-O-Mix Reaction Optimization Procedures

In this embodiment, as shown in FIG. 21, there are exemplary procedures for identifying the most optimal parameters for any Enz-O-Mix process using real-time PCR to monitor amplification of the generated library, or a direct fluorescent detection of the amplified product in the case of combined isothermal library synthesis-amplification process.

Figure 21A:
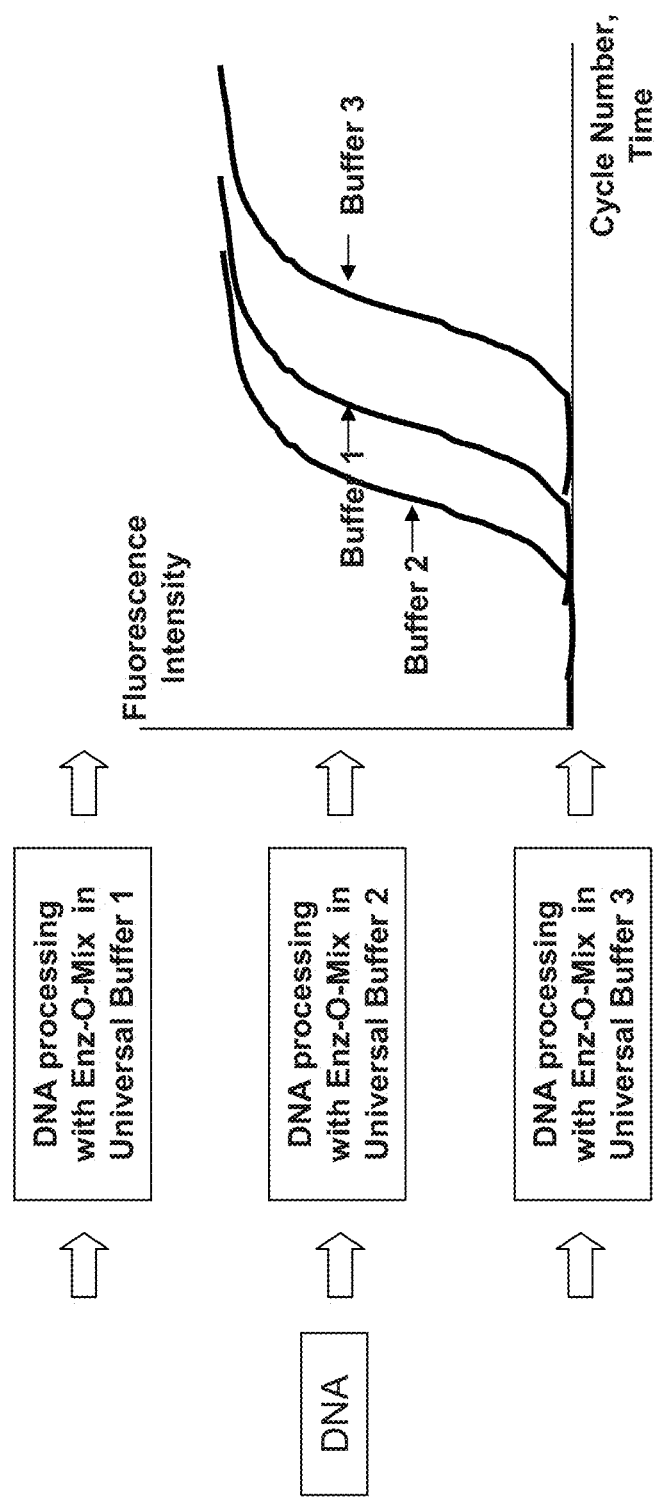
FIG. 21A demonstrates the optimization process for Enz-O-Mix Universal Buffer using real-time PCR to monitor amplification of the generated library.

FIG. 21A illustrates the procedure for optimization of the Enz-O-Mix Universal Buffer. Three specific but exemplary buffers are utilized, including Universal Buffers 1, 2 and 3. Buffer 2 results in the early WGA amplification curve, suggesting that the multi-enzymatic reaction was more efficient in this buffer, and the Universal Buffer 2 is particularly suitable for the Enz-O-Mix reaction.

Figure 21B:
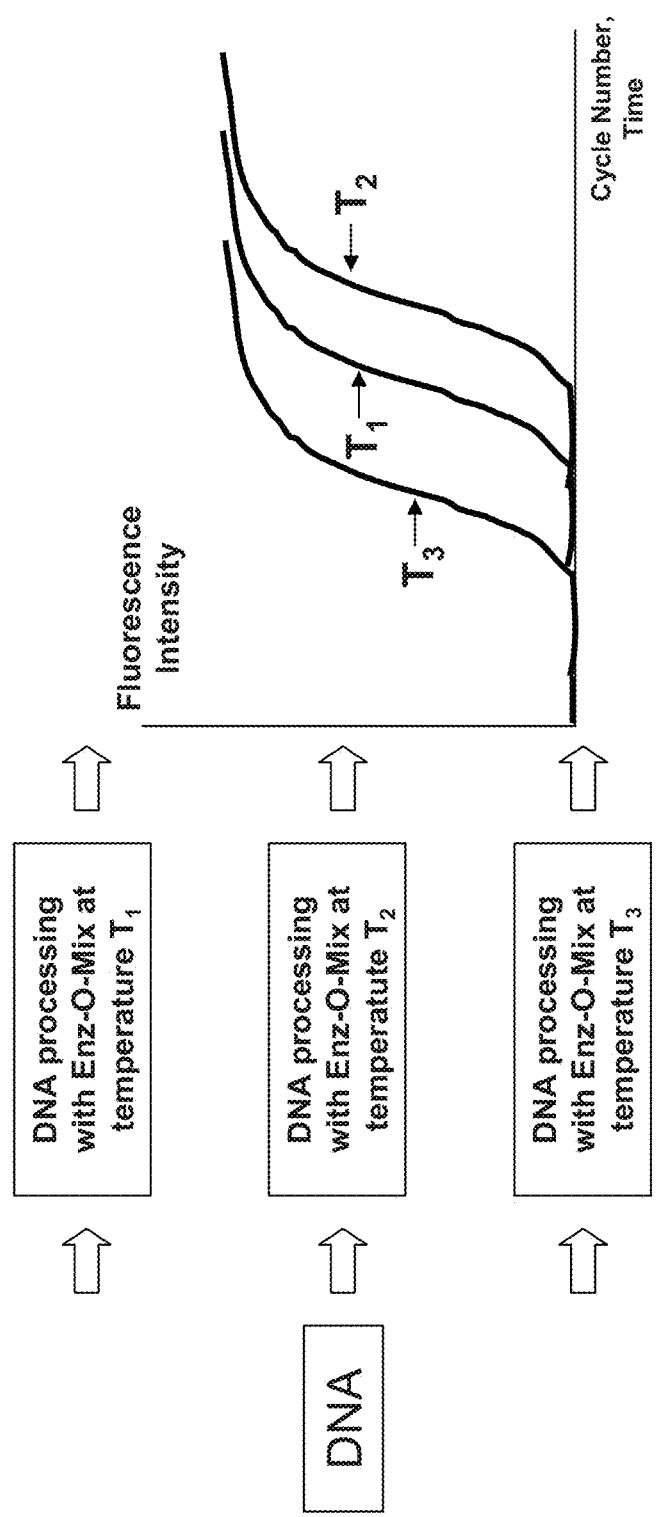
FIG. 21B demonstrates the optimization process for Enz-O-Mix incubation temperature using real-time PCR to monitor amplification of the generated library.

FIG. 21B illustrates the procedure for concentration optimization of the Enz-O-Mix incubation temperature. Three temperatures are employed; specifically, $T_1$, $T_2$ and $T_3$. Temperature $T_3$ results in the early WGA amplification curve, suggesting that the multi-enzymatic reaction was more efficient at this temperature and that the parameter $T_3$ should be selected as a more suitable condition for the Enz-O-Mix reaction.

Figure 21C:
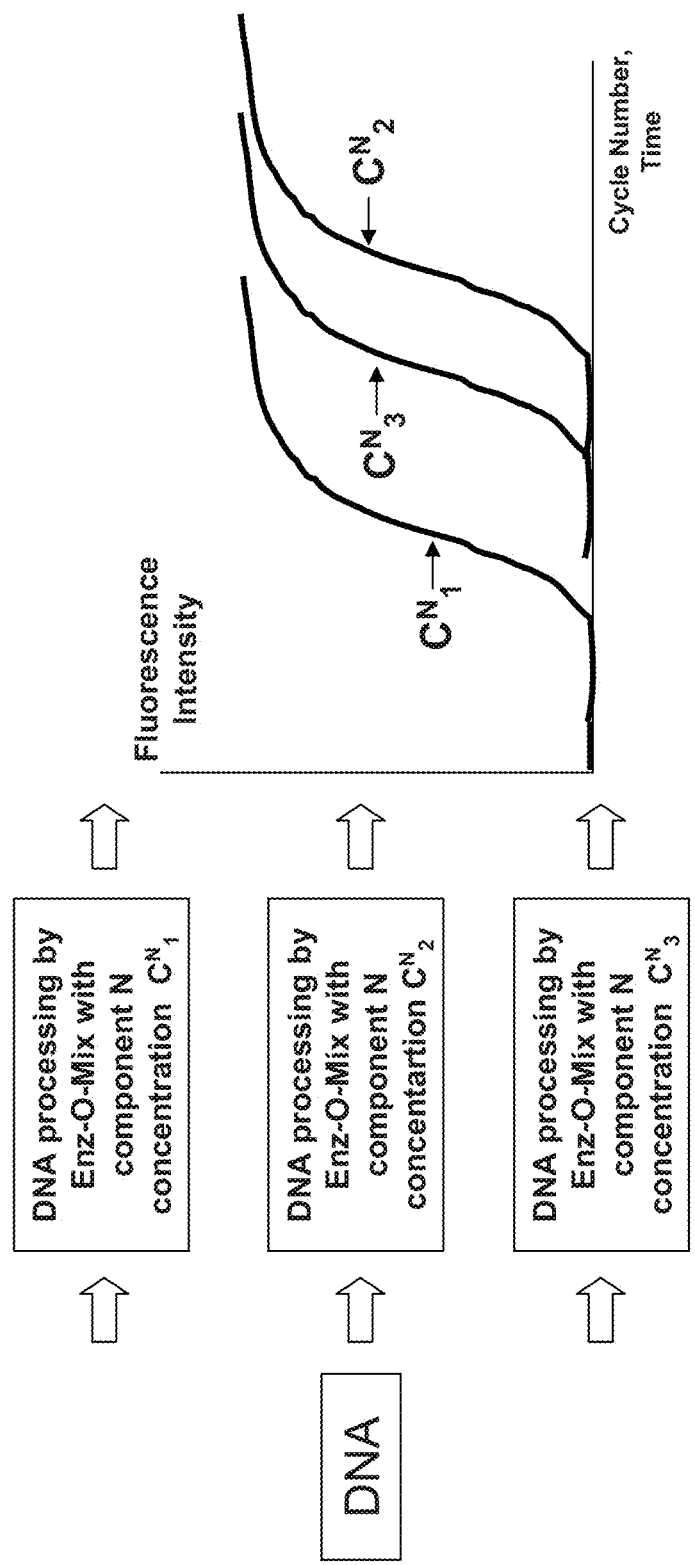
FIG. 21C demonstrates the optimization process for Enz-O-Mix reagent (N) concentration using real-time PCR to monitor amplification of the generated library.

FIG. 21C illustrates the procedure for optimization of the Enz-O-Mix component N. Three concentrations of the component N; specifically, $C^N_1$, $C^N_2$ and $C^N_3$, were utilized. Concentration $C^N_1$ results in the early WGA amplification curve, suggesting that the multi-enzymatic reaction was more efficient at this component N concentration, and that the parameter $C^N_1$ is a particularly suitable condition for the Enz-O-Mix reaction.

V. High Potential for the Enz-O-Mix Approach in Future Biotechnology and Diagnostic Medicine The applications of the Enz-O-Mix method are numerous. The Enz-O-Mix method is easy to automate and use in clinical diagnostic and point-of-care applications. Different enzyme combinations could lead to many novel kits and assays, and applications in such areas as biotechnology, the pharmaceutical industry, molecular diagnostics, forensics, pathology, bio-defense, and bio-computing are contemplated The Enz-O-Mix approach can be viewed as a simple and cost-effective alternative to the "lab-on-a chip" microfluidic approach that is currently attempting to solve the same problem (multi-step DNA processing) by reduction of reaction volumes and integration of multiple reactions into a small format.

Exemplary applications for the invention include but are not limited to the following:

a) A one-step, closed tube preparation and amplification of genomic libraries (WGA) from highly degraded serum, plasma, and/or urine (such as the supernatant fraction) DNA. DNA amplification and re-amplification can be used as an in vitro "immortalization" process to maintain and generate necessary quantities of valuable but limited DNA samples for gene association studies, mutation and microsatellite instability detection in cancer diagnostics, etc.

b) A one-step, closed tube preparation and amplification of genomic libraries (WGA) from formalin fixed, paraffin embedded tissues for cancer diagnostics and research applications.

c) A one-step, closed tube preparation and amplification of Methylome libraries;

d) A one-step preparation and simultaneous immobilization of prepared DNA libraries on a solid support.

EXAMPLES

The following examples are included to demonstrate preferred embodiments of the invention. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments that are disclosed and still obtain a like or similar result without departing from the spirit and scope of the invention.

Example 1

One Step Whole Genome Library Amplification Using Hairpin Adaptor with EcoNI Resrtiction Site Generated after Ligation and Strand-Displacement Extension In this example, a single step WGA process is described wherein a partial hairpin oligonucleotide adaptor containing EcoNI recognition half sites in its stem is extended by a DNA polymerase to form a blunt end hairpin molecule and is ligated via its free 3' end to the 5' phosphate of blunt-ended DNA restriction fragments by T4 DNA ligase. Due to the strand-displacement activity of the DNA polymerase, the free 3' end of the restriction fragments are extended using as template the ligated 3' end of the adaptor, thus opening up the hairpin structure and generating functional EcoNI cleavage site (FIGS. 12 and 13A). Following cleavage with EcoNI present in the same reaction mix, the DNA library molecules have their terminal inverted repeats excised and become amplifiable by PCR using a primer complementary to the 5' stem portion of the adaptor sequence. The whole process takes place in a single tube and in one step in just about 1 hour, in specific embodiments.

Human genomic DNA isolated from the peripheral blood of a healthy donor by standard procedures was digested with 10 units of AluI restriction enzyme (NEB) for 1 hour following the manufacturer's protocol.

For library preparation, 5 nanograms of AluI-digested DNA were incubated in a reaction mixture comprising 1× NEBuffer 4 (20 mM Tris-acetate, 10 mM Mg acetate, 50 mM potassium acetate, 1 mM dithiothreitol, pH 7.9), 1 µM EcoNI Ext Adaptor oligonucleotide (Table I, SEQ ID NO:1), 1 mM ATP, 120 µM dNTPs, 2 Units of Klenow fragment of DNA polymerase I, 400 units of T4 DNA ligase (New England Biolabs, NEB; Beverly, Mass.), and 10 units of EcoNI restriction enzyme (NEB) in a final volume of 15 µl for 1 hour at 37° C. Enzymes were inactivated for 10 min at 75° C. Control reaction that contained no EcoNI restriction enzyme was also run in parallel.

Figure 22:
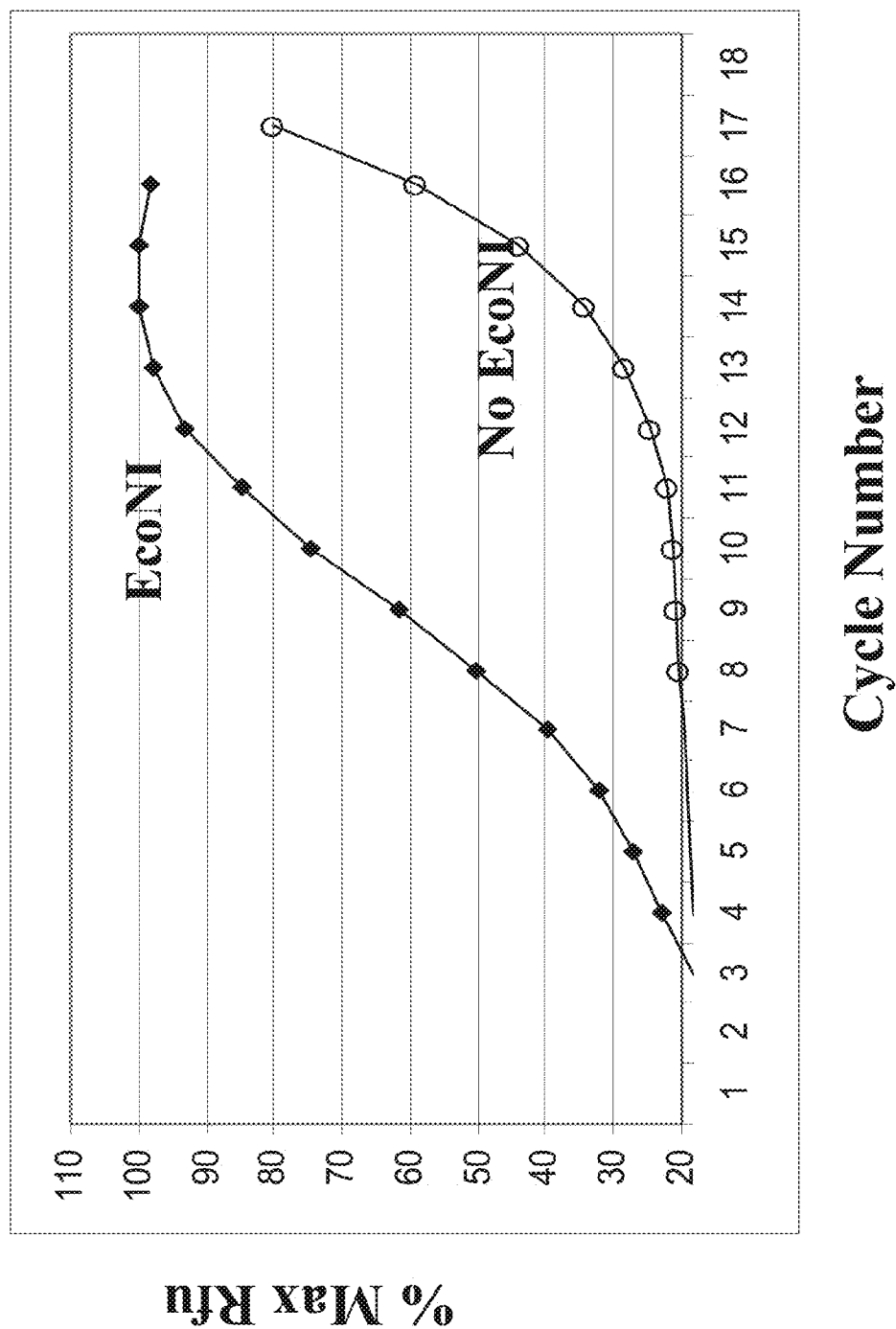
FIG. 22 shows real-time amplification curves of whole genome libraries prepared in a single step by ligation of a stem-loop oligonucleotide with EcoNI resrtiction site generated after ligation and strand-displacement extension of blunt-end AluI restriction fragments in the presence or in the absence of EcoNI. Excision of the terminal inverted repeat by EcoNI results in high amplification efficiency that exceeds amplification efficiency of the library with inverted repeats (in the absence of the Eco NI cleavage) by two orders of magnitude.

The resulting library was amplified by real-time PCR in a reaction mixture containing: 1× Titanium Taq reaction buffer (Clontech; Mountain View, Calif.); 200 µM each dNTP; 1:10,000 dilutions of fluorescein and SybrGreen I (Molecular Probes; Carlsbad, Calif.); 1 µM of $K_U$ primer (Table I, SEQ ID NO:2); and 5 units of Titanium Taq polymerase (Clontech; Mountain View, Calif.) in a reaction volume of 75 µl. PCR amplification was carried out for 15 cycles at 95° C. for 15 sec and 65° C. for 2 min on i-Cycler real-time PCR instrument (Bio-Rad; Hercules, Calif.). FIG. 22 shows the amplification curves of the libraries prepared in the presence or in the absence of EcoNI. Cleavage of the terminal inverted repeat by EcoNI improved the efficiency of amplification by 7 cycles, i.e. over two orders of magnitude.

Figure 24A:
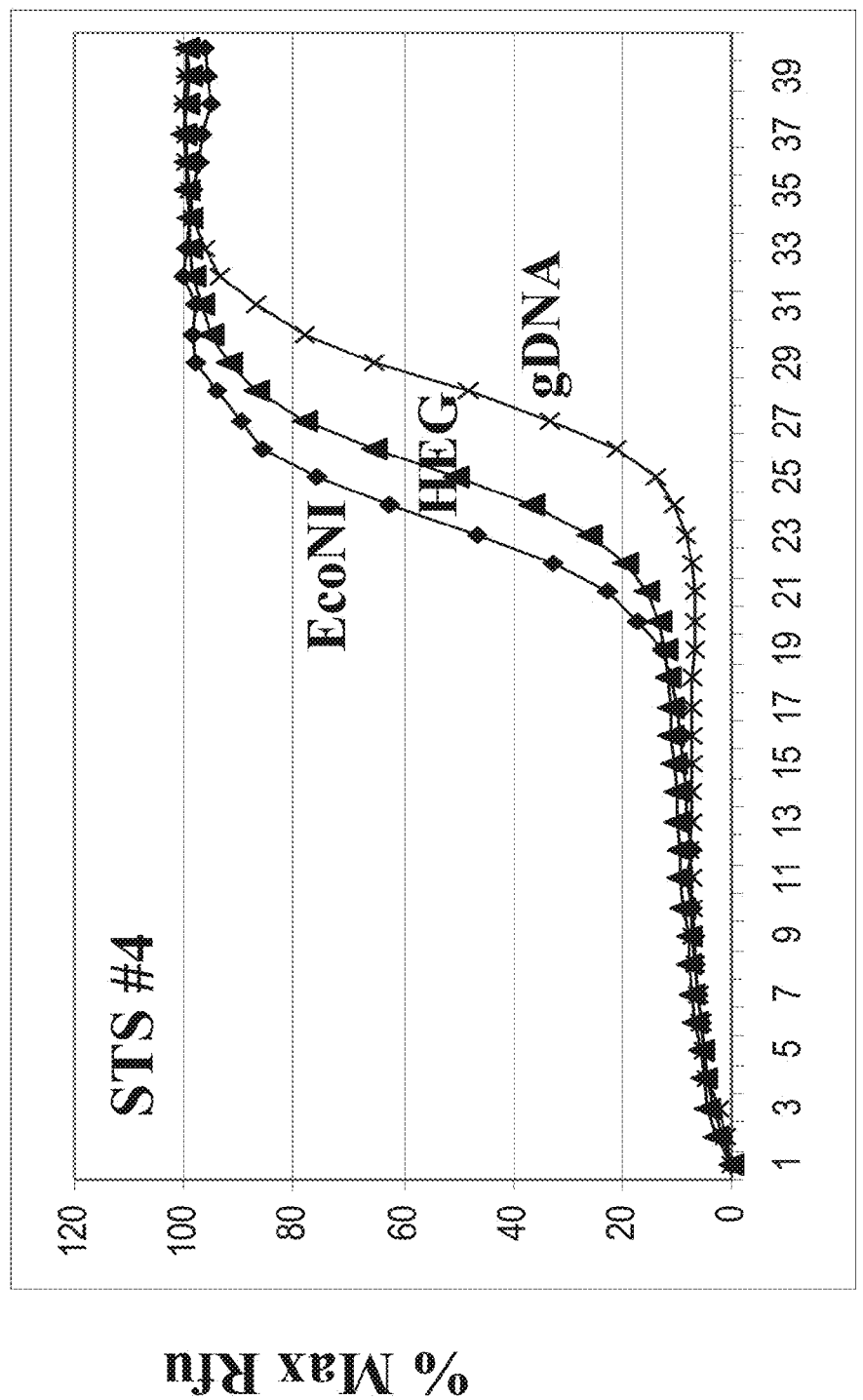
FIGS. 24A, 24B, and 24C show the real-time PCR amplification curves of 3 exemplary human STS markers used for evaluation of genomic sequence representation in WGA libraries prepared in a single step by ligation of blunt-end AluI restriction fragments to a stem-loop oligonucleotide containing within a loop either the hexa-ethylene glycol linker (HEG) as a replication stop, or the EcoNI recognition sequence that becomes functional (cleavable) after ligation and strand-displacement extension. Twenty nanograms of purified material of each library is compared to 1 ng of human genomic DNA randomly fragmented to an average size of 1.5 Kb using Hydro Shear device (gDNA).
Figure 24B:
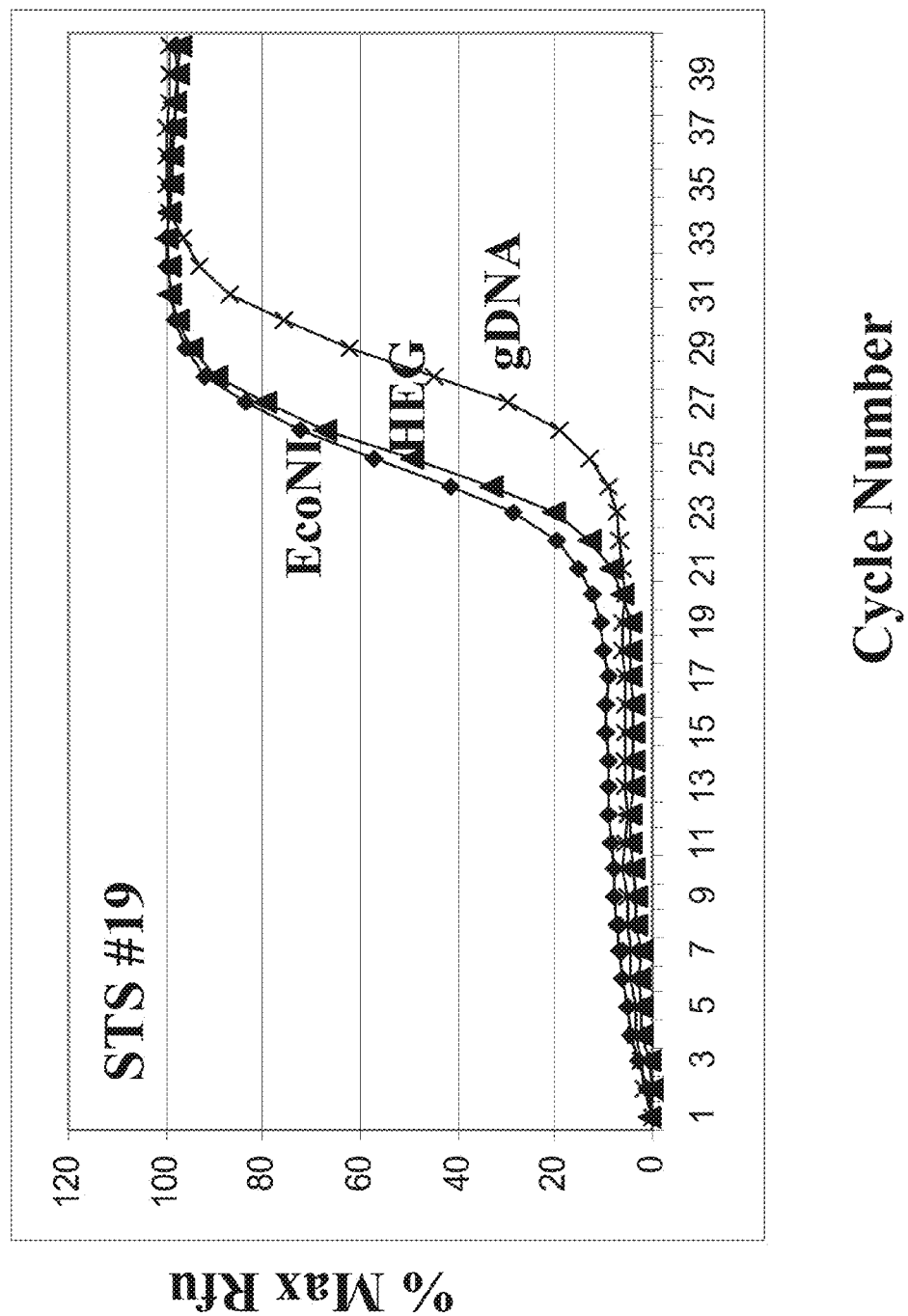
Figure 24C:
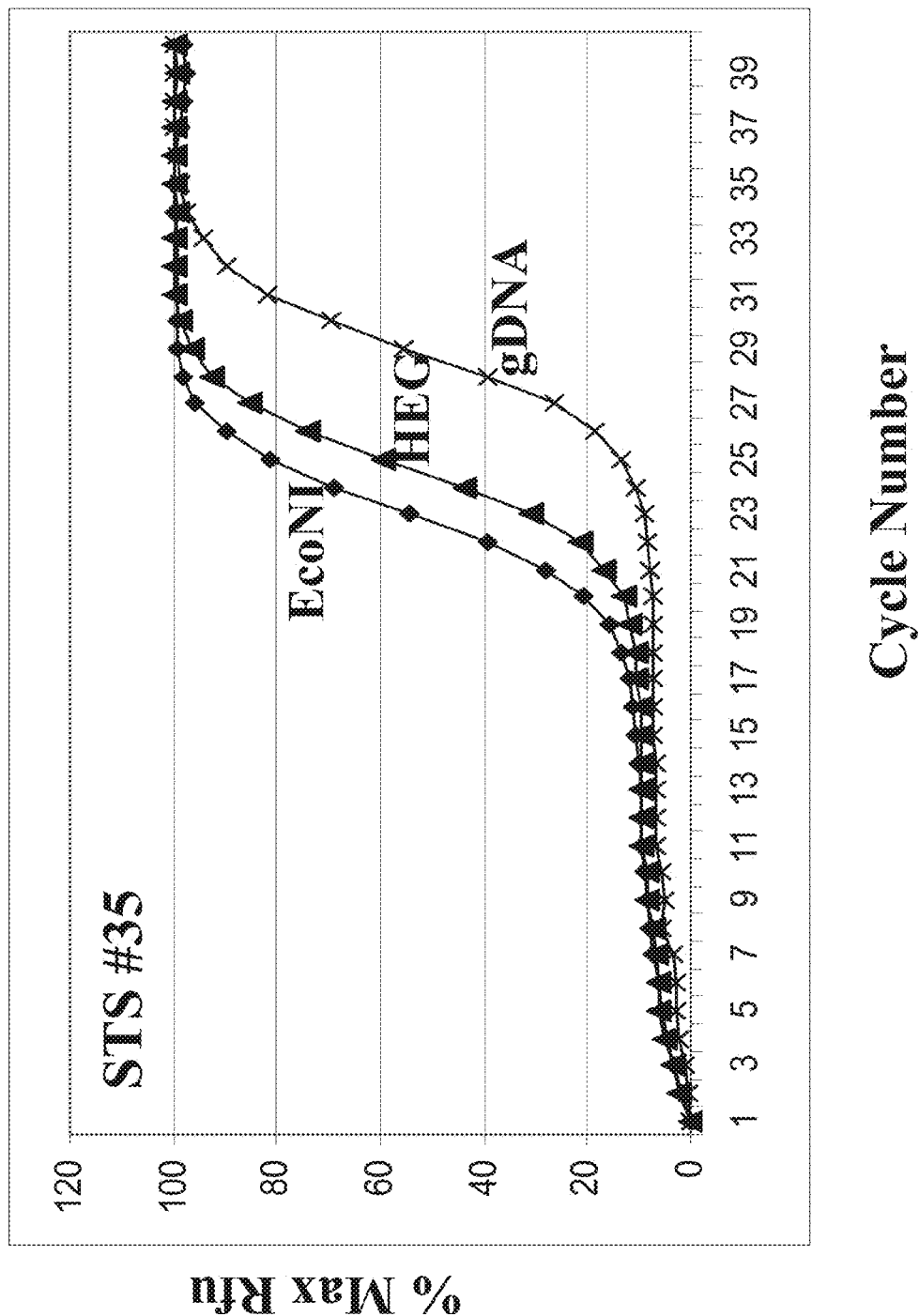

Preliminary representation analysis of the library prepared in the presence of EcoNI was conducted using three exemplary human genomic STS markers (Table II). The material amplified by PCR with the universal $K_U$ primer was purified with Qiaquick filters (Qiagen; Valencia, Calif.), and 20 ng aliquots were analyzed in real-time PCR. Reactions were carried out for 45 cycles at 94° C. for 15 sec and 68° C. for 1 min on i-Cycler (Bio-Rad; Hercules, Calif.). The PCR reaction mixture comprised the following: 1× Titanium Taq reaction buffer (Clontech; Mountain View, Calif.); 200 µM each dNTP; 1:10,000 dilutions of fluorescein and SybrGreen I (Molecular Probes); 0.2 µM each forward and reverse STS primer (Table II); 5 units of Titanium Taq polymerase (Clontech; Mountain View, Calif.); and 20 ng library DNA. A control reaction comprising 1 ng of human genomic DNA randomly fragmented to an average size of 1.5 Kb using Hydro Shear device (Gene Machines; Palo Alto, Calif.) was performed. FIGS. 24A-24C show unbiased representation of the analyzed human STS sequences in the EcoNI-treated library.

Example 2

One Step Whole Genome Amplification Using Hairpin Adaptor with Non-Replicable 18-Atom Hexa-Ethyleneglycol Spacer In this example, a single step WGA process is described wherein a hairpin oligonucleotide adaptor containing non-replicable 18-atom hexa-ethyleneglycol (HEG) spacer in its loop is ligated via its free 3' end to the 5' phosphate of DNA restriction fragments in the presence of T4 DNA ligase and a DNA polymerase. Due to the strand-displacement activity of the polymerase, the free 3' ends of the restriction fragments are extended until the replication stop is reached (see FIGS. 8 and 10A). This process results in truncated 3' termini of the resulting WGA library such that they do not contain a terminal inverted repeat. The library molecules are then amplified by PCR using a primer complementary to the universal sequence of the extended 3' termini. The whole process takes place in a single tube in one step and is completed in just about 1 hour, in specific embodiments.

In control experiments, hairpin adaptor molecules that either do not comprise a replication stop or modified bases or that comprise ribo-nucleosides in their loop region are compared for their ability to participate in WGA along with the hexa-ethyleneglycol adaptor described above.

Human genomic DNA isolated from the peripheral blood of a healthy donor by standard procedures was digested with 10 units of AluI restriction enzyme (NEB) for 1 hour following the manufacturer's protocol.

Five nanograms of AluI digested DNA were incubated in a reaction mixture comprising 1× NEBuffer 4; 1 µM HEG Adaptor oligonucleotide (Table I, SEQ ID NO:3) or control hairpin adaptors (see below); 1 mM ATP; 120 µM dNTPs; 2 Units of Klenow fragment of DNA polymerase I; and 400 units of T4 DNA ligase (NEB) in a final volume of 15 µl for 1 hour at 37° C. Enzymes were inactivated for 10 min at 75° C.

To test the effect of the hexa-ethyleneglycol replication stop, control reactions containing partial hairpin oligonucleotides extended by Klenow to form blunt end hairpin adaptors that either do not contain replication stop (Table I, Hairpin Adaptor, SEQ ID NO:5), or containing ribonucleosides in their loop region (Table I, Hairpin Ribo Adaptor, SEQ ID NO:6) were substituted for the HEG Adaptor (Table I, SEQ ID NO:3) and run in parallel as described above.

Figure 23:
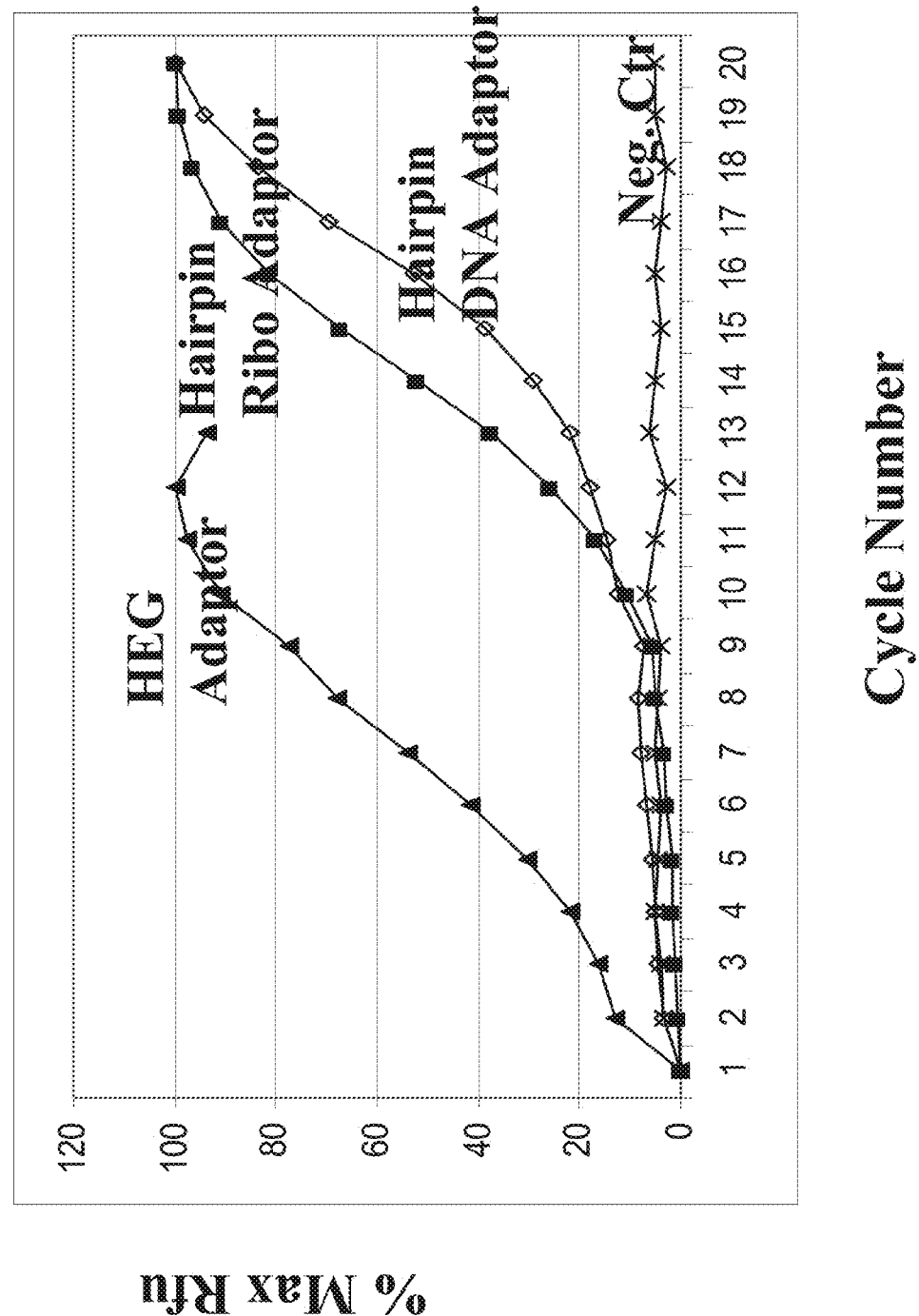
FIG. 23 shows real-time amplification curves of libraries prepared in a single step by ligation of blunt-end AluI restriction fragments to the stem-loop oligonucleotide comprising hexa-ethylene glycol replication stop (HEG Stem-Loop Oligo), a stretch of 5 ribonucleosides (Ribo Stem-Loop Oligo), or just deoxyribonucleosides (Stem-Loop Oligo) in their loop regions. Unlike the libraries made with HEG-containing oligonucleotide, the libraries with ribonucleosides in the loop region are not amplified efficiently, suggesting that ribonucleosides in the template strand do not arrest DNA replication carried by the Klenow fragment of DNA polymerase I.

The resulting libraries were amplified by real-time PCR in a reaction mixture comprising the following: 1× Titanium Taq reaction buffer (Clontech; Mountain View, Calif.); 200 µM each dNTP; 1:10,000 dilutions of fluorescein and SybrGreen I (Molecular Probes; Carlsbad, Calif.); 1 µM of universal primer ($Y_U$ primer, Table I SEQ ID NO:4 in the case of the HEG adaptor, or $K_U$ primer, Table I, SEQ ID NO:2, in the case of control hairpin adaptors); and 5 units of Titanium Taq polymerase (Clontech; Mountain View, Calif.) in a reaction volume of 75 µl. PCR amplification was carried out at 95° C. for 15 sec and 65° C. for 2 min on i-Cycler real-time PCR instrument (Bio-Rad; Hercules, Calif.). As shown on FIG. 23, amplification of the library prepared by ligation of hexa-ethyleneglycol adaptor was 9 cycles more efficient than a library made with adaptor not containing a replication stop in its loop structure. The results shown on FIG. 23 also indicate that an array of 5 consecutive ribonucleosides in the adaptor's loop is not a preferable replication stop for Klenow fragment of DNA polymerase I, since amplification of a library prepared by ligation of such an adaptor amplified only 2 cycles earlier than a library made with adaptor containing only deoxyribonucleosides.

Preliminary representation analysis of the library prepared by ligation of HEG adaptor was done using three exemplary human genomic STS markers (Table II). The material amplified by PCR with the universal $Y_U$ primer was purified with Qiaquick filters (Qiagen; Valencia, Calif.), and 20 ng aliquots were analyzed in real-time PCR as described in Example 1. FIGS. 24A-24C show unbiased representation of the analyzed human STS sequences in this exemplary library.

Example 3

One Step Whole Genome Library Preparation Using Degradable Hairpin Adaptor Comprising Deoxy-Uridine In this example, a single step WGA process is described wherein a hairpin oligonucleotide adaptor comprising deoxy-uridine in both its 5' stem region and in its loop (FIG. 10B) is ligated via its free 3' end to the 5' phosphates of DNA restriction fragments in the presence of 3 enzymatic activities: T4 DNA ligase, DNA polymerase, and Uracil-DNA glycosylase (which is also referred to as UDG or dU glycosylase). UDG catalyzes the release of free uracil and generates abasic sites in the adaptor's loop region and the 5' half of the hairpin. The strand-displacement activity of the DNA polymerase extends the free 3' end of the restriction fragments until an abasic site is reached, serving as a replication stop (FIG. 10B). This process results in truncated 3' ends of the resulting WGA library fragments such that they do not have terminal inverted repeats. Prior to amplification, samples are heated in order to break the phosphodiester bonds of the generated abasic sites, and the adaptor molecules are degraded into 2 small fragments and one intact 18 base oligonucleotide complementary to the universal sequence of the extended 3' termini (FIG. 10B). The released 18 base oligonucleotide then serves as a primer in subsequent PCR amplification, or alternatively it can be exogenously supplied. The entire process takes place in a single tube in one step and is completed in just 1 hour.

Human genomic DNA isolated from the peripheral blood of a healthy donor by standard procedures was digested with 10 units of AluI restriction enzyme (New England Biolabs; Beverly, Mass.) for 1 hour following the manufacturer's protocol.

For library preparation, five nanograms of AluI-digested genomic DNA were incubated in an exemplary reaction mixture comprising 1× NEBuffer 4; 2 µM dU Hairpin Adaptor oligonucleotide (Table I, SEQ ID NO:7); 1 mM ATP; 120 µM dNTPs; 2 Units of Klenow fragment of DNA polymerase I; 400 units of T4 DNA ligase; and 2 Units of UDG (New England Biolabs; Beverly, Mass.) in a final volume of 15 µl for 1 hour at 37° C. Enzymes were inactivated at 75° C. for 10 min. A control reaction containing no UDG was run in parallel.

Figure 25:
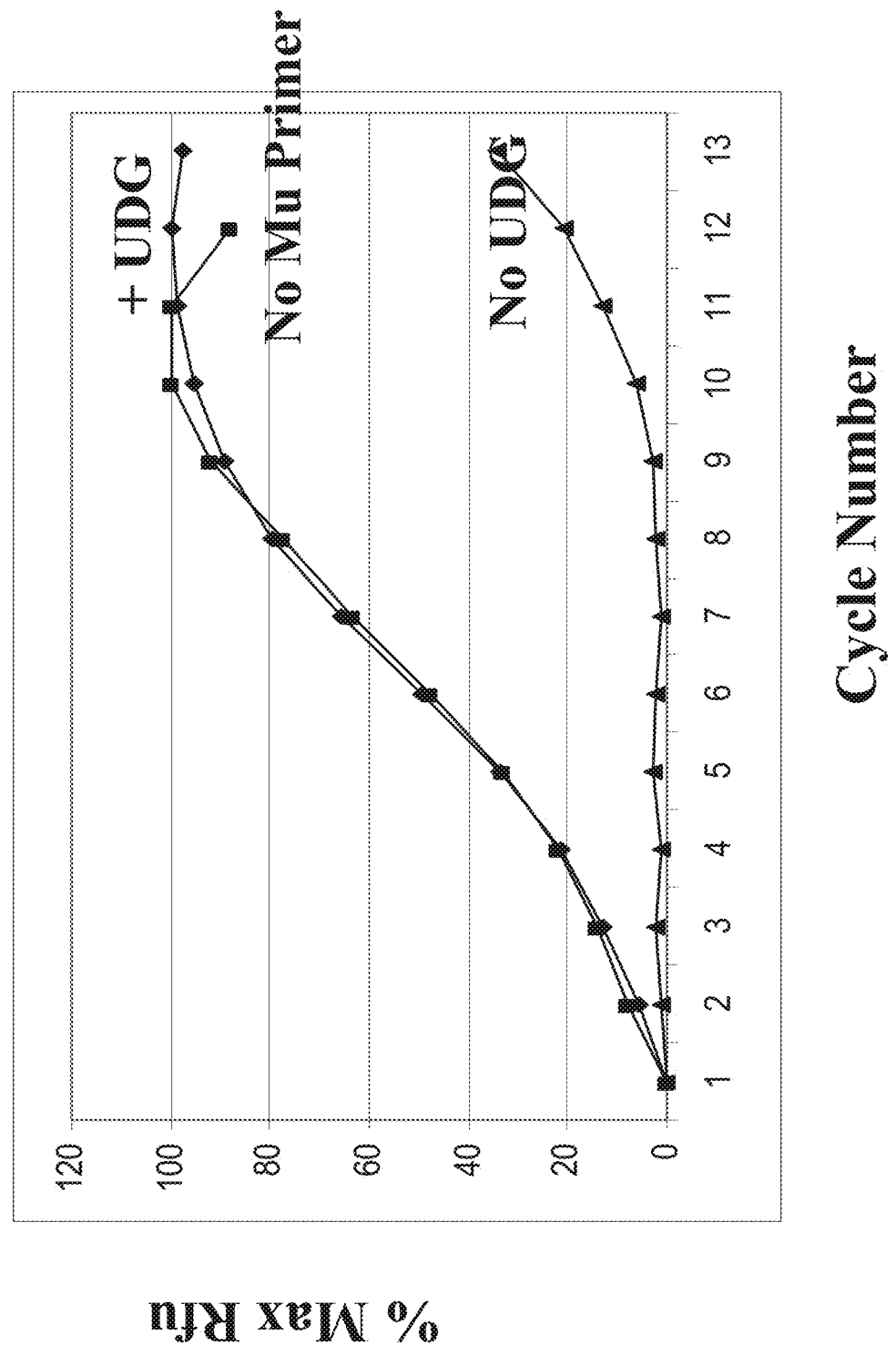
FIG. 25 shows the real-time amplification curves of libraries prepared in a single step by ligation of blunt-end AluI restriction fragments to the stem-loop oligonucleotide containing deoxy-uridine in the 5' stem region and in the loop with T4 DNA ligase and Klenow fragment of DNA polymerase I, in the presence or in the absence Uracil-DNA glycosylase (which is also referred to as UDG or dU glycosylase). Amplification is conducted by either adding universal primer $M_U$ or using the primer released as a result of the UDG activity, followed by heat-induced degradation of the stem-loop oligonucleotide.

The resulting library was amplified by real-time PCR in a reaction mixture comprising the following: 1× Titanium Taq reaction buffer (Clontech, Mountain View, Calif.); 200 µM each dNTP; 1:10,000 dilutions of fluorescein and SybrGreen I (Molecular Probes; Carlsbad, Calif.); 1 µM of universal $M_U$ primer (Table I, SEQ ID NO:8); and 5 units of Titanium Taq polymerase (Clontech; in a reaction volume of 75 µl). PCR amplifications were carried out at 95° C. for 15 sec and 65° C. for 2 min on i-Cycler real-time PCR instrument (Bio-Rad; Hercules, Calif.). In a separate amplification reaction, no external universal $M_U$ primer was supplied to test if endogenously-generated primer is sufficient for library amplification. FIG. 25 shows that virtually identical amplification curves were generated whether or not the universal primer was added exogenously or was generated as a result of the UDG activity followed by heat-induced degradation of the adaptor. FIG. 25 also shows that if UDG was not present during library preparation, this caused an 8 cycle-delay in amplification. This latter result once again indicates the preference of removal of the terminal inverted repeat of a hairpin adaptor for efficient library priming and amplification.

Example 4

One Step Genomic DNA Restriction Digestion and Whole Genome Library Preparation Using Degradable Hairpin Adaptor Comprising Deoxy-Uridine In this example, a single step WGA process is described wherein a hairpin oligonucleotide adaptor comprising deoxy-uridine described in Example 3 is ligated via its free 3' end to the 5' phosphates of DNA restriction fragments generated from intact genomic DNA in a single exemplary reaction mix comprising 4 exemplary enzymatic activities: AluI restriction endonuclease, T4 DNA ligase, DNA polymerase, and Uracil-DNA glycosylase (UDG) (FIG. 19A, Enz-O-Mix 3). UDG catalyses the release of free uracil and generates abasic sites in the adaptor's loop region and the 5' half of the hairpin. AluI digests the target DNA into restriction fragments. T4 DNA ligase generates a phosphodiester bond between the 3' ends of the adaptor molecules and the 5' phosphates of the restriction fragments. Finally, the strand-displacement activity of the DNA polymerase extends the free 3' end of the restriction fragments using as template the ligated 3' end of the hairpin stem until an abasic site is reached that serves as a replication stop (FIG. 10B). Prior to amplification, samples are heated to degrade the abasic sites of the adaptor, and the resulting library is amplified using the universal primer $M_U$. The entire process takes place in a single tube in one step and is completed in just 1 hour.

For library preparation, 20, 10, 3, 1, 0.3, 0.1, 0.03, 0.01, or 0 nanograms of human genomic DNA isolated from the peripheral blood of a healthy donor by standard procedures were incubated in an exemplary reaction mix comprising: 1× NEBuffer 4; 2 µM dU Hairpin Adaptor oligonucleotide (Table I, SEQ ID NO:7); 1 mM ATP; 120 µM dNTPs; 2 Units of Klenow fragment of DNA polymerase I; 400 units of T4 DNA ligase; 2 Units of UDG; and 10 units of AluI restriction endonuclease (New England Biolabs; Beverly, Mass.) in a final volume of 15 μl for 1 hour at 37° C. Enzymes were inactivated for 10 min at 75° C.

Figure 26:
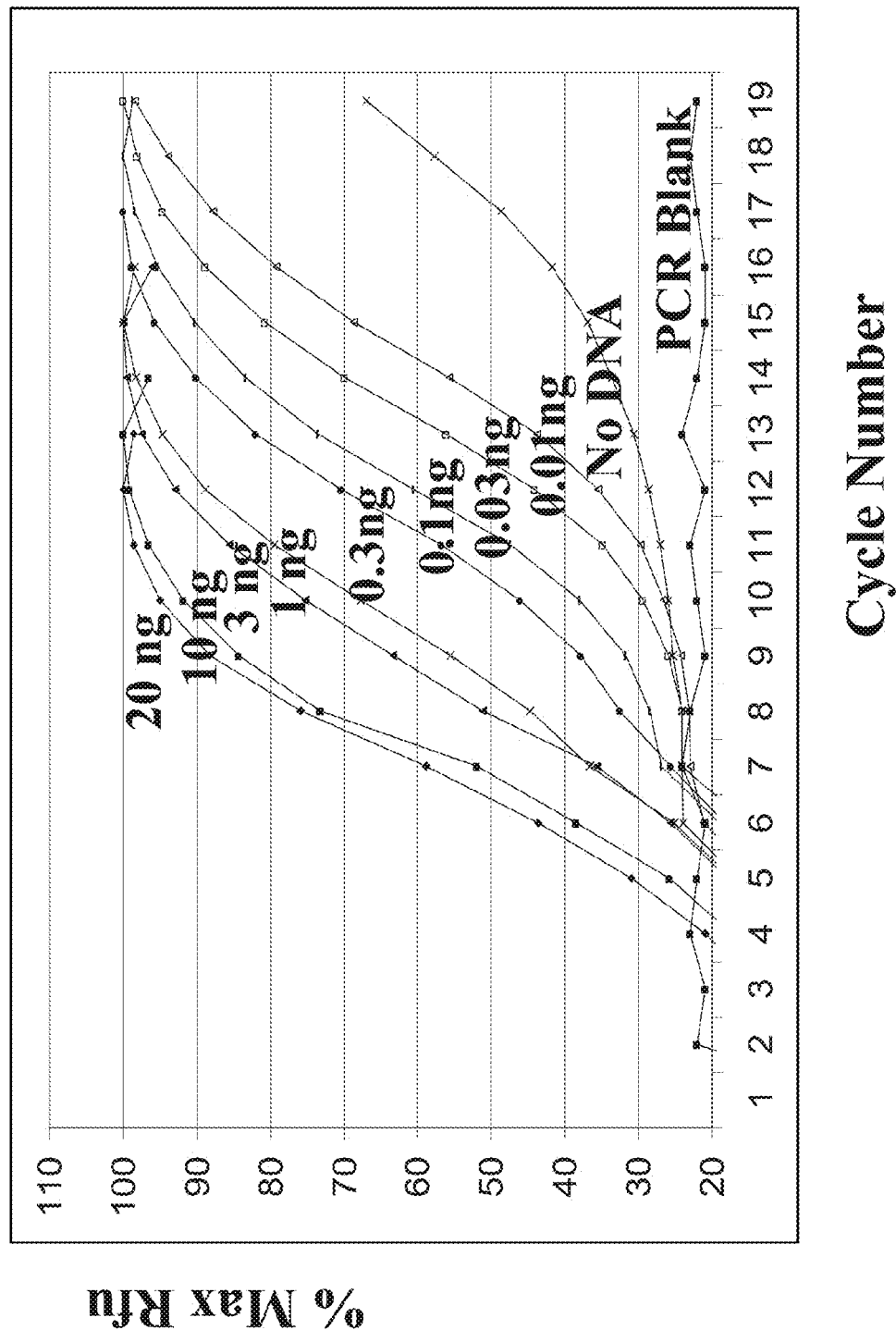
FIG. 26 illustrates a one-step genomic DNA restriction digestion and whole genome amplification using degradable stem-loop oligonucleotide containing deoxy-uridine in the 5' stem region and in the loop. Human genomic DNA in amounts ranging from 20 ng to 10 pg or a blank sample (no DNA control) are incubated with the stem-loop oligonucleotide in the presence of 4 exemplary enzymatic activities: AluI restriction endonuclease, T4 DNA ligase, Klenow fragment of DNA polymerase I, and Uracil-DNA glycosylase (UDG) for 1 hour at 37° C. and amplified by PCR using universal primer $M_U$.

The resulting libraries were amplified by real-time PCR in the exemplary reaction mixture comprising the following: 1× Titanium Taq reaction buffer (Clontech; Mountain View, Calif.); 200 μM each dNTP; 1:10,000 dilutions of fluorescein and SybrGreen I (Molecular Probes; Carlsbad, Calif.); 1 μM of universal $M_U$ primer (Table I, SEQ ID NO:8); and 5 units of Titanium Taq polymerase (Clontech; Mountain View, Calif.) in a reaction volume of 75 μl. PCR amplifications were carried out at 95° C. for 15 sec and 65° C. for 2 min on i-Cycler real-time PCR instrument (Bio-Rad; Hercules, Calif.). FIG. 26 shows the amplification curves of the resulting libraries. As shown, a series of titration curves was generated in a concentration-dependent manner. The smallest amount of DNA corresponding to less than two genome equivalents was still discernible from the control reaction with no DNA, indicating that the described single closed tube process is an efficient and sensitive way of whole genome amplification.

Example 5

Simplified Protocol Combining Preparation of Methylome Libraries from Cell-Free Urine DNA and Cleavage with Methylation-Sensitive Restriction Enzymes in One Step In this example, the preparation of methylome libraries from cell-free urine DNA by ligation of hairpin oligonucleotide adaptor comprising deoxy-uridine as described in Example 3 is combined with the simultaneous cleavage with a mix of methylation-sensitive restriction enzymes in a single step.

Cell-free DNA was isolated from urine of healthy donors collected in 50 ml Falcon tubes and stabilized for storage by adding 0.1 volume of 0.5 M EDTA. Urine samples were centrifuged at 1,800×g for 10 min at ambient temperature to sediment cells, and supernatant was transferred carefully to a fresh tube. Equal volume of 6 M solution of guanidine thiocyanate was added to each sample followed by ⅙ vol of Wizard Miniprep resin (Promega catalog # A7141; Madison, Wis.). DNA was bound to the resin by rotation for 1 hour at ambient temperature. The resin was then sedimented by brief centrifugation at 500×g and loaded on Wizard minicolumns (Promega catalog #A7211; Madison, Wis.) using syringe barrel extensions after carefully decanting out the supernatant. Resin was washed with 5 ml of wash buffer (Promega catalog # A8102; Madison, Wis.) using Qiagen QIAvac-24 vacuum manifold. Minicolumns were then centrifuged for 2 min at 10,000×g to remove residual wash buffer and bound DNA was eluted with 50 μl of DNAse-free water at 10,000×g for 1 min. Eluted DNA was buffered by adding 0.1 vol of 10× TE-L buffer and quantified on a fluorescent spectrophotometer using Pico Green (Molecular Probes; Carlsbad, Calif.) and 1 phage D.

Aliquots of 200 ng of cell-free DNA were artificially methylated by incubation in 20 μl of NEBuffer 2 (New England Biolabs; Beverly, Mass.) with 4 units of M.SssI CpG methylase (New England Biolabs; Beverly, Mass.) in the presence of 160 μM SAM for 1 hour at 37° C.

Twenty five nanograms of methylated or non-methylated DNA were incubated in 1× NEBuffer 4 (New England Biolabs; Beverly, Mass.) comprising 0.35 units of T4 DNA polymerase (New England Biolabs; Beverly, Mass.); 1.5 μM of dU-Hairpin Adaptor (Table I, SEQ ID NO:7); 0.5 units of UDG (New England Biolabs; Beverly, Mass.); 400 units of T4 DNA ligase (New England Biolabs; Beverly, Mass.); 30 μM dNTPs, 0.75 mM ATP; 75 μg/ml BSA; 16.7 units of AciI; 16.7 units of HhaI; 8.3 units each of BstUI, HpaII, and HinpII (New England Biolabs; Beverly, Mass.) in a final volume of 20 μl for 1 hour at 37° C. A second aliquot of 25 ng of methylated or non-methylated DNA was incubated in parallel with all the ingredients described above but without the restriction enzymes ("uncut" control).

One half of each sample (12.5 ng) was then amplified by quantitative PCR in an exemplary reaction mix comprising 1× Titanium Taq reaction buffer (Clontech; Mountain View, Calif.); 200 μM of each dNTP; fluorescein calibration dye (1:100,000) and SYBR Green I (1:100,000); 1 μM universal primer $M_U$-1 (Table I, SEQ ID NO:8); 4% DMSO; 200 μM 7-deaza-dGTP (Sigma); and 5 units of Titanium Taq polymerase (Clontech) in a final volume of 75 μl. Samples were pre-heated at 72° C. for 15 min followed by 95° C. for 5 min and 12 cycles at 94° C. for 15 sec and 65° C. for 2 min on an I-Cycler real-time PCR instrument (Bio-Rad; Hercules, Calif.). Amplified libraries were purified using MultiScreen PCR cleanup system (Millipore) and quantified by optical density reading.

Methylation analysis of promoter sites was performed by real-time PCR using aliquots of 160 ng of each digested or non-digested amplified library DNA incubated in exemplary reaction mixtures comprising the following: 1× Titanium Taq reaction buffer (Clontech; Mountain View, Calif.); 200 μM of each dNTP; 4% DMSO; 0.5 M betaine; FCD (1:100,000) and SYBR Green I (1:100,000); 200 nM each forward and reverse primer (Table II, SEQ ID NO:11 and SEQ ID NO:12 for GSTP-1 promoter, SEQ ID NO:13 and SEQ ID NO:14 for MDR-1 promoter, SEQ ID NO:9 and SEQ ID NO:10 for EDNRB promoter, and SEQ ID NO:15 and SEQ ID NO:16 for PTGS-2 promoter); and approximately 1.5 units of Titanium Taq polymerase (Clontech; Mountain View, Calif.) in a final volume of 15 μl at 95° C. for 3 min followed by 50 cycles at 94° C. for 15 sec and 68° C. for 1 min.

Figure 27:
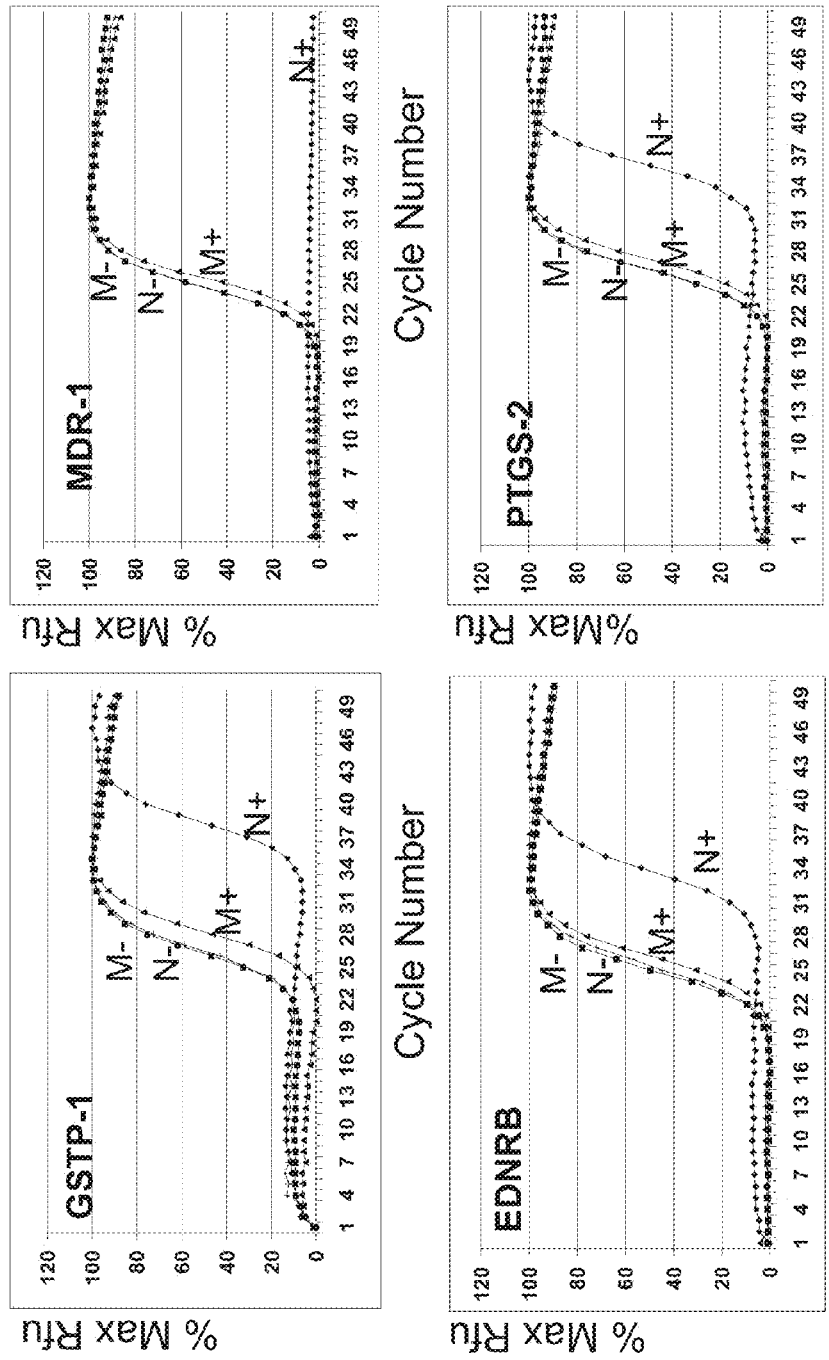
FIG. 27 shows PCR amplification curves of specific promoter sites from amplified libraries prepared from non-methylated (N) and artificially methylated (M) cell-free urine DNA from a healthy donor. Libraries were prepared by ligation of a degradable stem-loop oligonucleotide containing deoxy-uridine with (N+, M+) or without (N−, M−) simultaneous cleavage with methylation-sensitive restriction enzymes. Promoter sites from non-methylated cleaved DNA (N+) amplify with significant (at least 10 cycles) delay as compared to uncut DNA (N−, M−) unlike methylated DNA which is refractory to cleavage (M+ versus M−).

FIG. 27 shows PCR amplification curves of specific promoter sites in amplified libraries prepared from methylated (M) or non-methylated (N) urine DNA in the presence (+) or in the absence (−) of methylation-sensitive restriction enzymes. As expected, promoter sites from non-methylated cleaved DNA (N+) amplified with significant (at least 10 cycles) delay as compared to uncut DNA (N−, M−) for all four promoter sites tested. On the other hand, methylated DNA was completely refractory to cleavage (M+). These results demonstrate that the method disclosed in the present invention can be applied as a simple one-step non-invasive high-throughput diagnostic procedure for detection of aberrant methylation in cancer.

TABLE I

| | OLIGONUCLEOTIDE SEQUENCES | |
|---|---|---|
| No | Code | Sequence 5'-3' |
| 1. | EcoNI Ext Adaptor | CCAAACACACCCAACACACCTAAAAAAGGTGT (SEQ ID NO: 1)* |
| 2. | $K_U$ | TGTGTTGGGTGTGTTTGG (SEQ ID NO: 2) |
| 3. | HEG Adaptor | AAGAGAGAGGGAAGGAAGAA/HEG/AACTTCC TTCCCTCTCTCTT (SEQ ID NO: 3)** |
| 4. | $Y_U$ | CTTCCTTCCCTCTCTCTT (SEQ ID NO: 4) |
| 5. | Hairpin Adaptor | CCAAAC ACACCCAACACAAAAAGTGTTG (SEQ ID NO: 5) |

TABLE I -continued

OLIGONUCLEOTIDE SEQUENCES

| No | Code | Sequence 5'-3' |
|---|---|---|
| 6. | Hairpin Ribo Adaptor | CCAAAC ACACCCAACACrArArArArAGTGT TG(SEQ ID NO: 6)*** |
| 7. | dU Hairpin Adaptor | TGTGTTGGGdUGdUGTGTGGdUdUdUdUdUdUC CACACACACCCAACACA (SEQ ID NO: 7)**** |
| 8. | M$_U$ | CCACACACACCCAACACA (SEQ ID NO: 8) |
| 9. | EDNRB | GGAGGAGTCTTTCGAGTTCAA (SEQ ID NO: 9) Forward CGGGAGGAATACAGACACGTCTT (SEQ ID NO: 10) Reverse |
| 10. | GSTP-1 | GGAAAGAGGGAAAGGCTTC (SEQ ID NO: 11) Forward CCCCAGTGCTGAGTCACGG (SEQ ID NO: 12) Reverse |
| 11. | MDR-1 | GGGTGGGAGGAAGCATCGTC (SEQ ID NO: 13) Forward GGTCTCCAGCATCTCCACGAA (SEQ ID NO: 14) Reverse |
| 12. | PTGS-2 | AGAACTGGCTCTCGGAAGCG (SEQ ID NO: 15) Forward GGGAGCAGAGGGGGTAGTC (SEQ ID NO: 16) Reverse |
| 13. | dUT7 Hairpin Adaptor | TGTGTTGGGdUGdUGTGTGGdUdUdUdUdUdUA TTTAATACGACTCACTATAGGGAGACCACACAC ACCCAACACA (SEQ ID NO: 17)**** |
| 14. | dU_N.BbvC IB_Nick Hairpin Adaptor | TGTGTTGGGdUGdUGTGTGGdUdUdUdUdUdUA TTTAATACGACCCTCAGCACCACACACACCCAA CACA(SEQ ID NO: 18)***** |
| 15. | dU_N.BbvC IB_Nick Primer | ATTTAATACGACCCTCAGCACCAC (SEQ ID NO: 19)***** |

*Underlined sequences indicate EcoNI palindrome
**HEG = hexa-ethyleneglycol
***rA = Adenosine
****dU = deoxy-Uridine
*****Underlined sequence indicates N.BbvC IB nicking endonuclease recognition site

TABLE II

HUMAN STS MARKERS USED FOR REPRESENTATION
ANALYSIS BY QUANTITATIVE REAL-TIME PCR

| STS # | UniSTS Database Name* |
|---|---|
| 4 | SHGC-149956 |
| 8 | csnpmnat1-pcr1-1 |
| 35 | SHGC-146602 |

*Unique names of STS marker sequences from the National Center for Biotechnology Information UniSTS database. Sequences of the STS regions as well as the forward and backward primers used in quantitative real-time PCR can be found in the UniSTS database at the National Center for Biotechnology Information website.

Example 6

Enz-O-Mix DNA Library Preparation and Simultaneous Amplification by Transcription This example demonstrates an exemplary preparation of a library from lambda phage BstEII restriction digest by ligation of hairpin oligonucleotide adaptor comprising deoxy-uridine and T7 promoter sequence combined with the simultaneous isothermal amplification by in vitro transcription with T7 RNA polymerase (see FIG. 6A and FIG. 19A, Enz-O-Mix 2). The adaptor oligonucleotide used in this example (Table I, SEQ ID NO:9) is based on the adaptor sequence described in Example 3 (Table I, SEQ ID NO:8), except that it has the consensus T7 phage promoter sequence incorporated in the loop region. Four enzymatic activities are present in the mix: T4 DNA ligase, T4 DNA polymerase, Uracil-DNA glycosylase (UDG), and T7 RNA polymerase. UDG creates abasic sites by destabilizing the 5' end of the adaptor stem. T4 DNA polymerase generates blunt ends at the restriction fragments leaving intact 5' phosphate groups that are necessary for ligation to the free 3' end of the adaptor by the T4 DNA ligase. T4 DNA polymerase then extends the 3' ends of the newly ligated restriction fragments into the adaptor, thereby displacing the 5' end of the adaptor's stem until an abasic site created by UDG is reached that stops further extension. By doing so, the T4 DNA polymerase generates a fully functional double-stranded T7 promoter, and in vitro transcription is initiated by T7 RNA polymerase.

One hundred nanograms of a lambda phage BstEII restriction DNA fragments (NEB Cat. # M0208S; New England Biolabs; Beverly, Mass.) were incubated in 1× NEBuffer 4 (NEB) with 2 µM adaptor oligonucleotide comprising deoxy-uridine and T7 promoter sequence (Table I, SEQ ID NO:9); 1 mM ATP; 40 µM each dNTP; 500 µM each rNTP; 200 µg/ml BSA; 5.6 mM DTT; 1 unit of uracil-DNA glycosylase (New England Biolabs; Beverly, Mass.); 0.18 unit of T4 DNA polymerase (New England Biolabs; Beverly, Mass.); 600 units of T4 DNA ligase (New England Biolabs; Beverly, Mass.); and 37.5 units of T7 RNA polymerase (Epicentre; Madison, Wis.) for 2 hours at 37° C. in a final volume of 15 µl. A negative control containing no T4 DNA ligase was also run in parallel. Products of the library amplification were analyzed by gel electrophoresis on 1.5% agarose gel after staining with Sybr Gold (Molecular Probes; Carlsbad, Calif.).

Figure 28:
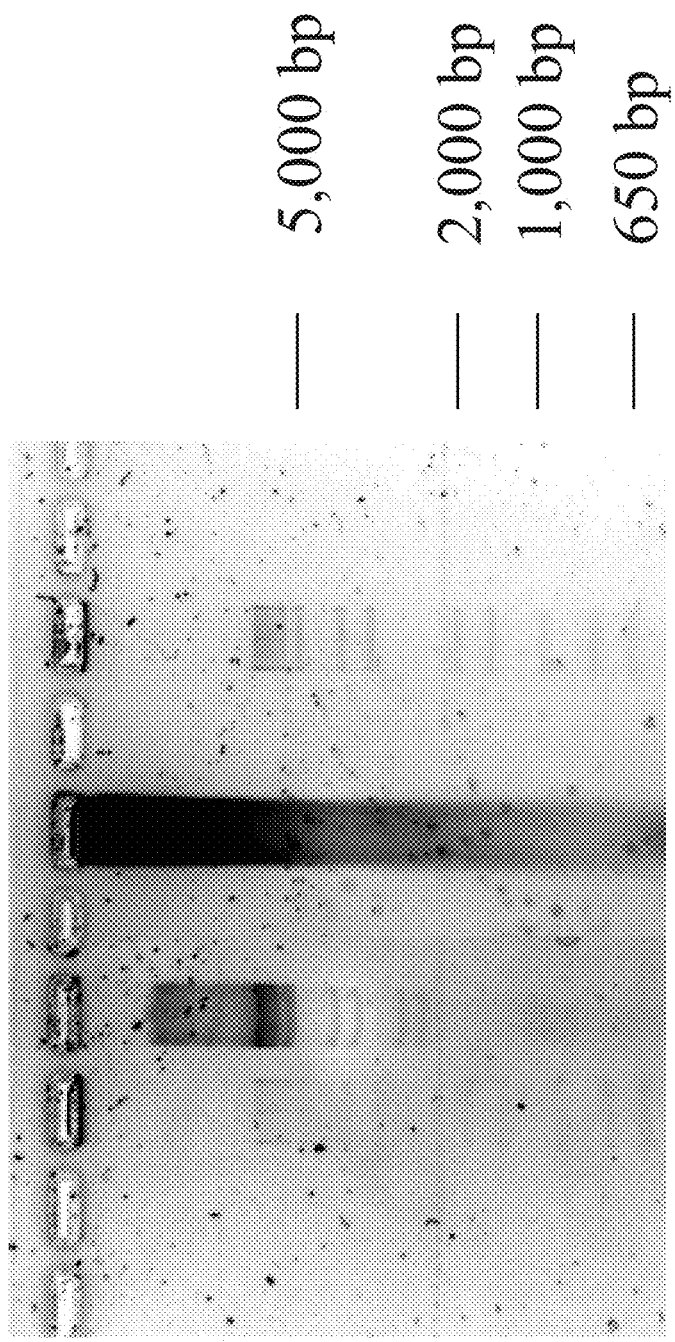
FIG. 28 shows the products of simultaneous whole bacteriophage DNA library synthesis and isothermal amplification by T7 polymerase transcription of lambda DNA digested with restriction endonuclease Bst EII on an agarose gel in the presence (+T4 ligase) or absence of DNA ligase (−T4 ligase).

FIG. 28 shows the products of an exemplary in vitro transcription amplification. As shown, in the presence of all four enzymatic activities the lambda restriction fragments are converted into a library amplified as RNA products, whereas in the absence of T4 DNA ligase no accumulation of RNA occurs. This demonstrates that library preparation and isothermal amplification can be combined into a single-step process.

Example 7

Enz-O-Mix DNA Library Preparation and Simultaneous Immobilization on Solid Support This embodiment is illustrated in FIG. 29 and describes the one-step Enz-O-Mix attachment process for a stem-loop oligonucleotide with a non-replicable linker that is accompanied by immobilization of the synthesized library to the surface of a vessel where the reaction occurs (for example, a tube, micro-plate well, glass slide, micro-beads, etc.). The exemplary reaction mix comprises HMW DNA; a stem-loop oligonucleotide with 3' recessed, 3' protruding or blunt end (FIG. 4), and a non-replicable linker somewhere in the central part of the oligonucleotide; a DNA fragmentation endonuclease, such as restriction enzyme, DNase I, benzonase, methylation-specific nuclease McrBC, apoptotic endonuclease, etc.; a 3' proofreading DNA polymerase (Klenow fragment of the DNA polymerase I, T4 DNA polymerase, etc.); T4 DNA ligase; Enz-O-Mix Universal Buffer; ATP; and dNTPs. In specific embodiments, the reaction occurs inside a tube or a micro-plate well containing a hybridization-capture oligonucleotide (HCO) covalently attached to the inner surface of the reaction vessel. Oligonucleotide HCO has a sequence that is complementary to a portion of the stem-loop oligonucleotide located between the 5' end and the non-replicable linker. Four enzymatic reactions and one hybridization reaction are taking place as follows: (1) DNA fragmentation by a nuclease(s); (2) "polishing" of the DNA ends and the stem-loop oligonucleotide double-stranded stem-region; (3) ligation of the oligonucleotide 3' end to the 5' phosphate of the DNA, leaving a nick between the 3' end of DNA and the 5' end of the oligonucleotide double-stranded stem-region; (4) polymerase extension of the 3' DNA end that propagates toward the end of stem-loop oligonucleotide, displaces the 5' portion of the stem-loop oligonucleotide, stops somewhere within the loop or close to the loop region, at the replication block, and generates single stranded overhangs at the 5' ends of DNA molecules; and (5) immobilization of DNA fragments through a hybridization of the generated 5' overhangs to the surface-attached capture oligonucleotide HCO.

Library immobilization can be non-covalent (as shown on FIG. 29A), or covalent (as shown on FIG. 29B). The first case (non-covalent immobilization) relies solely on the hybridization between the 5' overhang (produced from the stem-loop oligonucleotide during its ligation to DNA ends and subsequent replication) and the capture oligo HCO. The second case (covalent immobilization) involves hybridization as an initial step, but it also involves additional enzymatic steps, such as site-specific cleavage within the single stranded 5' overhang and ligation of the 5' end of DNA to the ligation-capture oligonucleotide construct LCO. The purpose of the cleavage reaction is to generate a 5' phosphate group for the ligation reaction. Such cleavage can be achieved, for example, by incubation with the USER enzyme (a mixture of Uracil DNA glycosylase (UDG) and the DNA glycosylase-lyase Endonuclease VIII; New England Biolabs, Beverly, Mass.). In that case, UDG catalyses the excision of a uracil base (located somewhere at the 5' portion of the stem-loop oligonucleotide), forming an abasic (apyrimidinic) site while leaving the phosphodiester backbone intact. The lyase activity of Endonuclease VIII breaks the phosphodiester backbone at the 3' and 5' sides of the abasic site leaving a 5' phosphate. A generated phosphate group at the end of the 5' overhang is then ligated by a DNA ligase to the 3' end of the ligation-capture oligonucleotide construct LCO (see FIG. 29B).

Library synthesis and immobilization can occur within the specifically designed tubes, micro-well plates, on the surface of micro-slides, or micro-beads (FIG. 30). In all of these cases, the hybridization capture oligonucleotide HCO, or the covalent ligation capture oligo construct LCO, is covalently attached to the inner surface of reaction tubes and plates, spotted on the glass (plastic) surface to create a micro-array, or cover the surface of micro-beads.

Figure 31:
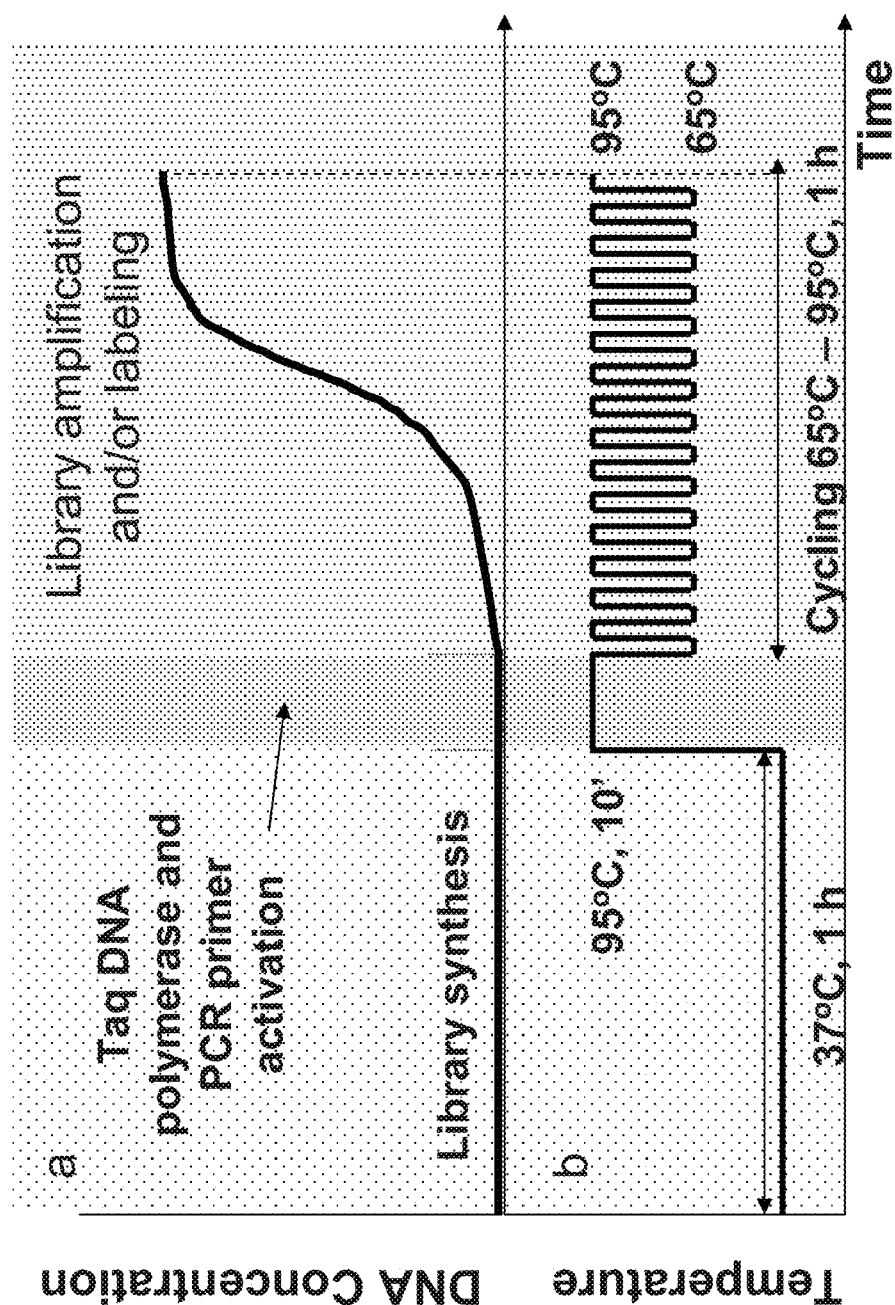
FIG. 31 shows an expected accumulation of DNA in a tube (a) and a typical temperature profile (b) for a one-step, closed tube Enz-O-Mix PCR-based WGA or WMA.

The synthesized and surface-immobilized Whole Genome Library (as described above), or Whole Methylome Library (if the methylation-sensitive restriction nucleases, such as Aci I, Acc II, Asp LE I, Ava I, Bce AI, Bsa HI, Bsh 1236 I, Bsi E1, Bsi SI, Bst FN I, Bst HH I, Bst UI, Cfo I, Hap II, Hga I, Hha I, HinP1 I, Hin 6I, Hpa II, Hpy 99I, Hpy CH4 IV, Hsp AI, Mvn I, and Ssi I, or the methylation-specific nucleases, such as McrBC, are included into the Enx-O-Mix or used after the library synthesis) can be further processed enzymatically, washed, and amplified or stored in an immobilized format. FIG. 31 illustrates a specific but exemplary use of the one-step library synthesis and immobilization in a hypothetical fluidic device. The process starts by a library synthesis (I), is continued by a library immobilization at the bottom of a reaction vessel (II), and is completed by removal of the first reagent mix, washing, and introduction of a new reagent mix (for example, PCR components).

Example 8

Enz-O-Mix DNA Library Preparation and Simultaneous Amplification by Strand Displacement Synthesis This example demonstrates an exemplary preparation of a library from cell-free urine DNA by ligation of hairpin oligonucleotide adaptor comprising deoxy-uridine and N.BbvC IB nicking endonuclease recognition site located at the loop region as illustrated in FIG. 16A followed by isothermal amplification with a strand-displacing DNA polymerase (see FIG. 6A and FIG. 19A, Enz-O-Mix 3). The adaptor oligonucleotide used in this example (Table I, SEQ ID NO:18) is based on the adaptor sequence described in Example 3 (Table I, SEQ ID NO:8), except that it has recognition sequence 5'-CCTCAGC-3' for N.BbvC IB nicking endonuclease in the loop region. In the first step, a stem-loop adaptor attachment is accomplished by using a mix (FIG. 18, Master Mix III) with 3 enzymatic activities: T4 DNA ligase, T4 DNA polymerase, and Uracil-DNA glycosylase. UDG creates abasic sites by destabilizing the 5' end of the adaptor stem. T4 DNA polymerase generates blunt ends at the restriction fragments leaving intact 5' phosphate groups that are necessary for ligation to the free 3' end of the adaptor by the T4 DNA ligase. T4 DNA polymerase then extends the 3' ends of the newly ligated restriction fragments into the adaptor, thereby displacing the 5' end of the adaptor's stem until an abasic site generated by UDG is reached that stops further extension. By doing so, the T4 DNA polymerase generates a functional double-stranded N.BbvC IB nicking endonuclease recognition site. In the second step, following thermal inactivation of T4 DNA polymerase and T4 DNA ligas, the mix is supplemented with two additional enzymatic activities, N.BbvC IB nicking endonuclease generating single-stranded nicks at the adaptor (and internal) sites, and the strand-displacing Klenow fragment of DNA polymerase I, initiating strand displacement from the nicks. The newly synthesized strand is extended until a nick or abasic site at the template strand is encountered. In order to fill-in a second strand and to recreate intact N.BbvC IB recognition sites, an oligonucleotide primer comprising the adaptor's loop sequence at its 5'-end plus five bases complementary to the adaptor's stem at its 3'-end (Table I, SEQ ID NO:19) is also added to the mix. As a result, a self-sustained isothermal DNA amplification process is accomplished.

Cell-free DNA was isolated from urine of healthy donors as described in Example 5. Aliquots of 50 nanograms of DNA were incubated in 1× NEBuffer 4 (New England Biolabs; Beverly, Mass.) with 2 µM adaptor oligonucleotide comprising deoxy-uridine and N.BbvC IB nicking endonuclease recognition site (Table I, SEQ ID NO:18); 1 mM ATP; 40 µM each dNTP; 200 µg/ml BSA; 1 unit of uracil-DNA glycosylase (New England Biolabs; Beverly, Mass.); 0.18 unit of T4 DNA polymerase (New England Biolabs; Beverly, Mass.); and 600 units of T4 DNA ligase (New England Biolabs; Beverly, Mass.) for 1 hour at 37° C. in a final volume of 15 µl. A negative control containing no T4 DNA ligase was run in parallel. Samples were heated at 65° C. for 15 min, cooled to 37° C. and supplemented with 10 units of N.BbvC IB nicking endonuclease (New England Biolabs;

Beverly, Mass.); 27 ng/μl of *E. coli* Single Stranded Binding Protein (SSB protein, USB Corporation, Cleveland, Ohio); 5 units of Klenow Exo-fragment of DNA polymerase I (USB Corporation, Cleveland, Ohio); 0.5 μM of dU_N.BbvC IB_Nick Primer (Table I, SEQ ID NO:19); and 200 μM of each dNTP in a final volume of 30 μl of 1× NEBuffer 4 (New England Biolabs; Beverly, Mass.). To test the effect of additives on the representation of GC-rich sequences such as promoter sites, reactions containing 4% of dimethyl sulfoxide (DMSO, Sigma-Aldrich, St. Louis, Mo.) and 7deaza-dGTP (Roche Diagnostics, Indianapolis, Ind.) were run in parallel. A control reaction containing no N.BbvC IB nicking endonuclease was also included. Samples were incubated for 1 to 3 hours at 37° C. and reactions were stopped by adding 50 mM of EDTA. Products of the library amplification were analyzed by gel electrophoresis on 20% acrylamide TBE gel (Invitrogen Corporation, Carlsbad, Calif.), after staining with Sybr Gold (Molecular Probes; Carlsbad, Calif.).

FIG. 29 shows the products of an exemplary isothermal DNA amplification after 1 hour incubation. As shown, in the presence of all five enzymatic activities the lambda restriction fragments are converted into a library amplified as DNA products, whereas in the absence of T4 DNA ligase or N.BbvC IB nicking endonuclease no accumulation of DNA occurs.

Example 9

Integrated Whole Genome Amplification in a Closed-Tube Reaction Using Degradable Hairpin Adaptor Comprising Deoxy-Uridine Traditionally, preparation of DNA libraries and their subsequent amplification by PCR involves multiple separate processes and different buffer systems. Previous embodiments and examples of this invention have demonstrated that Enz-O-Mx approach can substantially simplify these processes and reduce number of steps necessary for WGA and WMA library preparation to one step. However, in previous Examples the Enzo-O-Mix DNA libraries were first, prepared in small volume (15 μl) of buffer A (NEB 4), and then amplified by PCR in a larger volume (75 ml) of buffer B (Titanium Taq reaction buffer), FIG. 30A. In all of these cases, Enz-O-Mix library synthesis/amplification is performed in two operational steps: step 1—a tube containing DNA is supplemented with the library (WGA or WMA) synthesis reagents and incubated at 37° C. for 1 h, and step 2—a tube is opened, supplemented with PCR amplification buffer/reagents and subjected to temperature cycling. Such an approach is referred to herein as a two-step, opened-tube protocol.

This example introduces further simplification in preparation and PCR-mediated amplification of WGA/WMA libraries when all the necessary synthesis/amplification reagents are introduced into the tube prior reaction, and library synthesis and subsequent amplification occur in the same volume and the same buffer without opening the tube within a pre-programmed thermocycler (FIG. 30B). Such an approach is referred to herein as an integrated, one-step, closed-tube protocol. Due to its simplicity and lack of any human intervention, the integrated, one-step, closed-tube Enz-O-Mix DNA amplification can be easily automated and used for high-throughput research applications and clinical diagnostics.

FIG. 31 shows a one possible temperature profile (b) and an envisioned DNA accumulation during amplification (a), where incubation at 37° C. for 1 h (DNA library synthesis) is followed by heating at 95° C. for 10 min (Taq DNA polymerase activation and stem-loop adaptor→universal PCR primer conversion), and then by thermocycling between 65° C. and 95° C. for 1 h (PCR-mediated whole genome or whole methylome amplification).

Figure 32:
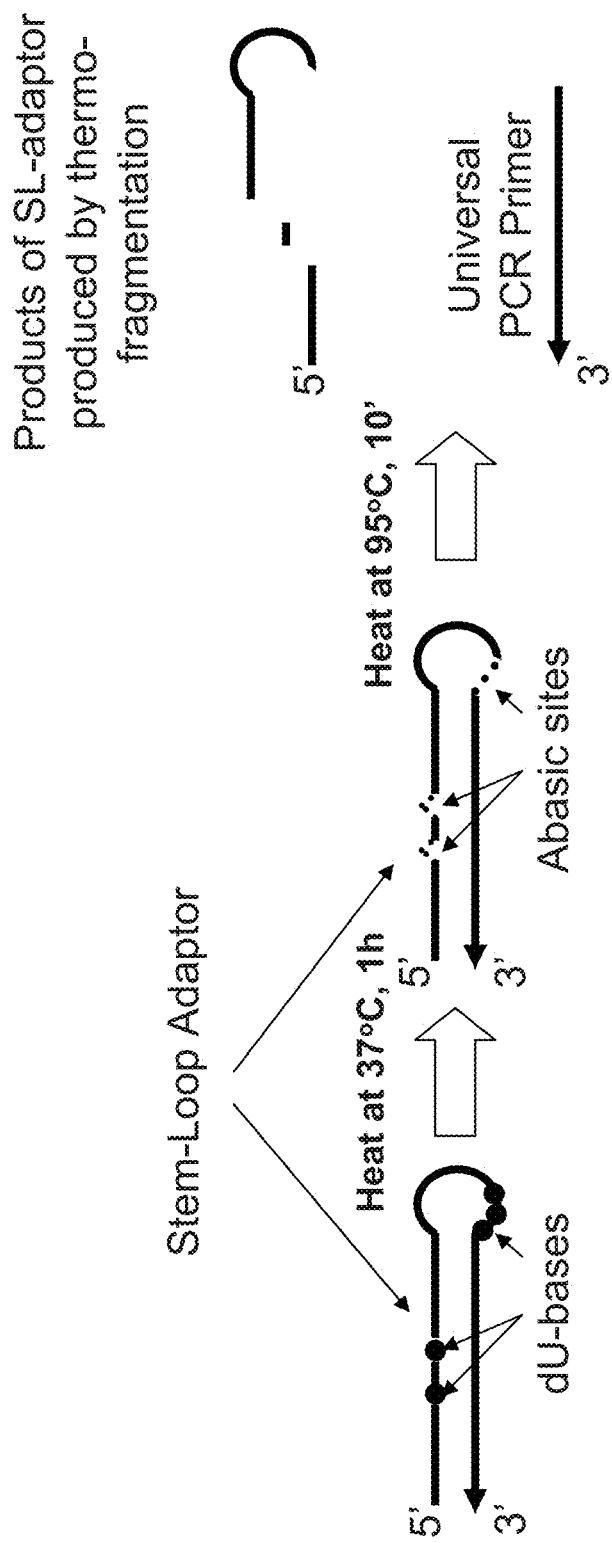
FIG. 32 illustrates heat-induced conversion of a stem-loop oligonucleotide adaptor containing dU-bases within the loop and the 5' stem region into a functional universal PCR primer.

FIG. 32 shows biochemical and physicochemical reactions involved in the transformation of the stem-loop adaptor oligonucleotide into a functional universal PCR primer adequate for efficient amplification of synthesized WGA/WMA libraries. Dual utilization of the stem-loop oligonucleotide as adaptor and PCR primer eliminate a necessity to introduce into reaction an additional single stranded oligo-primer (due to the 3' proofreading activity of a DNA polymerase involved in the library synthesis process such primer should contain at least several nuclease-resistant bases at its 3' terminus).

In this example, a WGA process is described wherein a hairpin oligonucleotide adaptor comprising deoxy-uridine described in Example 3 is ligated via its free 3' end to the 5' phosphates of DNA restriction fragments generated from intact genomic DNA in a single enclosed container exemplary reaction mix comprising 6 exemplary enzymatic activities: AluI restriction endonuclease, RsaI restriction endonuclease, T4 DNA ligase, T4 DNA polymerase, a hot-start Taq DNA polymerase, and Uracil-DNA glycosylase (UDG). In an initial isothermal incubation UDG catalyses the release of free uracil and generates abasic sites in the adaptor's loop region and the 5' half of the hairpin. AluI and RsaI digest the target DNA into restriction fragments. T4 DNA polymerase generates blunt ends of the restriction fragments. T4 DNA ligase generates a phosphodiester bond between the 3' ends of the adaptor molecules and the 5' phosphates of the restriction fragments. T4 DNA polymerase extends the free 3' end of the restriction fragments using as template the ligated 3' end of the hairpin stem until an abasic site is reached that serves as a replication stop (FIG. 10B). Samples are heated to 72° C. to inactivate all thermo-labile enzymes and to activate Taq polymerase, then to 95° C. to degrade the abasic sites of the adaptor and to generate active primer from the remaining intact strand of the adaptor that is free of abasic sites. The resulting library is finally amplified by thermal cycling. The entire process takes place in a single enclosed reaction container under programmed temperature control algorithm and without any intermediate liquid handling.

Figure 33:
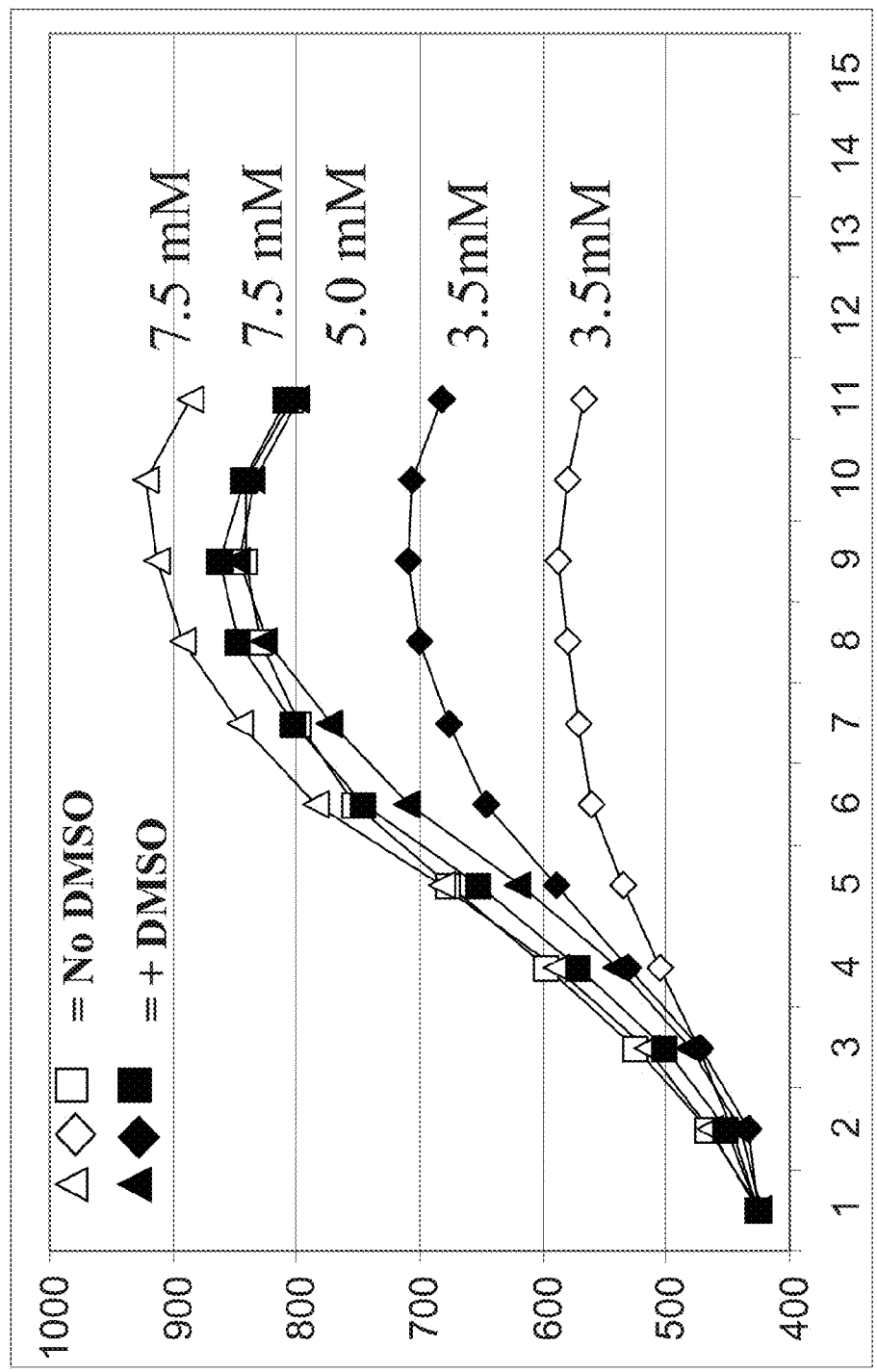
FIG. 33 shows effect of DMSO and magnesium concentration on the whole genome amplification of HMW human DNA isolated from blood using integrated one-step, closed-tube Enz-O-Mix protocol illustrated in FIGS. 30, 31, and 32, and real-time PCR detection.
Figure 34:
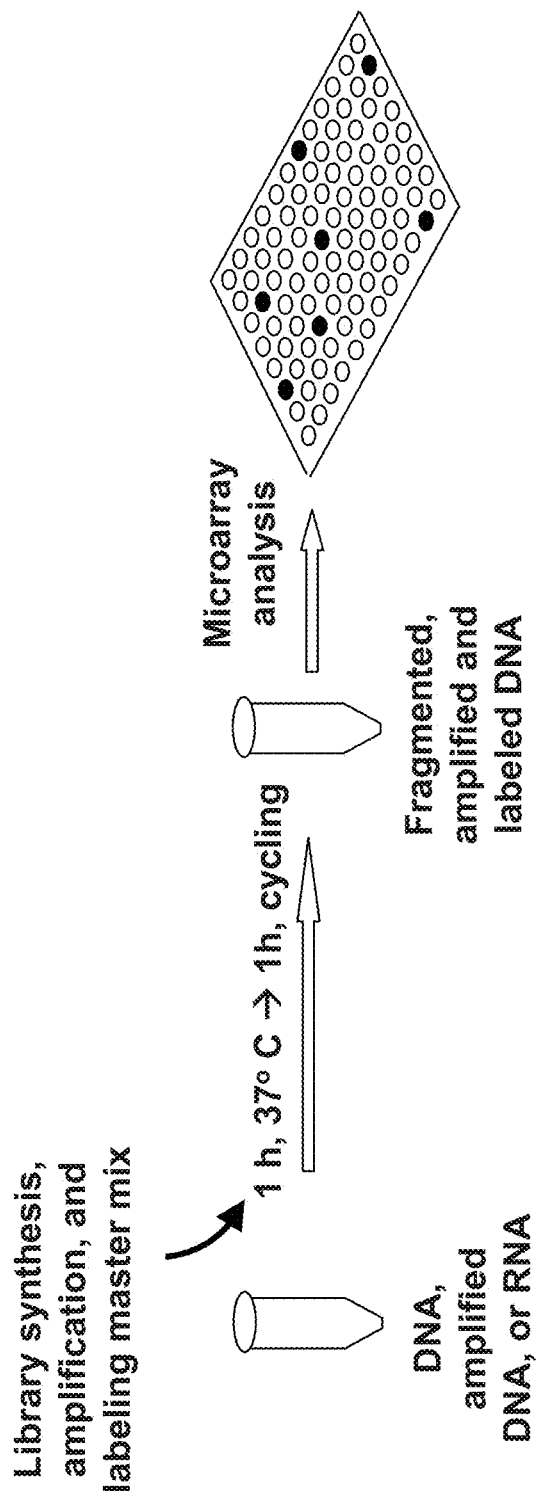
FIG. 34 illustrates application of the one-step, closed tube Enz-O-Mix WGA process (DNA fragmentation, amplification, and labeling) for micro-array analysis.
Figure 35A:
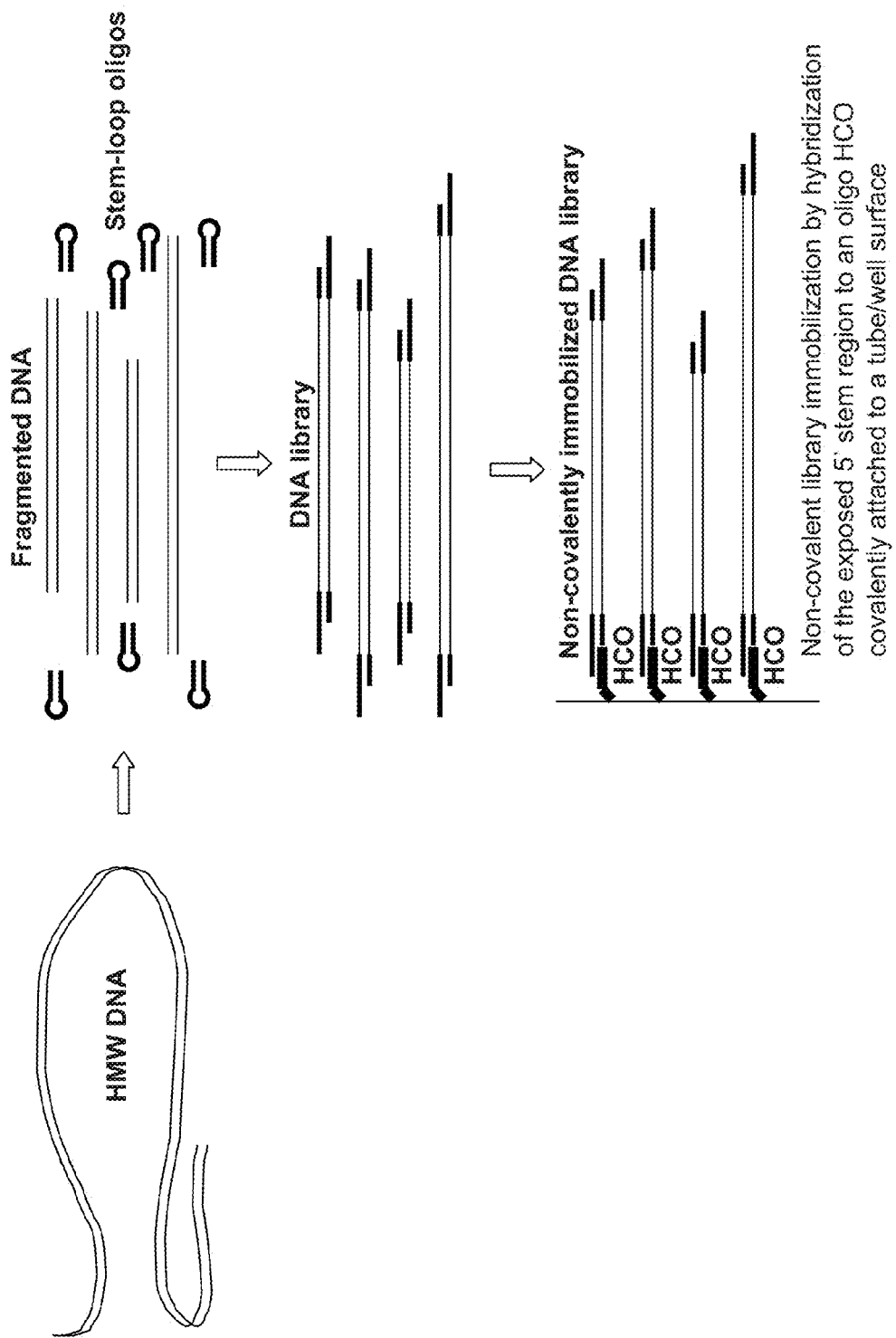
FIGS. 35A and 35B show the one-step process for simultaneous GenomePlex or MethylPlex library synthesis and immobilization.
Figure 35B:
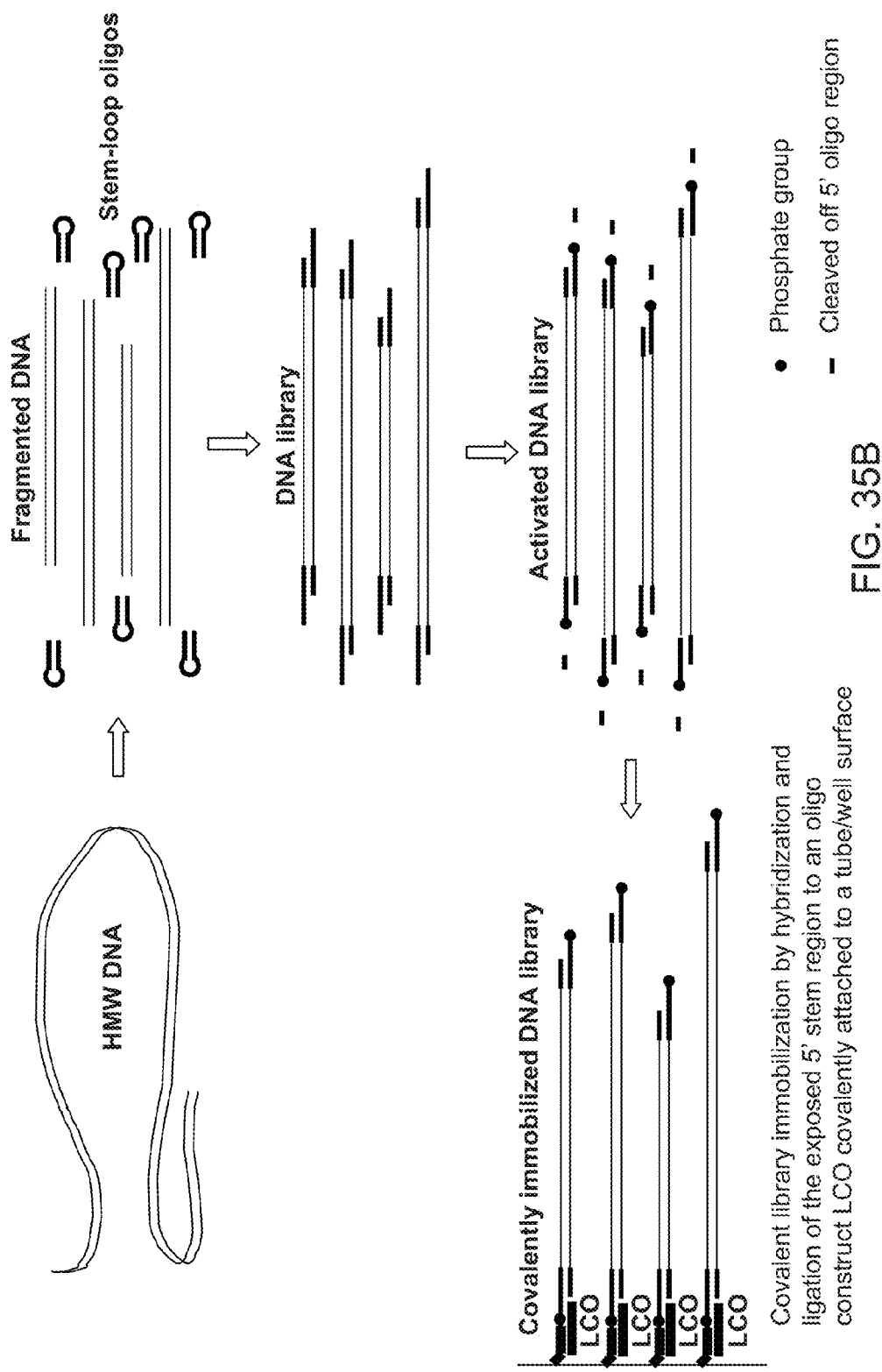
Figure 36:
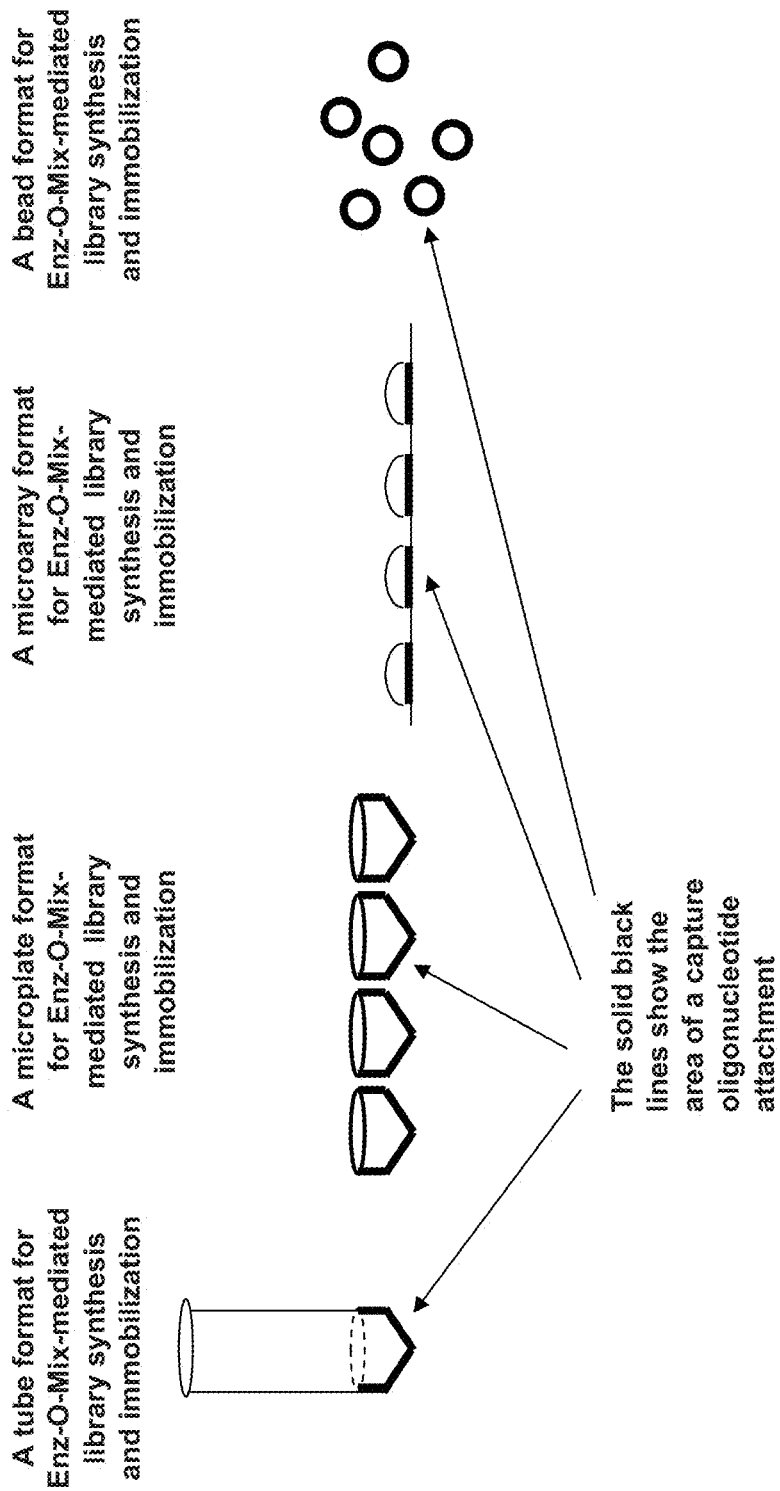
FIG. 36 shows tubes, plates, micro-slides, and micro-beads manufactured for one-step GenomePlex or MethylPlex library synthesis and immobilization.
Figure 37:
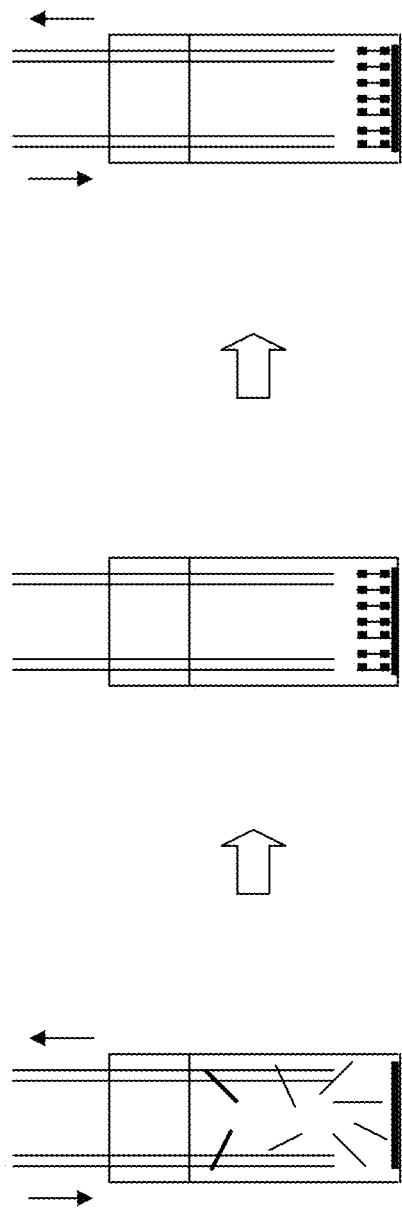
FIG. 37 shows a hypothetical fluidic device that utilizes the one-step GenomePlex or MethylPlex library synthesis and immobilization process.

Ten nanogram aliquots of human genomic DNA isolated from the peripheral blood of a healthy donor by standard procedures were incubated in an exemplary reaction mix comprising: 1× Titanium Taq buffer (Clontech, Mountain View, Calif.); 0.6 μl of Titanium Taq (Clontech, Mountain View, Calif.); 2 μM dU Hairpin Adaptor oligonucleotide (Table I, SEQ ID NO:7); 1 mM ATP; 200 μM dNTPs; 0.36 Units of T4 DNA polymerase; 1200 units of T4 DNA ligase; 2 Units of UDG; 10 units each of AluI and RsaI restriction endonucleases (New England Biolabs; Beverly, Mass.), and 1:10,000 dilutions of fluorescein and SybrGreen I (Molecular Probes; Carlsbad, Calif.) in a final volume of 30 μl. To study the effect of $Mg^{++}$ ions and DMSO, reactions supplemented with $MgCl_2$ at final concentrations of 5 mM and 7.5 mM and with DMSO at a final concentration of 4% were also included (It should be noted that the 1× Titanium Taq buffer contains 3.5 mM $MgCl_2$). Reactions were incubated at 37° C. for 1 hr, followed by 72° C. for 10 min, 95° C. for 10 min, and 11 cycles of 94° C. for 20 sec and 65° C. for 2 min. on i-Cycler real-time PCR instrument (Bio-Rad; Hercules, Calif.). FIG. 33 shows the amplification curves of the resulting libraries. As shown, $Mg^{++}$ concentrations of 5 mM and 7.5 mM in the reaction buffer supported the enzymatic activities present in the mix better than the basic Titanium Taq buffer containing 3.5 mM $MgCl_2$. The presence of 4% DMSO did not have significant effect on the WGA amplification when higher $Mg^{++}$ concentrations were applied.

Example 10

Hot Start PCR Using Degradable Stem-Loop Primers

Specificity and the ability to amplify a single DNA or RNA target is one of the most important requirements for application of PCR in molecular diagnostics. Hot start PCR protocol was introduced to reduce the non-specific primer/template and primer/primer annealing events that occur at lower temperatures and subsequently result in non-specific amplification products. Several methods and corresponding commercial products for performing hot start PCR rely upon the physical separation of PCR reagents until the high temperature of the reaction has been reached. Those products include the following:

1. Wax beads (Ampliwax PCR Gems, Perkin Elmer) that create a temporary barrier between dNTPs, buffer, and $MgCl_2$ on one side of the wax layer, and DNA template and DNA polymerase on another side.

2. Small beads of wax with encapsulated Taq DNA polymerase (Taq Bead Hot Start Polymerase, Promega). In this case Taq DNA polymerase is released when the reaction reaches 60° C.

3. Small beads of wax with encapsulated magnesium (StartaSpere, Stratagene).

4. Taq DNA polymerase inactivated by antibody (JumStart Taq DNA polymerase, Sigma; TaqStart and TthStart, Clontech; AmpliTaq Gold, PE Biosystems; HotStarTaq, Qiage; etc.). Antibody binds to the polymerase and inactivates it at low temperature but denatures and releases the active polymerase at high temperature.

Example 9 introduced the idea of using a degradable, dU-containing stem-loop oligonucleotide-adaptor as a universal PCR primer (see FIG. 32) for whole genome amplification. This embodiment extends the use of degradable, dU-containing stem-loop oligonucleotides as "hot start" PCR primers for locus-specific DNA amplification.

Figure 38:
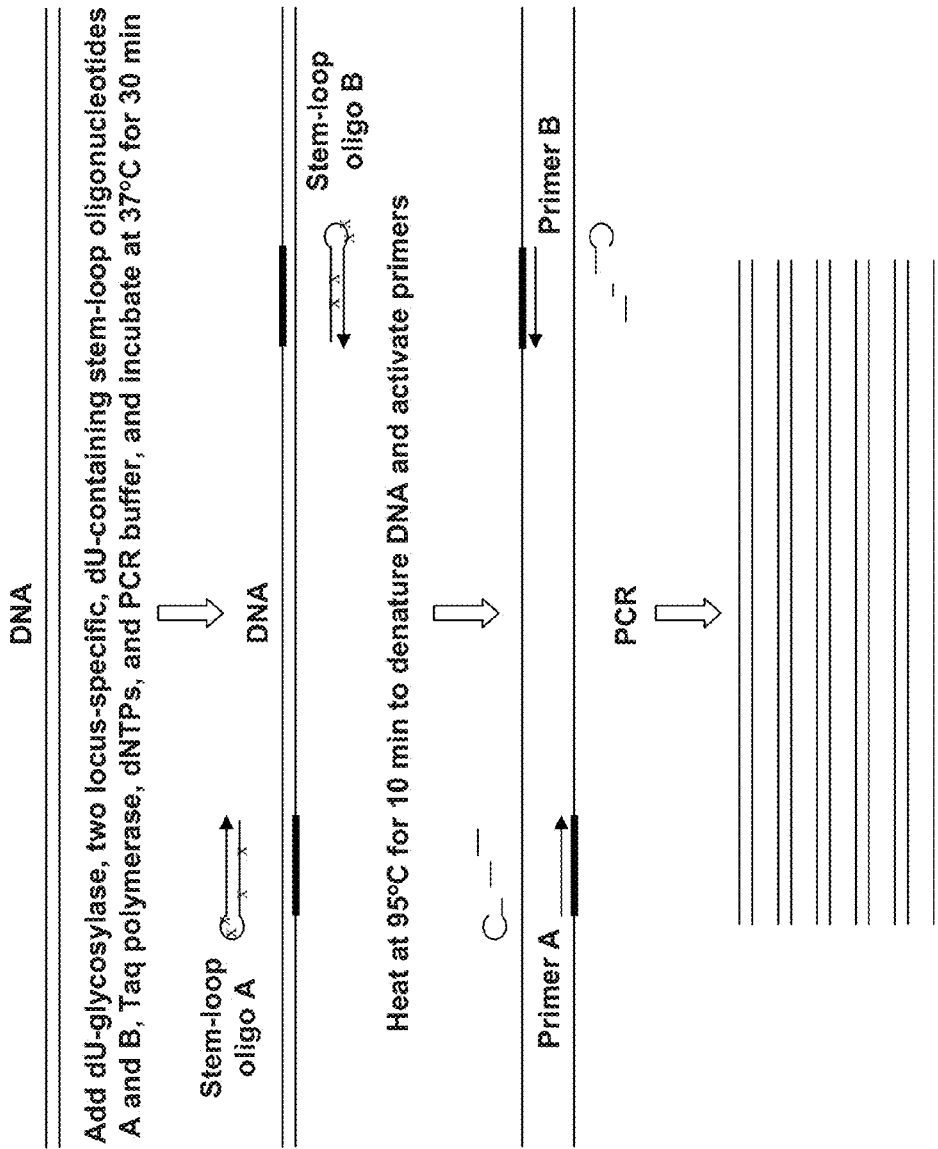
FIG. 38 illustrates hot start locus-specific PCR amplification of DNA using degradable stem-loop primers.
Figure 39:
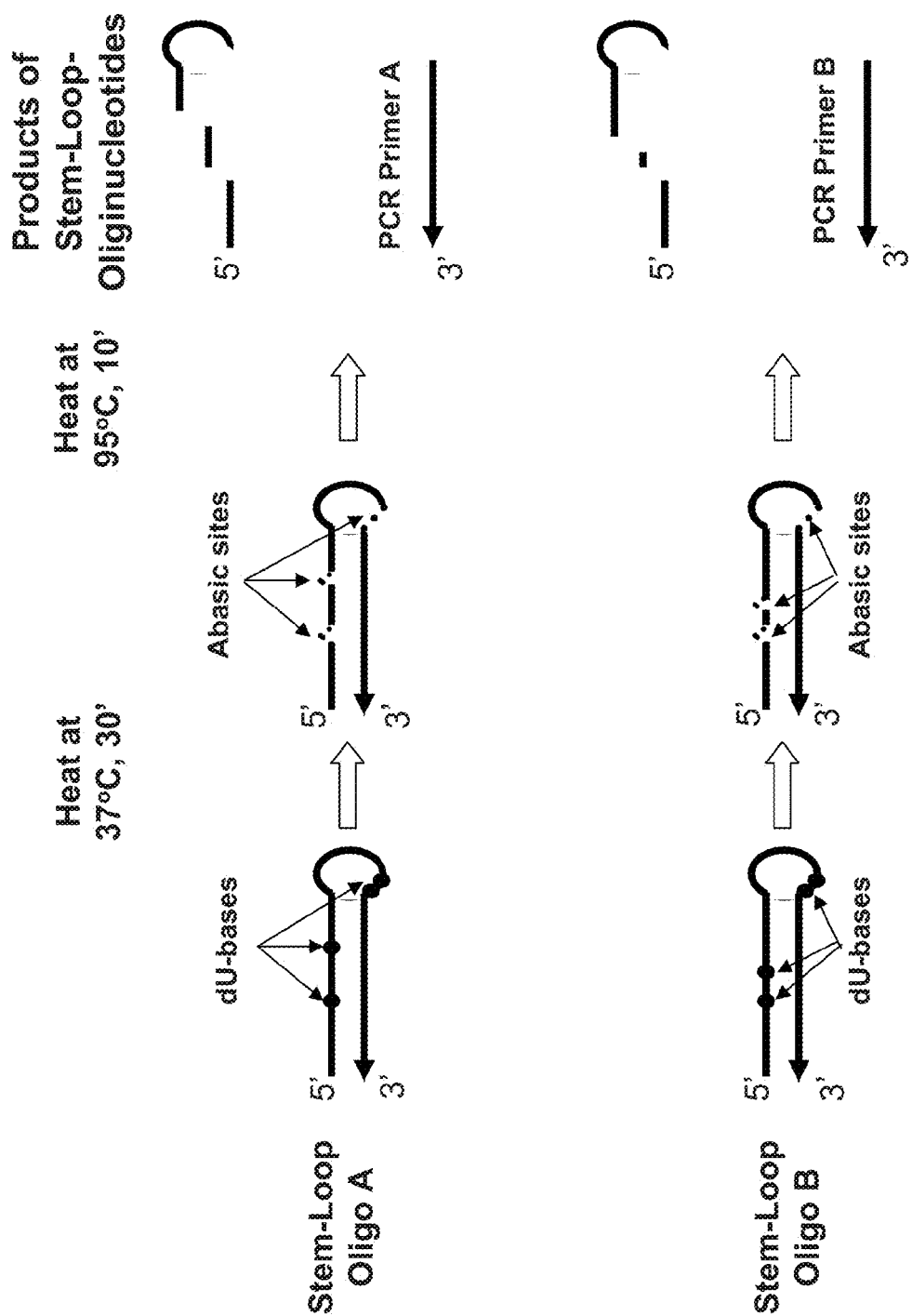
FIG. 39 shows the specific events that lead to a conversion of the inactive stem-loop oligonucleotides into the active PCR primers.

As shown in FIG. 38 and FIG. 39, both PCR primers are synthesized in a form of stem-loop oligonucleotides A and B. The 3' portion of the stem-loop oligonucleotides represents the primer sequence (no dU bases); the 5' portion represents the sequence complementary to the primer sequence and comprises one or more dU bases substituting dT bases; and the loop comprises several dT and dU bases.

Figure 40:
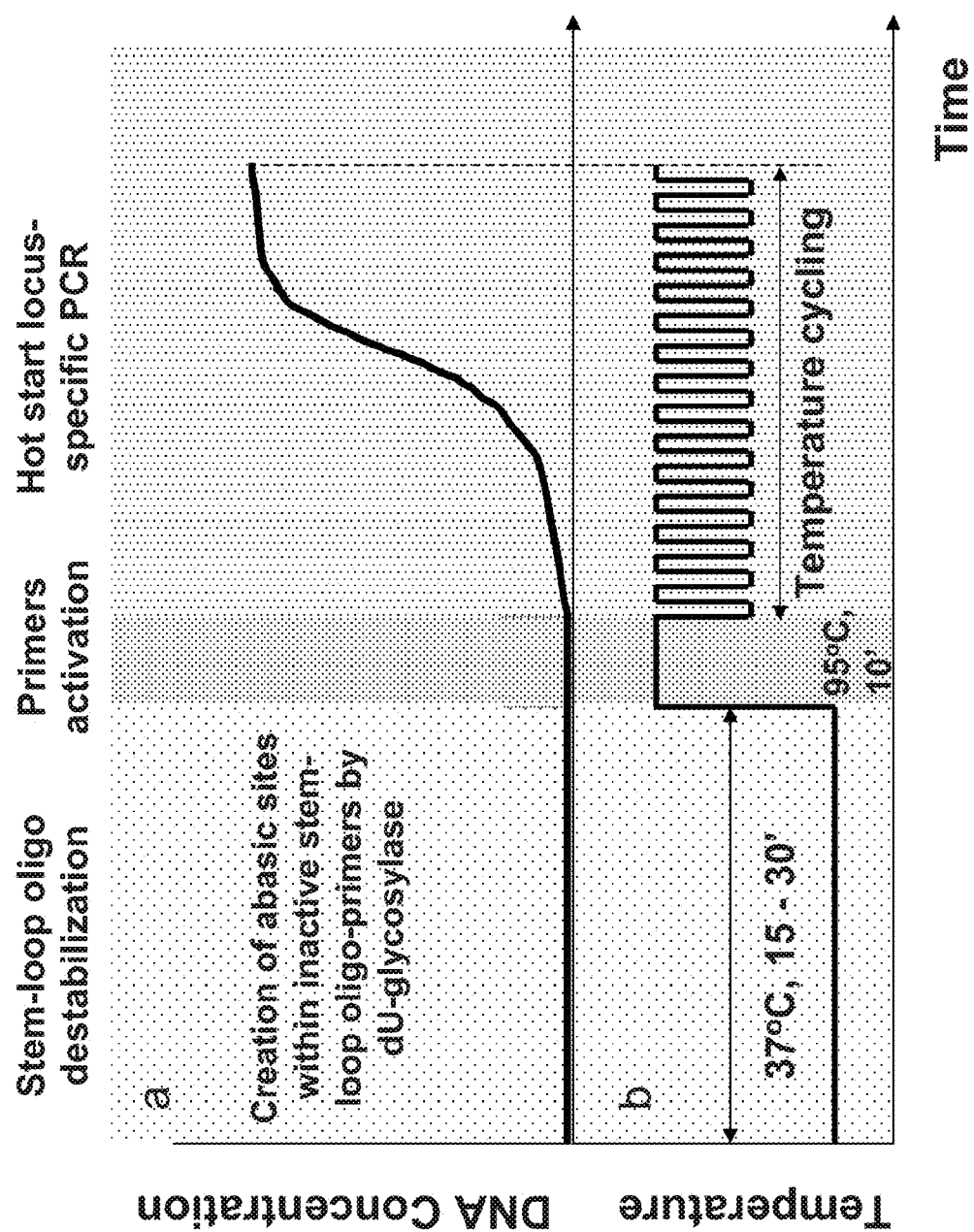
FIG. 40 shows accumulation of a specific PCR product (A) and a typical temperature profile (B) for a hot start PCR using degradable stem-loop primers

PCR reaction is assembled by mixing together DNA, dNTPs, magnesium, PCR buffer, Taq DNA polymerase (or any other thermostable DNA polymerase), and dU-glycosylase (FIG. 38 and FIG. 40). A thermocycler is programmed to have the following conditions:

a) Incubation step at 37° C. for 15-30 min that is necessary to convert all dU bases within the stem-loop oligonucleotides A and B into the abasic sites;

b) Incubation step at 95° C. for 10 min that is necessary to denature DNA, introduce breaks at the abasic sites within the stem-loop oligonucleotides A and B, and thus release the active primers A and B;

c) A regular PCR cycling mode that amplifies the DNA region defined by the primer A and B.

The conversion of the stem-loop oligonucleotides A and B into PCR primers A and B (see FIG. 39) results from several breaks introduced by heating the loop and the 5' portion of the oligonucleotides. At high temperature, the small oligonucleotides originated from the 5' stem regions can not form stable interaction with the remaining intact 3' primer regions and do not affect the PCR process. In general, the position of dU bases within the 5' stem region is dictated by the location of thymines in a DNA sequence, although they can be also introduced at another nucleotide position (thus generating a stem with one ore several mismatched bases). The number of dU bases within the 5' stem and the loop regions can vary from 1 to about 6, and an optimal number can be determined empirically.

The proposed hot start primer method can be used in PCR and other DNA/RNA amplification methods that utilize thermostable polymerases. It has several advantages over the hot start PCR methods that involve either non-degradable hairpin primers with short stem [Kaboev, O. K., et al., 2000; Ailenberg, M., and Silverman, M., 2000], or duplex primers [Kong, D., et al., 2004]: a) the hybridization kinetics are not compromised by the presence of a stem region (as it might be in the case of non-degradable stem-loop primer method); b) no inverted repeat is formed at the ends of PCR amplicons that could substantially reduce the efficiency of the PCR amplification process (as it happens in the case of non-degradable stem-loop primer method); and c) oligonucleotides complementary to the priming oligonucleotide (products of the stem-loop oligonucleotide fragmentation) are short, do not form stable interaction with the remaining intact 3' primer regions and, as a result, do not affect the PCR process (as it possible in the duplex primer method). Advantages over other existing hot-start methods include but are not limited to the following: a) no phase separation is necessary and all reaction components are originally present in the same reaction mix simplifying storage and reducing production cost; b) no expensive blocking antibodies are involved; c) no mutagenesis or chemical modification of amino acid residues in the thermostable DNA polymerase are required whatsoever.

REFERENCES

All patents and publications mentioned in the specification are indicative of the level of those skilled in the art to which the invention pertains. All patents and publications are herein incorporated by reference to the same extent as if each individual publication was specifically and individually indicated to be incorporated by reference.

PATENTS AND PATENT APPLICATIONS

U.S. Pat. No. 6,777,187
U.S. patent application Ser. No. 10/797,333
U.S. patent application Ser. No. 10/795,667
U.S. patent application Ser. No. 11/071,864

PUBLICATIONS

Barns, W. M. PCR amplification of up to 35-kb DNA with high fidelity and high yield from lambda bacteriophage templates. Proc. Natl. Acad. Sci. USA, 91, 2216-2220, (1994).

Broude, N. E., Stem-loop oligonucleotides: a robust tool for molecular biology and biotechnology. Trends in Biotechnology, 20, 249-256, (2002).

de Baar, M. P., et al. One-tube real-time isothermal amplification assay to identify and distinguish human immunodeficiency using type I subtypes A, B, and C and circulating recombinant forms AE and AG. J. Clin. Microbiol. 39, 1895-1902, (2001).

Deiman, B., et al. Characteristics and applications of nucleic acid sequence-based amplification (NASBA). Mol. Biotechnology, 20, 163-179, (2002); Hill, C. S., Molecular diagnostic testing for infectious diseases using TMA technology. Expert Rev Mol Diagn, 1, 445-455, (2001).

Goddard, N. L., et al. Sequence dependent rigidity of single stranded DNA. Phys. Rev. Lett. 85, 2400-2403, (2000).

Hamad-Schifferli, K., et al. Remote electronic control of DNA hybridization through inductive coupling to an attached metal nanocrystal antenna. Nature, 415, 152-155, (2002).

Hellyer, T. J., and Naolean, J. G., Strand displacement amplification: a versatile tool for molecular diagnostics. Expert Rev Mol Diagn, 4, 251-261, (2004).

Kaboev, O. K., et al. PCR hot start using primers with the structure of molecular beacons (stem-loop-like structure). Nucleic Acids Res., 28, e94, (2000); Ailenberg, M., and Silverman, M. Controlled hot start and improved specificity in carrying out PCR utilizing touch-up and loop incorporated primers (TULIPS). Bio-Techniques, 29, 1018-1024, (2000).

Kong, D., et al. PCR hot-start using duplex primers. Biotechnol. Lett. 26, 277-280, (2004).

Liu, et al. Molecular beacons for DNA biosensors with micrometer to submicrometer dimensions. Anal. Biochem. 283, 56-63, (2000).

Mackay, I. M., et al. Real-time PCR in virology. Nucleic Acids Res., 30, 1292-1305, (2002); Elnifro, E. M., et al. Multiplex PCR: optimization and application in diagnostic virology. Clin. Microbiol. Rev. 13, 559-570, (2000).

Riccelli, P. V., et al. Hybridization of single-stranded DNA targets to immobilized complementary DNA probes: comparison of stem-loop versus linear capture probes. Nucleic Acids Res., 29, 996-1004, (2001).

Sokol, D. L., et al. Real-time detection of DNA-RNA hybridization in living cells. Proc. Natl. Acad. Sci. USA, 95, 11538-11543, (1998).

Summerer, D., and Marx, A., A molecular beacon for quantitative monitoring of the DNA polymerase reaction in real-time. Angew. Chem. Int. 41, 3620-3622, (2002).

Tyagi, S., and Kramer, F. R., Molecular beacons: probes that fluoresce upon hybridization. Nat Biotechnol. 14, 303-308, (1996).

Tyagi, S., et al. Multicolor molecular beacons for allele discrimination. Nat. Biotechnol. 16, 49-53, (1998).

van Deursen, P. B. H., et al., A novel quantitative multiplex NASBA method: application to measuring tissue factor and CD14 mRNA levels in human monocytes. Nucleic Acids Res, 27, e15, (1999).

Whitcombe, D., et al. Detection of PCR products using self-probing amplicons and fluorescence. Nat. Biotechnol. 17, 804-807, (1999)

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A method of producing a primer for use in an amplification reaction comprising:
   (a) providing at least one stem-loop oligonucleotide comprising an inverted repeat, a loop, and at least one degradable site or site capable of becoming a degradable site;
   (b) subjecting the at least one stem-loop oligonucleotide to conditions such that a phosphodiester bond of the at least one stem-loop oligonucleotide at the at least one degradable site or site capable of becoming a degradable site is broken, thereby producing primers for use in an amplification reaction; and
   (c) carrying out an amplification reaction using the primers.

2. The method of claim 1, wherein the conditions of step (b) comprise heating the at least one stem-loop oligonucleotide.

3. The method of claim 2, wherein the conditions of step (b) comprises incubating the stem-loop oligonucleotide with uracil-DNA glycosylase to convert the at least one site capable of becoming a degradable site into an abasic site prior to said heating.

4. The method of claim 1, wherein prior to step (b) a portion of the at least one stem-loop oligonucleotide is ligated to a nucleic acid molecule to provide a stem-loop oligonucleotide ligated nucleic acid molecule, and the amplification step is carried out on the stem-loop ligated nucleic acid molecule.

5. The method of claim 4, wherein the nucleic acid molecule is a double stranded DNA molecule.

6. The method of claim 4, wherein the nucleic acid molecule is a double stranded DNA/RNA hybrid.

7. The method of claim 1, wherein the amplification is a polymerase chain reaction.

8. The method of claim 1, wherein the amplification is a linear amplification.

9. The method of claim 1, wherein the amplification reaction is carried out on a nucleic acid molecule, such that the nucleic acid molecule is amplified.

10. The method of claim 9, further defined as occurring in a single suitable solution, wherein the method occurs in the absence of exogenous manipulation.

11. The method of claim 10, wherein the solution comprises one or more of the following:
   an adaptor molecule;
   ligase;
   DNA polymerase;
   one or more endonucleases;
   RNA polymerase;
   reverse transcriptase;
   RNase H;
   uracil-DNA glycosylase;
   nickase;
   thermophilic DNA polymerase;
   ATP;
   rNTPs; and
   dNTPs.

12. The method of claim 1, wherein the degradable site is an abasic site.

13. The method of claim 12, wherein the conditions sufficient to break the phosphodiester bonds of the degradable site comprise exposure to heat.

14. The method of claim 1, wherein the site capable of becoming a degradable site is further defined as a base that can be enzymatically converted to a degradable site.

15. The method of claim 14, wherein the base that can be enzymatically converted to a degradable site is deoxyuridine.

16. The method of claim 15, wherein the conditions sufficient to break the phosphodiester bonds of the site capable of becoming a degradable site comprise incubating the stem-loop oligonucleotide with uracil-DNA glycosylase to convert the deoxyuridine into an abasic.

17. The method of claim 16, wherein the conditions further comprise exposing the stem-loop oligonucleotide to heat.

18. The method of claim 16, wherein the conditions further comprise incubating the stem-loop oligonucleotide with endonuclease VIII.

19. The method of claim 1, wherein the stem-loop oligonucleotide comprises:
   (i) a 5' portion comprising a sequence at least 80% complementary to the 3' primer portion;
   (ii) a loop portion coupled to the 3'-end of the 5' portion; and
   (iii) a 3' primer portion coupled to the 3'-end of the loop portion,
   wherein the 5' portion and/or the loop portion comprise at least one degradable site or site capable of becoming a degradable site.

20. The method of claim 19, wherein the 5' portion and/or the loop portion comprise 2, 3, 4, 5, or 6 degradable sites or sites capable of becoming degradable sites.

21. The method of claim 1, wherein the loop portion comprises a known sequence.

22. The method of claim 21, wherein the known sequence is a regulatory sequence, an endonuclease recognition sequence, a hybridization sequence, or a primer binding sequence.

23. The method of claim 1, wherein the loop portion comprises a non-replicable base or sequence.

24. The method of claim 23, wherein the non-replicable base or sequence is an abasic site or sequence, hexaethylene glycol, or a bulky chemical moiety attached to the sugar-phosphate backbone or the base.

25. The method of claim 19, wherein the 3' primer portion is complementary to a known target sequence or sequences.

26. The method of claim 25, wherein the known target sequence is a library adaptor sequence.

27. The method of claim 25, wherein the known target sequence is a genomic sequence or sequences.

28. The method of claim 1, wherein the stem-loop oligonucleotide comprises a blunt end.

29. The method of claim 1, wherein the stem-loop oligonucleotide comprises an overhanging end.

30. The method of claim 1, wherein the 5' end lacks a phosphate.

31. The method of claim 1, wherein the 3' end is not ligation-competent.

32. The method of claim 31, wherein the 3' end is recessed.

33. The method of claim 31, wherein the 3' end comprises a blocked nucleotide.

* * * * *

SEQUENCE LISTING

```
<160> NUMBER OF SEQ ID NOS: 20

<210> SEQ ID NO 1
<211> LENGTH: 32
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 1
ccaaacacac ccaacacacc taaaaaaggt gt                                    32

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 2
tgtgttgggt gtgtttgg                                                   18

<210> SEQ ID NO 3
<211> LENGTH: 40
```

```
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 3
aagagagagg gaaggaagaa aacttccttc cctctctctt                              40

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 4
cttccttccc tctctctt                                                     18

<210> SEQ ID NO 5
<211> LENGTH: 28
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 5
ccaaacacac ccaacacaaa aagtgttg                                           28

<210> SEQ ID NO 6
<211> LENGTH: 28
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 6
ccaaacacac ccaacacaaa aagtgttg                                           28

<210> SEQ ID NO 7
<211> LENGTH: 40
<212> TYPE: DNA
<213> ORGANISM: Artificial Sequence
<220> FEATURE:
<223> OTHER INFORMATION: Description of Artificial Sequence: Synthetic
      Primer
<220> FEATURE:
<221> NAME/KEY: misc_feature
<222> LOCATION: (10)..(10)
<223> OTHER INFORMATION: n = deoxy-Uridine
<220> FEATURE:
<221> NAME/KEY: misc_feature
<222> LOCATION: (12)..(12)
<223> OTHER INFORMATION: n = deoxy-Uridine
<220> FEATURE:
<221> NAME/KEY: misc_feature
<222> LOCATION: (19)..(24)
<223> OTHER INFORMATION: n = deoxy-Uridine

<400> SEQUENCE: 7
tgtgttgggn gngtgtggnn nnnnccacac acacccaaca                              40

<210> SEQ ID NO 8
<211> LENGTH: 18
<212> TYPE: DNA
<213> ORGANISM: Artificial Sequence
```

```
<220> FEATURE:
<223> OTHER INFORMATION: Description of Artificial Sequence: Synthetic
      Primer

<400> SEQUENCE: 8
ccacacacac ccaacaca                                                        18

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 9
ggaggagtct ttcgagttca a                                                    21

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 10
cgggaggaat acagacacgt ctt                                                  23

<210> SEQ ID NO 11
<211> LENGTH: 19
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 11
ggaaagaggg aaaggcttc                                                       19

<210> SEQ ID NO 12
<211> LENGTH: 19
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 12
ccccagtgct gagtcacgg                                                       19

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 13
gggtgggagg aagcatcgtc                                                      20

<210> SEQ ID NO 14
<211> LENGTH: 21
<212> TYPE: DNA
<213> ORGANISM: Artificial Sequence
<220> FEATURE:
```

<223> OTHER INFORMATION: Description of Artificial Sequence: Synthetic
      Primer

<400> SEQUENCE: 14
ggtctccagc atctccacga a                                              21

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 15
agaactggct ctcggaagcg                                                20

<210> SEQ ID NO 16
<211> LENGTH: 19
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 16
gggagcagag ggggtagtc                                                 19

<210> SEQ ID NO 17
<211> LENGTH: 68
<212> TYPE: DNA
<213> ORGANISM: Artificial Sequence
<220> FEATURE:
<223> OTHER INFORMATION: Description of Artificial Sequence: Synthetic
      Primer
<220> FEATURE:
<221> NAME/KEY: misc_feature
<222> LOCATION: (10)..(10)
<223> OTHER INFORMATION: n = deoxy-Uridine
<220> FEATURE:
<221> NAME/KEY: misc_feature
<222> LOCATION: (12)..(12)
<223> OTHER INFORMATION: n = deoxy-Uridine
<220> FEATURE:
<221> NAME/KEY: misc_feature
<222> LOCATION: (19)..(24)
<223> OTHER INFORMATION: n = deoxy-Uridine

<400> SEQUENCE: 17
tgtgttgggn gngtgtggnn nnnnatttaa tacgactcac tataggdaga ccacacacac    60
ccaacaca                                                             68

<210> SEQ ID NO 18
<211> LENGTH: 62
<212> TYPE: DNA
<213> ORGANISM: Artificial Sequence
<220> FEATURE:
<223> OTHER INFORMATION: Description of Artificial Sequence: Synthetic
      Primer
<220> FEATURE:
<221> NAME/KEY: misc_feature
<222> LOCATION: (10)..(10)
<223> OTHER INFORMATION: n=deoxy-Uridine
<220> FEATURE:
<221> NAME/KEY: misc_feature
<222> LOCATION: (12)..(12)
<223> OTHER INFORMATION: n=deoxy-Uridine
<220> FEATURE:
<221> NAME/KEY: misc_feature
<222> LOCATION: (19)..(24)

```
<223> OTHER INFORMATION: n=deoxy-Uridine

<400> SEQUENCE: 18
tgtgttgggn gngtgtggnn nnnnatttaa tacgaccctc agcaccacac acacccaaca      60
ca                                                                    62

<210> SEQ ID NO 19
<211> LENGTH: 24
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 19
atttaatacg accctcagca ccac                                            24

<210> SEQ ID NO 20
<211> LENGTH: 11
<212> TYPE: DNA
<213> ORGANISM: Artificial Sequence
<220> FEATURE:
<223> OTHER INFORMATION: Description of Artificial Sequence:  Synthetic
      Primer
<220> FEATURE:
<221> NAME/KEY: misc_feature
<222> LOCATION: (4)..(8)
<223> OTHER INFORMATION: n is a, c, g, or t

<400> SEQUENCE: 20
cctnnnnnag g                                                          11
```